United States Patent
Rongved et al.

(10) Patent No.: US 11,958,842 B2
(45) Date of Patent: Apr. 16, 2024

(54) SUBSTITUTED PHENAZINES AND METHODS OF TREATING CANCER AND BACTERIAL DISEASES

(71) Applicant: Adjutec Pharma AS, Oslo (NO)

(72) Inventors: Pål Rongved, Oslo (NO); Ove Alexander Høgmoen Åstrand, Haslum (NO); Elvar Ørn Viktorsson, Oslo (NO); Ørjan Samuelson, Tromsø (NO); Adam Heikal, Kolsås (NO); Ole Andreas Løchen Økstad, Moss (NO); Geir Kildahl-Andersen, Oslo (NO)

(73) Assignee: ADJUTEC PHARMA AS, Oslo (NO)

( * ) Notice: Subject to any disclaimer, the term of this patent is extended or adjusted under 35 U.S.C. 154(b) by 117 days.

(21) Appl. No.: 17/239,976

(22) Filed: Apr. 26, 2021

(65) Prior Publication Data

US 2021/0292313 A1 Sep. 23, 2021

Related U.S. Application Data

(63) Continuation of application No. 16/469,948, filed as application No. PCT/GB2017/053787 on Dec. 18, 2017, now Pat. No. 11,046,678.

(30) Foreign Application Priority Data

Dec. 16, 2016 (GB) ...................... 1621520

(51) Int. Cl.
| | |
|---|---|
| A61K 31/498 | (2006.01) |
| A61K 47/68 | (2017.01) |
| A61P 31/04 | (2006.01) |
| A61P 35/00 | (2006.01) |
| C07D 241/46 | (2006.01) |
| C07D 241/52 | (2006.01) |
| C07D 403/12 | (2006.01) |
| C07D 403/14 | (2006.01) |
| C07D 413/12 | (2006.01) |
| A61K 45/06 | (2006.01) |

(52) U.S. Cl.
CPC ............ *C07D 413/12* (2013.01); *A61K 47/68* (2017.08); *A61P 31/04* (2018.01); *A61P 35/00* (2018.01); *C07D 241/52* (2013.01); *C07D 403/12* (2013.01); *C07D 403/14* (2013.01); *A61K 45/06* (2013.01)

(58) Field of Classification Search
CPC ........................... A61K 31/498; C07D 241/46
USPC ......................... 514/250; 544/347
See application file for complete search history.

(56) References Cited

U.S. PATENT DOCUMENTS

| | | | |
|---|---|---|---|
| 3,530,130 | A | 9/1970 | Weigele |
| 3,678,051 | A | 7/1972 | Leimgruber et al. |
| 2008/0269231 | A1 | 10/2008 | Tunac |
| 2009/0131342 | A1* | 5/2009 | Ellis ...................... A61K 31/04 |
| | | | 514/48 |

FOREIGN PATENT DOCUMENTS

| | | |
|---|---|---|
| CN | 1 951 923 | 4/2007 |
| CN | 104 974 100 | 10/2015 |
| DE | 21 44 884 | 3/1973 |
| GB | 1215815 | 12/1970 |
| WO | 2004/113323 | 12/2004 |
| WO | 2015/063516 | 5/2015 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Hurst et al., "The Therapy of Experimental Psittacosis and Lymphogranuloma Vereum (Inguinale)", Brit. J. Pharmacol., vol. 8, No. 1: pp. 297-308 (1953).
Viktorsson et al., "Total synthesis and antileukemic evaluations of the phenazine 5,10-dioxide natural products iodinin, myxin and their derivatives", Bioorganic & Medicinal Chemistry, vol. 25, No. 7: pp. 2285-2293 (2017).
International Search Report in corresponding PCT/GB2017/053787 dated Feb. 22, 2018.
Shchukina I N V Savitskaya M. N. et al. "On Derivatives of 8-Oxyninoline and their Antibacterial Action. I. 8-Aryloxy and 8-Alcohoxyinolines", Zhurnal Obshchei Khimii, Jan. 1, 1952, vol. 22, pp. 1218-1224.
Endo Hideo et al. "Studies on Antitumor Activity of Phenazine Derivatives Against S 180 and C 63 in Mice (III)", Science Reports of the Research Institutes, Jan. 1, 1966, vol. 13, No. 3, pp. 197-199.
Third Party Observation submitted on Apr. 16, 2019, in PCT/GB2017/053787.

(Continued)

*Primary Examiner* — Douglas M Willis
(74) *Attorney, Agent, or Firm* — Wenderoth, Lind & Ponack, L.L.P.

(57) ABSTRACT

A combination product comprising a carbapenem and a compound of formula (I'), or a pharmaceutically acceptable salt thereof:

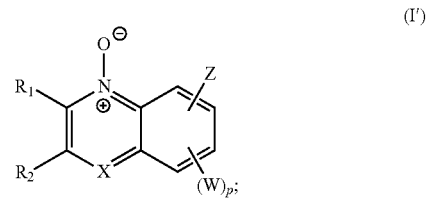

(I')

a pharmaceutical composition comprising the combination product; and methods of treating bacterial or fungal infections using the combination product and pharmaceutical composition.

6 Claims, No Drawings

(56) References Cited

OTHER PUBLICATIONS

Cheng, G., et al., "Quinoxaline 1,4-di-*N*-Oxides: Biological Activities and Mechanisms of Actions," Fronties in Pharmacology, vol. 7, Article 64, Mar. 21, 2016, pp. 1-21.

Chowdhury, G., et al., "DNA Strand Cleavage by the Phenazine Di-*N*-oxide Natural Product Myxin under Both Aerobic and Anaerobic Conditions," Chemical Research in Toxicology, vol. 25, Issue 1, Nov. 15, 2011, pp. 197-206.

Laursen, J.B., et al., "Phenazine Natural Products: Biosynthesis, Synthetic Analogues, and Biological Activity," Chemical Reviews, vol. 104, Issue 3, Mar. 1, 2004, pp. 1663-1685.

Lavaggi, M.L., et al., "Structural modifications on the phenazine *N,N'*-dioxide-scaffold looking for new selective hypoxic cytotoxins," European Journal of Medicinal Chemistry, vol. 45, Issue 11, Sep. 16, 2010, pp. 5362-5369.

Chen, F., et al., "Dehydrogenative N-Incorporation : A Direct Approach to Quinoxaline *N*-Oxides under Mild Conditions," Angewandte Chemie International Edition, vol. 53 (Epub 2014), Aug. 5, 2014, pp. 1-6.

Gómez-Caro, L., et al., "Synthesis of Quinoxaline 1,4-DI-*N*-Oxide Derivatives on Solid Support Using Room Temperature and Microwave-Assisted Solvent-Free Procedures," Quimica Nova, vol. 34, Issue 7, Apr. 15, 2011, pp. 1147-1151.

\* cited by examiner

SUBSTITUTED PHENAZINES AND METHODS OF TREATING CANCER AND BACTERIAL DISEASES

BACKGROUND OF THE INVENTION

The present invention relates to novel ionophores comprising N-oxide functionalized heterocycles, methods for their preparation and their medical use, in particular as anti-neoplastic and anti-infective agents. In particular, it relates to such compounds having enhanced membrane penetration.

Acute myeloid leukaemia (AML) is a hematopoietic stem cell disorder that causes excessive proliferation and rapid accumulation of myeloid precursor cells in the bone marrow. If left untreated, death occurs within weeks or months after diagnosis. AML is a heterogeneous disease. In the sub-group of pro-myelocytic leukaemia (PML) with a specific chromosome translocation fusing the genes for the PML and RAR proteins, retinoic acid based differentiation therapy, in combination with an anthracycline drug, and sometimes the differentiation enhancer arsenic trioxide, has proven successful (Fenaux et al, Blood 94 (4), 1192 (1999). Improved therapy has also become available for patients with myelodysplastic syndrome, which eventually develops to aggressive AML. Their disease progression can be halted by drugs targeting DNA methylation and cytosine metabolism, namely 5-aza-cytidine (Vidaza) and 5-aza-2'-deoxycytidine (Dacogen). These chemically simple substances are, in spite of their limited effects on AML overall, presently the two most profitable AML drugs (Global Data, Pharma e-Track 2013). Sadly, for most AML patients, AML chemotherapy has not made significant progress in the last 10-15 years. It is still a 30 year old drug regime based on an anthracycline (Daunorubicin (DNR) or idarubicin) supplemented by ara-binoside-C (ara-C) (Burnett et al, J Clin Oncol 29 (5), 487 (2011) and F. Ferrara et al, Lancet 381 (9865), 484 (2013)). Presently, complete remission is reached in 30-40% of AML patients less than 60 years old, and less than 10% in patients older than 70 years (Mehta 2010). However, relapse risk is in the range of 45-50% in older patients, making AML the leading cause of death due to leukaemia with a 5-year relative survival below 20%. Intensive chemotherapy is often severe with lethal side-effects, such as lesions in hematopoietic tissue, particularly the bone marrow, as well as the intestine and the heart (Joel et al, A. Rohatiner, in Leukaemia, edited by E. D. Henderson, T. A. Lister, and M. F. Greaves (Saunders, Philadelphia, 2002), pp. 394). There is thus a need for novel compounds that selectively target leukaemia blasts, and leave normal tissues and cells largely unaffected. Drugs based on disease-related molecular alterations in AML cells have so far been disappointing. An example is patients whose AML cells constitutively express active Flt-3 tyrosine kinase, who benefit little from Flt-3 inhibitors. Thus, there is a major clinical need for new drugs in leukaemia therapy.

Infectious diseases are a leading cause of death worldwide and account for more than 13 million deaths annually including nearly two-thirds of all childhood mortality at less than 5 years of age. There is serious concern regarding new and re-emerging infectious diseases, in which effective therapies are lacking (World Health Organization reports 1999, 2012 and 2014). Antimicrobial resistance is escalating and affects a very broad range of human diseases including pneumoniae, sepsis, tuberculosis, cholera, malaria, and AIDS. Of particular concern is the number of human pathogens developing multidrug resistance to conventional antibiotics and it is estimated that the burden of resistance will surpass that of e.g. cervical cancer (de Kraker M E A. et al, PLoS Med. 2011; e1001104). Historically, multidrug resistant bacteria, hereinafter MDR bacteria, emerges against nearly all classes of antibiotic agents (hereinafter AB agents) being introduced to the market, e.g. as described by Clatworthy et al, in Nat. Chem. Biol. (2007) 3, 541-548. This has led to a serious global crisis, since, for example, hospitals are being hampered by MDR strains, complicating routine surgery and other daily vital activities in hospitals. This dramatic situation has led to red alerts globally, e.g. as described by J. O'Neill et al in the report "Tackling Drug-Resistant Infections Globally: final report and recommendations, May 2016, http://amr-review.org/Publications.

In spite of the growing need for new AB agents, the pharmaceutical industry is reluctant, partly because of the rapid development of resistance to new products introduced into the market, and probability of reduced sales of this class of drugs. Thus, only two genuinely new classes of AB have been introduced to the market during the last 30 years, e.g. as described by Fair et al, Perspect. Medicin. Chem (2014) 6, 25-64 or Lewis et al, Nat. Rev. Drug. Discov. (2013), 12, 371-387. Most of the agents discovered and introduced to the market have been produced by micro-organisms themselves as agents of microbial warfare between species. In the golden era in the 60 years after the discovery of penicillin by Alexander Fleming in 1929, only 3 classes of AB agents were based on chemical design, the sulfonamides, quinolones and oxazolidinones.

The introduction of new, more potent derivatives of existing antibiotics provides only temporary solutions, since existing resistance mechanisms rapidly adapt to accommodate the new derivatives (Theuretzbacher U. Curr. Opin. Pharmacol. 2011:11:433-438). Although resistant Gram-positive bacteria pose a significant threat, the emergence of multidrug resistant (MDR) strains of common Gram-negative pathogens such as Escherichia coli are of special concern. Pan-resistance or extreme drug resistance are now commonly used terms to describe clinically important isolates of Pseudomonas aeruginosa, Acinetobacter baumannii and Enterobacteriaceae that are resistant to virtually all antibiotics (Patel et al, Front. Microbiol. 2013:4:48). Unfortunately, there are few, if any, antimicrobial agents effective against Gram-negative bacteria either in or entering phase 1 clinical trial that will address this critical need (Butler M S. et al, J. Antibiotics 2013:66:571-591).

Probably the most important antibiotic resistance mechanisms in terms of distribution and clinical relevance are β-lactamases (Bush K. et al, Annu. Rev. Microbiol. 2011: 65:455-478). The β-lactamases are enzymes that hydrolyse β-lactam antibiotics compromising the efficacies of ß-lactams our largest group and mainstay of antimicrobial chemotherapy for >70 years. Clearly, there is a need for inhibitors directed against these classes of enzymes that will restore the activity of their substrates—antibiotics that are cheap, non-toxic and normally effective. Serine β-lactamase inhibitors (clavulanic acid, sulbactam and tazobactam) have been a phenomenal success in extending the therapeutic life of β-lactam antibiotics and are also employed as diagnostic tools in clinical microbiological laboratories worldwide. In contrast, there is no clinical inhibitor available for metallo-β-lactamases (MBLs; Drawz et al., Antimicrob. Agents Chemother. 2014:58:1835-1846). The latter has now become one of the most clinically important families of β-lactamases showing global dissemination.

An unsolved medical problem, particularly relevant to AML patients, and which is well described in the prior art is that cancer patients often suffer from life-threatening infections due to an impaired immune system (see e.g. Zhang et al, in Diagnostic Microbiology and Infectious Disease 88 (2017) 247-251). Therefore, cancer patients regularly receive antibiotic therapy in combination with anti-cancer therapy.

N-heterocyclic aromatic compounds are rarely found in nature, although often these exert potent biological abilities to inhibit growth of tumours, and to inhibit bacterial and fungal growth (Org. Lett. 2016, 18, 2495-2498). Scheme 1 exemplifies certain heterocyclic compounds known in the prior art as anti-neoplastic and anti-infective agents. Iodinin (1) has been known for almost a centennial, and is a member of the phenazine family. It is a planar nitrogen-containing heterocyclic compound produced by a variety of bacteria. Iodinin is an oxidized phenazine, namely 1,6-dihydroxyphenazine 5,10-dioxide. The related compound myxin (2) was discovered in 1966 by isolation from myxobacteria of the type Sorangium cellulosum which is a Gram-negative bacterium, as described by Peterson et al in Canadian Journal of Microbiology (1966), 12(2), 221-30. The bacteria were shown to produce myxin as a potent antibiotic capable of inhibiting growth of a wide variety of microorganisms including gram-positive and and gram-negative bacteria, fungi, actinomycetes, and yeasts. As described by e.g. Weigele et al in *Antimicrobial Agents and Chemotherapy* (1970), 46-49 and Grunberg et al, *Chemotherapia* (1967), 12, 272-281, myxin has been described in the prior art as an agent active against a number of Gram-positive and Gram-negative bacteria, fungi and parasites, e.g. *Streptococcus agalactiae, Streptococcus pyogenes, Diplococcus pneumoniae, Staphylococcus aureus, Escherichia coli, Klebsiella pneumoniae, Proteus vilgaris, Pseudomonas aeruginosa, Salmonella typhi, Salmonella schottmuelleri, Pasteurella multocida, Erysiphelothrix indisiosa, Mycobacterium tuberculosis, Candida albicans, Trichophyton mentagrophytes, Microsporum audouini, Ustilago Zeaa, Fusarium oxysporum, Bortrytis paeoniae, Aspergillus flavus, Aspergillys niger, Trichomonas vaginalis, Trichomonas foetus, Hymenolepis nana* (adults), *Mycobacterium bovis, Microsporum canis*.

Scheme 1

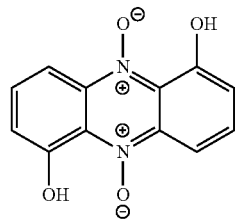

(1)

Iodinin

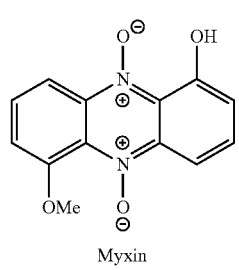

(2)

Myxin

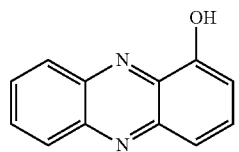

(3)

1-Hydroxyphenazine, or hemi-pycocyanine

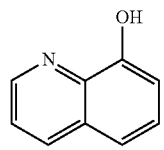

(4, oxine)

8-hydroxy-quinoline

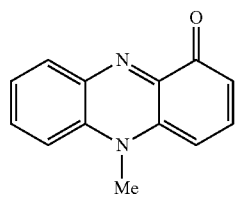

(5)

Pyocyanine

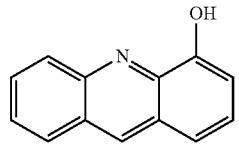

(6)

4-Hydroxyacridine

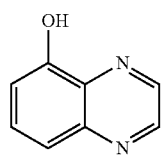

(7)

5-Hydroxy-quinoxaline

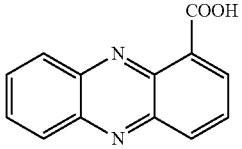

(8)

1-Carboxyphenazine

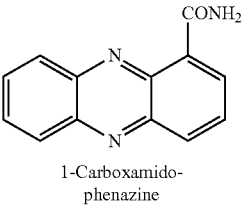

(9)

1-Carboxamido-phenazine

-continued

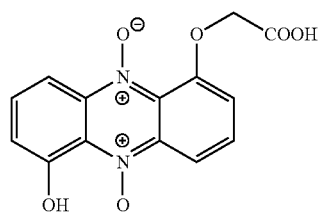

1-Carboxymethyl-iodinin (10)

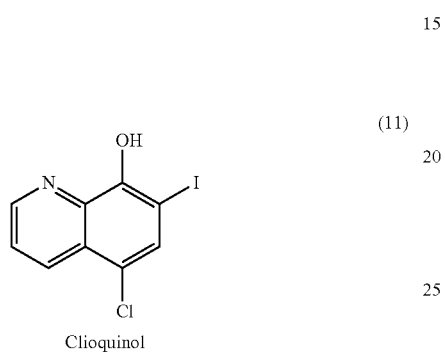

Clioquinol (11)

1-Hydroxyphenazine, or hemi-pyocyanine (3) and pyocyanine (5) were discovered in 1864 and the structures elucidated in the years 1920-1928 as described by Wrede et al in *Z. physiol. Chem.* (1928), 177, 177-86. They are produced by *Pseudomonas* pyocyaneus and *Pseudomonas aeruginosa* as described later by Ikura et al in Hakko Kogaku Zasshi, (1973), 51(11), 840-2. *Pseudomonas aeruginosa* also produces phenazine-1-carboxylic acid (8) and phenazine-1-carboxamide (9) as described by Jimenez et al in Microbiol. Mol. Biol. Rev. 76, 46-65. 4-Hydroxy-acridine (6) was isolated in 1914 as a synthetic by-product as described by Kliegl et al in Berichte der Deutschen Chemischen Gesellschaft (1914), 47, 1629-40. Oxine (10) was described as a potent antibicrobial agent, especially as its cupric complex, as described by Leimgruber et al in Ger. Offen. (1970), DE 1931466 A 19700102. The antibacterial properties of the natural product 5-hydroxy-quinoxaline (7) has been known since the beginning of the 20$^{th}$ century, and it is shown that its antibacterial activity is related to its metal-binding ability, as described by Freeman et al in Journal of Organic Chemistry (1951), 16, 438-42 42 and by Creanor et al in Biochem. J. (1975), 147, 401-410. Its N,N-dioxide has been described as an antibacterial agent in U.S. Pat. No. 3,479,354A. The antibacterial activity of carboxymethyl-iodinin/myxin (10) has been well described by Weigele et al in *Antimicrobial Agents and Chemotherapy* (1971) 46-9. Clioquinol (11) is an antifungal and antiprotozoal drug used to cure skin infections.

The mechanism for the biological effects of many of these substances is often related to their ability to bind metal ions. Metal binders have a long history of a number of biological and therapeutic uses, e.g. against micro-organisms or cancer. Heterocyclic amino-hydroxy derivatives or amino-keto derivatives as exemplified in scheme 1 have metal binding properties (scheme 2), and this is shown in the prior art to be related to their biological activity.

Scheme 2

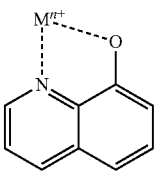
I

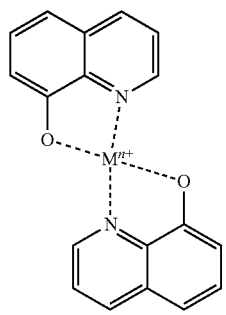
II

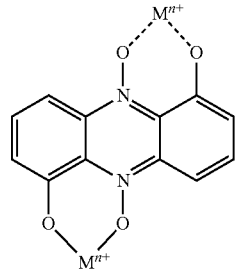
III

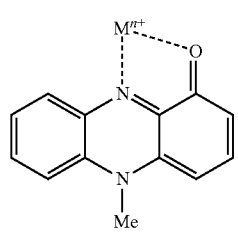
IV

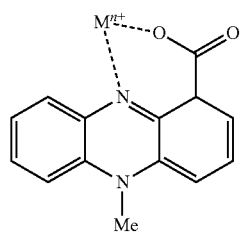
V

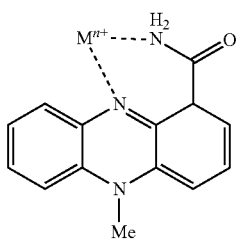
VI

The common binding moiety in the examples in Scheme 1 is related to the ability of the heterocyclic N-atom or its N-oxide functionality to bind metal ions together with the neighbouring functional group, as e.g. an O-atom, as shown in Scheme 2. For example, oxine or 8-hydroxy-quinoline (4) is a binder of $Zn^{2+}$ and $Cu^{2+}$ as described by Prachayasittikul et al, *Drug design, development and therapy* (2013), 7, 1157-78. 1-Hydroxy-phenazine (3) has a binding ability for $Zn^{2+}$ and $Cu^{2+}$ as described by Inagaki et al, *Chemical & Pharmaceutical Bulletin* (1976), 24(5), 839-44. Myxin (2) has been used in the form of a myxin-copper (II) complex (Cuprimyxin) as an antibacterial drug as described by Leimgruber et al in Ger. Offen. (1970), DE 1931466 A 19700102.

A metal binding compound may be classified as a metal chelator, metal shuttle, or metal ionophore dependent on the behavior of the compound in a biological system when the concentration of a given metal ion is increased, as described by Ding and Lind in IUBMB Life (2009) 61, 1013-1018. A given compound may have a specific biological effect. If increasing metal concentrations reverse the biological effect of the compound, it is classified as a "metal chelator". If the compound complexed with the metal ions enters the cell without changes in biological activity, the compound may be classified as a "metal shuttle". The metal shuttle may exhibit biological activity because the metal dissociates from the complex, or because the compound itself is biochemically active. If the biological effect of the compound is amplified by increasing the metal concentration, it is classified as a "metal ionophore" having the ability to transport metal ions between intracellular and extracellular spaces. The moiety comprising the aromatic hydroxy group combined with the aromatic nitrogen atom in clioquinol (11) is shown by Ding and Lind in IUBMB Life (2009) 61(11): 1013-1018 to have ionophore activity.

The biological properties of the phenazine class of natural products include antibiotic, antitumor, antimalaria, antiparasitic and anti-Alzheimer activities. The physiological function leading to these activities can be inhibition/control of DNA, RNA, and protein synthesis as well as disruption of energy requiring membrane-associated metabolic processes. The planar, aromatic iodinin core has structural similarities to known intercalators, e.g. anthracyclines like daunorubicin, and thus it is anticipated that the phenazines acts as DNA intercalating agents.

However, the anthracyclines have a serious disadvantage: they are cardiotoxic at clinical doses, and it is well documented in the prior art that patients experience irreversible cardiac side effects after therapy with anthracyclines. As an example, daunorubicin is still the golden standard in the treatment of AML in the clinic. This is a major problem, especially when treating children and adolescents with AML. The heart failure manifests itself by impairment of cardiac output and contractility. As described by Tan et al. in Cancer 20(3): 333-53 and by Ichikawa et al. in PLoS ONE, 2017, Vol. 12(5): 1-18, it has been documented that changes in the heart can be observed after treatment with daunorubicin at doses as low as 3 mg/kg. In Norway, for example, daunorubicin is used at single doses of 0.5-3 mg/kg in the treatment of AML. This means that the therapeutic window (TW) is very narrow or non-existent. This is an unsolved medical challenge.

It has been shown that iodinin (1) has much lower cardiac toxicity than the anthracyclines, e.g. as described by Myhren et al in Marine drugs 11 (2), 332 (2013). The interaction between phenazines and DNA was shown by differences in the comparison between the UV/visible spectrum of a phenazine in the presence of GC and AT-rich double-stranded oligonucleotides, and the spectrum of pure phenazine. Although no binding to single-stranded DNA was observed, the binding with double-stranded DNA occurred with strong association constants, in the $10^{-4}$-$10^{-6}$ $M^{-1}$ range, comparable to those of ethidium bromide (Hollstein U et al. Biochem 10 (3): 1971; 497-504). The use of iodinin and myxin against cancer is only briefly reported in the prior art. One study reported low activity against a mouse sarcoma model (Endo et al, Tohoku University. Ser. C, Medicine 14 (3), 169 (1967). Iodinin has a number of biological effects. In U.S. Pat. No. 3,764,679 iodinin is claimed to have antihypertensive effects.

The compounds exemplified in Scheme 1 can be obtained in different ways, the first and the most widespread is by bacterial production. For example, the first iodinin-producing bacterium, a terrestrial bacteria, *Chromobacterium iodinum* (later re-classified as *Brevibacterium iodinum*) was named owing to the purple, bronze-glinting pigment which covers its colonies on suitable solid media (McIlwain H, *Biochem. J.* 1943). This pigment, the iodinin, was found to inhibit the growth of certain other bacteria. Iodinin is also produced by *Pseudomonas phenazinium* (Byng G S et al, J. Gen. Microbiol. 97: 1976; 57-62) when grown on a variety of carbon sources, especially L-threonine. A second carbon growth dependant is the biosynthesis by *Brevibacterium iodinum* (Gerber N N et al, *Biochem.* 6(9): 1967; 2701-2705). The highest yield of iodinin production occurred in experiments with resting cells in the presence of some three-, four-, or five-carbon amino acids. Tricarboxylic acid cycle compounds, especially succinic acid, also gave high yields. Another biosynthesis by *Arthrobacter paraffineus* KY 7134 (Suzuki T et al, *Agr. Biol. Chem.* 35(1): 1971; 92-98), on n-paraffin as the only source of carbon, produced two sorts of crystalline pigments in the culture medium, one yellow and one deep-red, corresponding respectively to 1,6-dihydroxyphenazine (iodinin intermediate) and 1,6-dihydroxyphenazine 5,10-dioxide (iodinin). Microorganisms forming a novel group of Nocardiaceae were seen to produce slants with lustrous coppery needles on the mycelium and in the agar, characteristic of iodinin crystals (Gerber N N., 1966; 5(12): 3824-3829). Another production of iodinin, as a culture metabolite, is also possible after growth of *Acidithiobacillus ferrooxidans* on elemental sulfur (Ceskova P et al. *Folia Microbial.* 47(1):2002; 78-80).

Iodinin can also be obtained through fungal production. Iodinin was isolated from a soil sample, *Nocardiopsis dassonvillei* (*N. syringae, N. mutabilis* and *N. atra*), an alkalophilic actinomycete, strain OPC-15, that produced different phenazine antibiotics under different culture conditions, including iodinin (Tsujibo H et al. *Agric. Biol. Chem.* 52(2): 1982; 301-306). Other Actinomycetes, e.g. *Microbispora amethystogenes* and *parva, streptosporangium album* and *amethystogenes*, realize extracellular production of characteristic iodinin violet crystal (pigment) in oat-meal agar medium (Tanabe I et al. *J. Ferment. Bioeng.* 79 (4): 1995; 384-386). An efficient method could be fungal metabolite screening, showing the production of many mycotoxins and fungal metabolites, possibly containing iodinin (Nielsen K F. *Journal of Chromatography A* 1002: 2003; 111-136).

Iodinin (1) is also found as a bioactive metabolite in marine biological resources. As the bioprospecting for marine compounds is expanding, it has been discovered that some marine Actinomycetes bacterium and marine *Actinomadura* sp. are proven to be the best, offering a great biological diversity and therefore a great chemical diversity. Other microorganisms like *Microbispora aerata, Pseudomonas iodina*, and *Streptomyces thioluteus* are capable of synthesizing 1,6-dihydroxyphenazine-5-oxide, an intermediate of the iodinin biosynthesis (Gerber N N et al. *Biochem* 4 (1): 1965; 176-180).

Regarding their availability through synthetic organic chemistry, the procedures in the prior art are not applicable as methods for the synthesis of larger amounts for use in drug discovery projects. In US 2009/042894 a biotechnological procedure is suggested to produce iodinin. In DE 2016467, DE 2115660, U.S. Pat. Nos. 3,929,790, 3,937,707, WO 2008/089283, and in Alonso et al, *Chem. Comm.* 41, 2004, 412-413, methods to alkylate phenazines structurally related to iodinin and myxin are described. However, the functional groups introduced are alkyl groups, rendering the derivatives less water soluble than the parent compounds. There is no discussion of any improvement, for example in solubility for injection media.

GB 1285314 A, GB 1325142 A and GB 1285010 A (Hoffman La Roche) and WO 2008/089283 (J. Pharma Inc.) describe derivatives of iodinin for treating bacterial infections. However, as evident from the general formulas and the experimental procedures in these documents, the resulting compounds are not soluble in injection media, and therefore do not solve the basic solubility problem. Further, these documents use as the starting material iodinin from natural sources. As such, these methods would be a tedious procedure for large scale preparation of material for drug development.

Thus, in spite of their promising biological effects, the heterocyclic amines exemplified in Scheme 1 have several major disadvantages:
a) As for iodinin (1), they often have low solubility in fluids suitable for biological testing, e.g. for intravenous injection. For example, iodinin (1) is practically insoluble in all solvents.
b) Some of them can only be obtained by bioprospecting, which is laborious and expensive yielding only milligram quantities of the substance at a high cost and the process is time-consuming.
c) They often have a non-selective biodistribution in vivo and lack the chemical functionality required to attach functional groups for regulating their biodistribution, e.g. through vectors like peptides or monoclonal antibodies, and physiological properties such as lipophilicity and solubility.
d) Many of them lack the N-oxide functionality seen for iodinin (1), myxin (2), 8-hydroxy-quinoxaline (7) and carboxymethyl iodinin (10) that according to the cited literature herein lead to their strong anti-cancer activity.

The problem relating to solubility in fluids suitable for biological testing, e.g. for intravenous injection, may be related to the lack of functional groups increasing their solubility, and at the same time maintaining their biological activities. We now propose that this problem can be addressed by introducing suitable functionalities at the —OH, —COOH, —CONH$_2$ or —OCH$_2$COOH groups in the structures exemplified in Scheme 1. This has been found to regulate their physico-chemical properties whilst also regenerating the original functional groups by biotransformation. Surprisingly, this has led to the finding that the molecules have enhanced membrane penetration.

Specifically, we now propose alternative compounds that possess one or more of the following properties:
a) one or more functional groups that render the compounds more soluble in injection media and keep the toxicity at an acceptable level, but at the same time have general lipophilicity rendering them more penetrable over cell membranes,
b) the compounds can be obtained in larger amounts via synthesis,
c) the chemical modification of the respective ionophore depicted above allows for attachment of targeting vectors giving more selective effects on the targets for therapy, and
d) in light of the strong biological effect of N-oxidized poly-heterocyclic compounds, the proposed compounds are ionophores with enhanced membrane penetration that regenerate the parent compounds to exert their toxic effects on the cells or microorganisms of interest after administration to the organism of interest.

In WO 98/27969, the bis-N-oxides of derivatives of 1-hydroxy-phenazine (3) are described as new antibacterial agents. However, no description of attachment of functional groups to regulate their toxicity, physico-chemical properties or biological selectivity is provided. In WO 2015/100331, derivatives of 1-hydroxy-phenazine (3) are described as potentially improved antibacterial agents. In Antimicrobial Agents and Chemotherapy (1970), 10, 46-9, Weigele et al discuss antimicrobial agents structurally related to myxin, describing different alkyl, ester and amide derivatives of iodinin and myxin. However, the desired targets are not cleavable precursors of ionophores with enhanced membrane penetration.

More specifically, it has been found that the ionophores described herein which have enhanced membrane penetration are particularly attractive since they through their biodistribution can be adapted with respect to physicochemical properties such as solubility, lipophilicity and stability, and biological properties such as membrane permeability and toxicity, residence time in the blood and selectivity through targeting using peptides or proteins such as monoclonal antibodies. Starting materials for the preparation of the compounds, such as iodinin (1), myxin (2) and carboxymethyl-iodinin (10), can be conveniently prepared in large scale as described earlier by Doskeland et al in WO 2015/063516.

BRIEF SUMMARY OF THE INVENTION

Deficiencies in the prior art related to the therapy of AML in combination with serious infectious diseases in the same patient group presents a clearly defined medical need. It has now surprisingly been found that new phenazine derivatives with improved physico-chemical properties and pharmacokinetics, possessing both anti-cancer and anti-bacterial activity, can meet this medical need. As will be described herein, the phenazine derivatives also have broader application as anti-neoplastic and/or anti-infective agents.

DETAILED DESCRIPTION OF THE INVENTION

In one aspect the invention provides a compound of general formula (I'), or a pharmaceutically acceptable salt thereof:

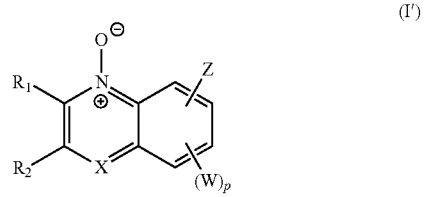

wherein:

X is an N-oxide functionality (N+—O−), or CH;

Z is a group susceptible to hydrolytic and/or enzymatic cleavage in vivo to form a group selected from —OH, —COOH, —CONH$_2$, —O-Q-COOH and —O-Q-CONH$_2$ (where Q is a straight chained or branched alkylene group, preferably C$_{1-3}$ alkylene, e.g. methylene), and Z is optionally linked to one or more targeting groups;

R$_1$ and R$_2$ are independently selected from hydrogen, lower alkyl (e.g. C$_{1-6}$ alkyl), halogen (e.g. F, Cl, Br, I), an acidic group which is —COOH, —SO$_3$H, —PO$_3$H$_2$ or —B(OH)$_2$; and an aryl group (e.g. phenyl); or R$_1$ and R$_2$, together with the intervening carbon atoms, form an optionally substituted aromatic group;

each W is independently selected from lower alkyl (e.g. C$_{1-6}$ alkyl), halogen (e.g. F, Cl, Br, I), OH, and an acidic group which is —COOH, —SO$_3$H, —PO$_3$H$_2$ or —B(OH)$_2$; and p is an integer from 0 to 3, preferably 0 or 1, e.g. 0.

In a further aspect the invention provides a compound of general formula (I), or a pharmaceutically acceptable salt thereof:

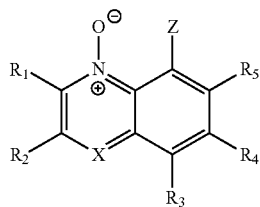

(I)

wherein:

X is an N-oxide functionality (N+—O−), or CH;

Z is a group susceptible to hydrolytic and/or enzymatic cleavage in vivo to form a group selected from —OH, —COOH, —CONH$_2$, —O-Q-COOH and —O-Q-CONH$_2$ (where Q is a straight chained or branched alkylene group, preferably C$_{1-3}$ alkylene, e.g. methylene), and Z is optionally linked to one or more targeting groups;

R$_1$ and R$_2$ are independently selected from hydrogen, lower alkyl (e.g. C$_{1-6}$ alkyl), halogen (e.g. F, Cl, Br, I), an acidic group which is —COOH, —SO$_3$H, —PO$_3$H$_2$ or —B(OH)$_2$; and an aryl group (e.g. phenyl); or R$_1$ and R$_2$, together with the intervening carbon atoms, form an optionally substituted aromatic group; and R$_3$, R$_4$ and R$_5$ are independently selected from hydrogen, lower alkyl (e.g. C$_{1-6}$ alkyl), halogen (e.g. F, Cl, Br, I), and an acidic group which is —COOH, —SO$_3$H, —PO$_3$H$_2$ or —B(OH)$_2$.

In a preferred embodiment X is an N-oxide functionality.

In a preferred embodiment Z is an organic group containing one or more ester, carbonate ester, or carbamate groups (including sterically hindered ester groups), which is optionally linked to one or more targeting groups. Typically Z may be an organic group containing 1 to 50 atoms, e.g. up to 30 atoms, e.g. up to 10 atoms.

Suitable Z groups include those having the formula: -T-A-Y in which:

T is a group selected from —O—, —NR$_9$—, —S—, —(C═O)—, —(CHR$_9$)— (where R$_9$ is —H or C$_{1-3}$ alkyl), —COU— and —SO$_2$U— (where U is —O—, —S—, —NR$_{10}$— or —CHR$_{10}$— in which R$_{10}$ is —H or C$_{1-3}$ alkyl);

A is —(C═O)—, lower alkylene (e.g. straight chained or branched C$_{1-6}$ alkylene), or an arylene group optionally substituted with one or more alkylamino (e.g. C$_{1-6}$ alkylamino) or alkoxy (e.g. C$_{1-6}$ alkoxy) groups; and Y is a hydrophilic monomeric, oligomeric or polymeric group comprising hydrogen bond donor and/or hydrogen bond acceptor atoms, for example selected from H, N, O, S and P, e.g. a hydrophilic group comprising one or more functional groups selected from —OH, —SH, —CO$_2$H, —SO$_3$H, —PO$_3$H$_2$, —B(OH)$_2$, and aliphatic or aromatic nitrogen-containing groups; or Y is any of the groups mentioned above linked to one or more targeting groups.

In certain embodiments Y is a group —NR$_{11}$R$_{12}$ in which R$_{11}$ and R$_{12}$ are independently selected from —H, lower alkyl (preferably C$_{1-6}$ alkyl, e.g. methyl or ethyl) and aryl, or R$_{11}$ and R$_{12}$ together form a 5- or 6-membered heterocyclic ring which may further comprise one or more (preferably one) —O—, —S—, or —NH— ring atoms, and wherein the heterocyclic ring may optionally be substituted by one or more lower alkyl (e.g. C$_{1-6}$ alkyl) or aryl (e.g. phenyl) groups.

In other embodiments, Y is a group —(CHR$_{13}$)—O—(C═O)—R$_{14}$ where R$_{13}$ is —H or C$_{1-3}$ alkyl, and R$_{14}$ is an aliphatic, aromatic or alicyclic group comprising 1-50 carbon atoms, for example lower alkyl (e.g. C$_{1-6}$ alkyl) or aryl.

In other embodiments, Y is a group —(CHR$_{15}$)—NR$_{16}$—COOR$_{17}$ where R$_{15}$ is —H or C$_{1-3}$ alkyl, and R$_{16}$ and R$_{17}$ are independently —H, lower alkyl (e.g. C$_{1-6}$ alkyl) or aryl.

When T is —O—, A is preferably —(C═O)—.

Examples of Z groups which may be present in any of the compounds herein described include the following:

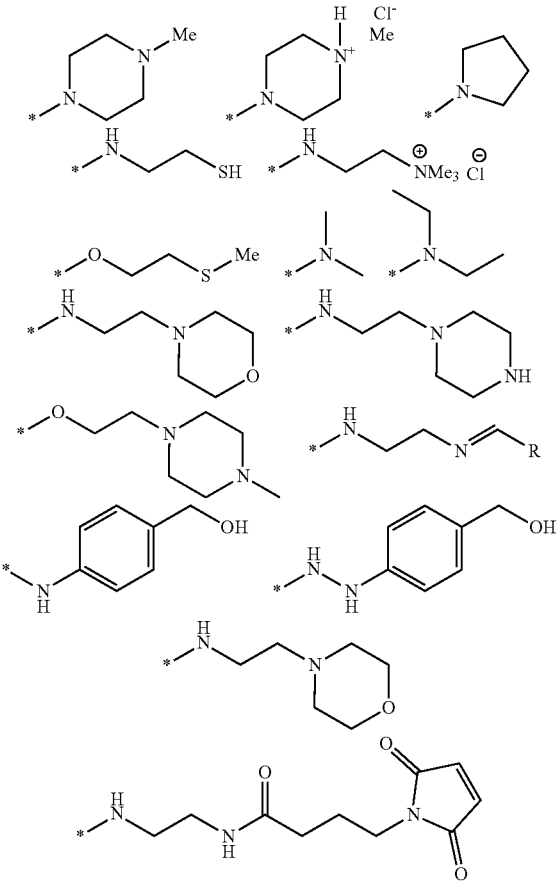

13

-continued

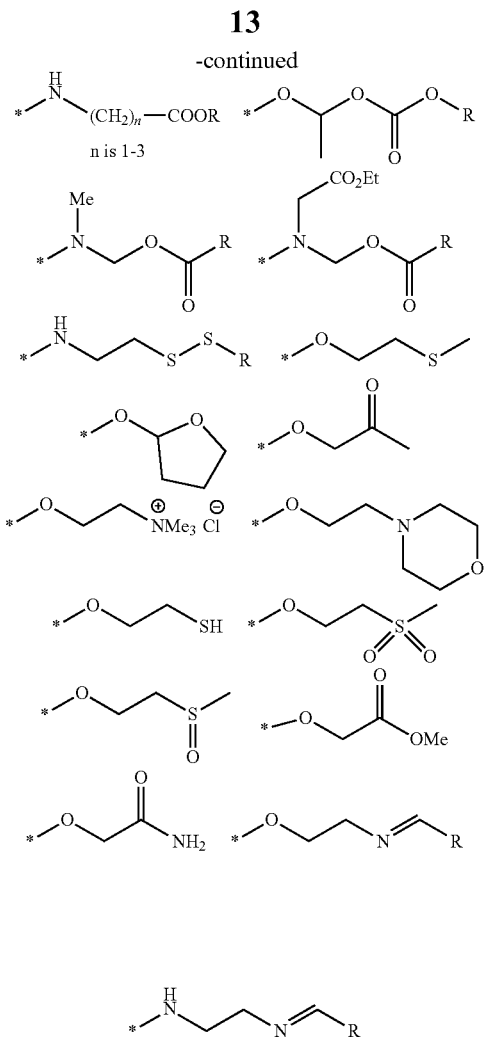

14

-continued

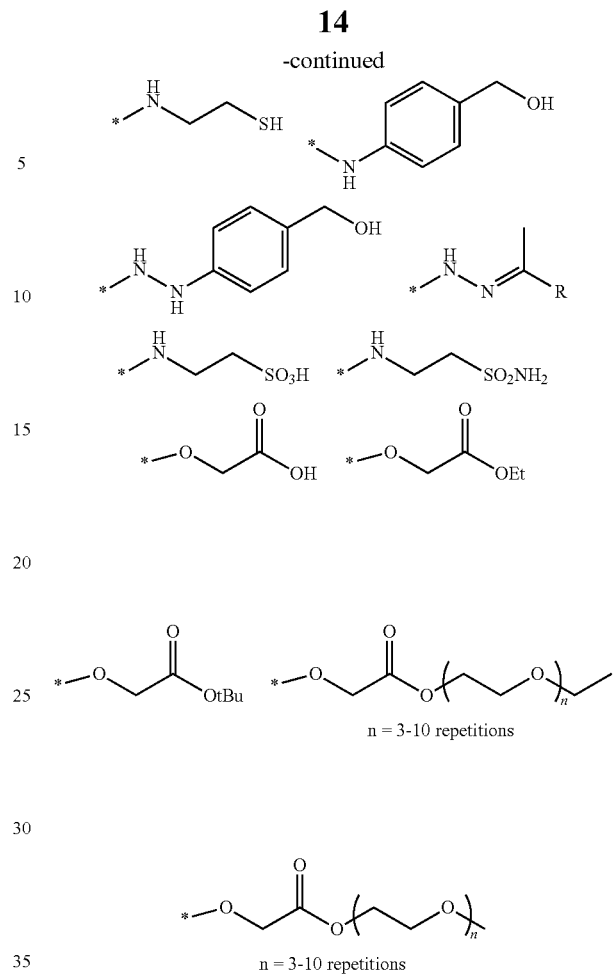

In which * denotes the point of attachment to the remainder of the molecule; and R is either -H or $C_{1-3}$ alkyl Compounds in accordance with the invention may include the structural units shown in the top panel in Scheme 3 in the case where the group Z is positioned in the 1-position of the phenazine scaffold. The same scheme is valid for any of the regioisomers herein disclosed where the Z group is positioned in the 2- or 3-position. The lower panel of this Scheme illustrates the products produced following hydrolytic or enzymatic cleavage in vivo:

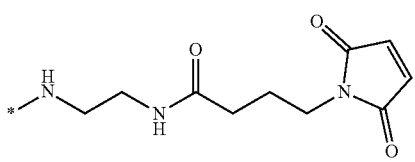

Scheme 3

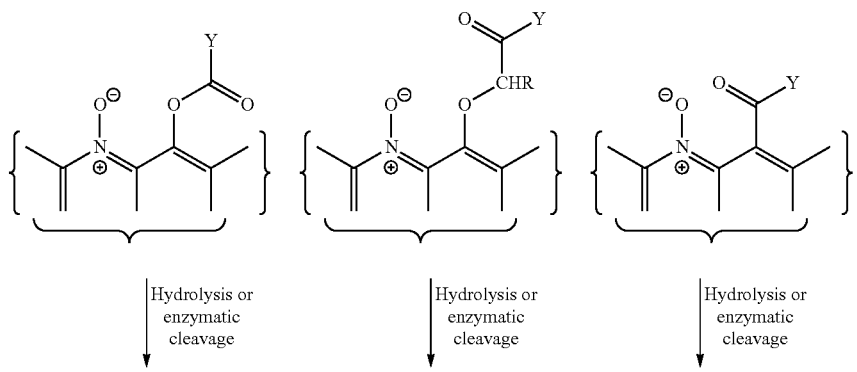

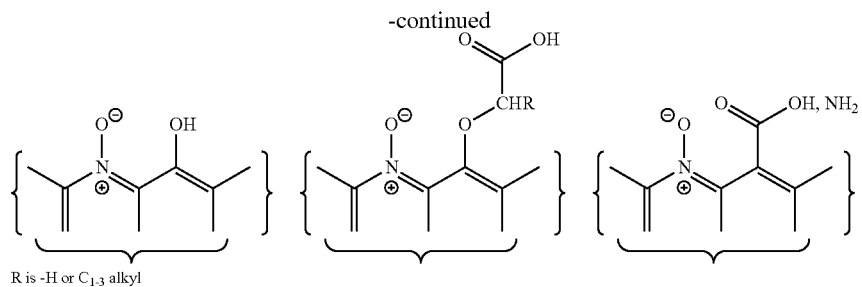

R is -H or $C_{1-3}$ alkyl

In one embodiment $R_1$ and $R_2$, together with the intervening carbon atoms, form an optionally substituted aromatic group. The aromatic group may comprise one or more aromatic rings. Where more than one ring is present these will typically be fused. Examples of aromatic rings which may be formed include optionally substituted phenyl and naphthyl rings. Where any substituents are present these may be selected from lower alkyl (e.g. $C_{1-6}$ alkyl), halogen (e.g. F, Cl, Br, I), and an acidic group which is —COOH, —$SO_3H$, —$PO_3H_2$ or —$B(OH)_2$.

Compounds in which $R_1$ and $R_2$ together form an optionally substituted phenyl ring include the following compounds of general formula (II') and their pharmaceutically acceptable salts:

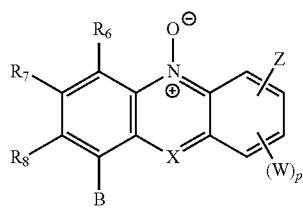

(II')

wherein X, Z, W and p are as defined herein;
$R_6$, $R_7$ and $R_8$ are independently selected from hydrogen, lower alkyl (e.g. $C_{1-6}$ alkyl), halogen (e.g. F, Cl, Br, I), and an acidic group which is —COOH, —$SO_3H$, —$PO_3H_2$ or —$B(OH)_2$:
$R_7$ and $R_8$ may also independently represent an aryl group (e.g. phenyl); and
B is either a group Z as herein defined, or may be selected from —H, —OH, —SH, —OR or —SR (wherein R is $C_{1-6}$ alkyl, preferably $C_{1-3}$ alkyl, e.g. methyl), and halogen (e.g. F, Cl, Br, I).

In one embodiment, compounds in which $R_1$ and $R_2$ together form an optionally substituted phenyl ring include the following compounds of general formula (II), and their pharmaceutically acceptable salts:

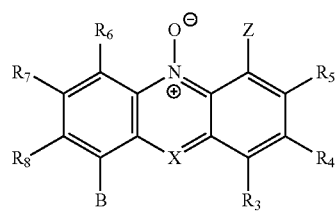

(II)

wherein X, Z, $R_3$, $R_4$ and $R_5$ are as defined herein;
$R_6$, $R_7$ and $R_8$ are independently selected from hydrogen, lower alkyl (e.g. $C_{1-6}$ alkyl), halogen (e.g. F, Cl, Br, I), and an acidic group which is —COOH, —$SO_3H$, —$PO_3H_2$ or —$B(OH)_2$;
$R_7$ and $R_8$ may also independently represent an aryl group (e.g. phenyl); and
B is either a group Z as herein defined, or may be selected from —H, —OH, —SH, —OR or —SR (wherein R is $C_{1-6}$ alkyl, preferably $C_{1-3}$ alkyl, e.g. methyl), and halogen (e.g. F, Cl, Br, I).

In formula (II') or formula (II), B is preferably selected from —H, —OH, —SH, —OR or —SR (wherein R is $C_{1-6}$ alkyl, preferably $C_{1-3}$ alkyl, e.g. methyl), and halogen (e.g. F, Cl, Br, I).

In one embodiment the invention relates to compounds of general formulae (IIIa) or (IIIb), or pharmaceutically acceptable salts thereof:

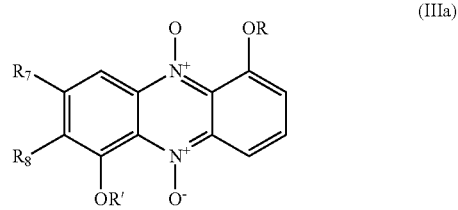

(IIIa)

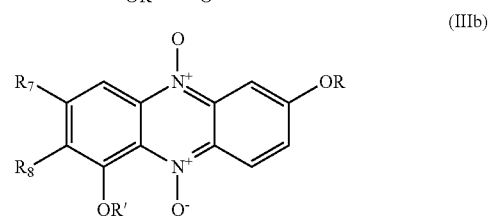

(IIIb)

wherein:
R is selected from any of the following groups:
—$(CH_2)_n$—CO—OR" (where n is an integer from 1 to 3, e.g. 1, and R" is either —H or $C_{1-6}$ alkyl);
—CO—OR" (where R" is either —H or $C_{1-6}$ alkyl);
—CO—($C_{1-6}$ alkyl); and
—CO—$NR_{11}R_{12}$ in which $R_{11}$ and $R_{12}$ are as hereinbefore defined;
R' either corresponds to group R or is selected from —H and $C_{1-6}$ alkyl (preferably $C_{1-3}$ alkyl, e.g. methyl); and
$R_7$ and $R_8$ are as hereinbefore defined.

In formula (IIIa) or formula (IIIb), R' is preferably —H or methyl.

In the case where either R or R' in formula (IIIa) or formula (IIIb) is a group —CO—$NR_{11}R_{12}$, $R_{11}$ and $R_{12}$ may independently be selected from —H and lower alkyl (e.g. $C_{1-6}$ alkyl), or $R_{11}$ and $R_{12}$ together may form a 5- or 6-membered heterocyclic ring which may further comprise an additional —NH— group, and wherein the heterocyclic ring may optionally be substituted by one or more lower alkyl groups (e.g. $C_{1-6}$ alkyl, preferably methyl). Examples of suitable heterocyclic rings include piperazine, N-methyl piperazine and pyrrolidine.

In one embodiment of formula (IIIa) or (IIIb), $R_{11}$ and $R_{12}$ may both be —H.

In formula (IIIa) or (IIIb), $R_7$ and $R_8$ are preferably independently selected from H, F, Cl, Br, $C_{1-3}$ alkyl and phenyl, more preferably from H, F, Cl, Br, and $C_{1-3}$ alkyl.

Preferred examples of compounds of formula (IIIa) include the following:

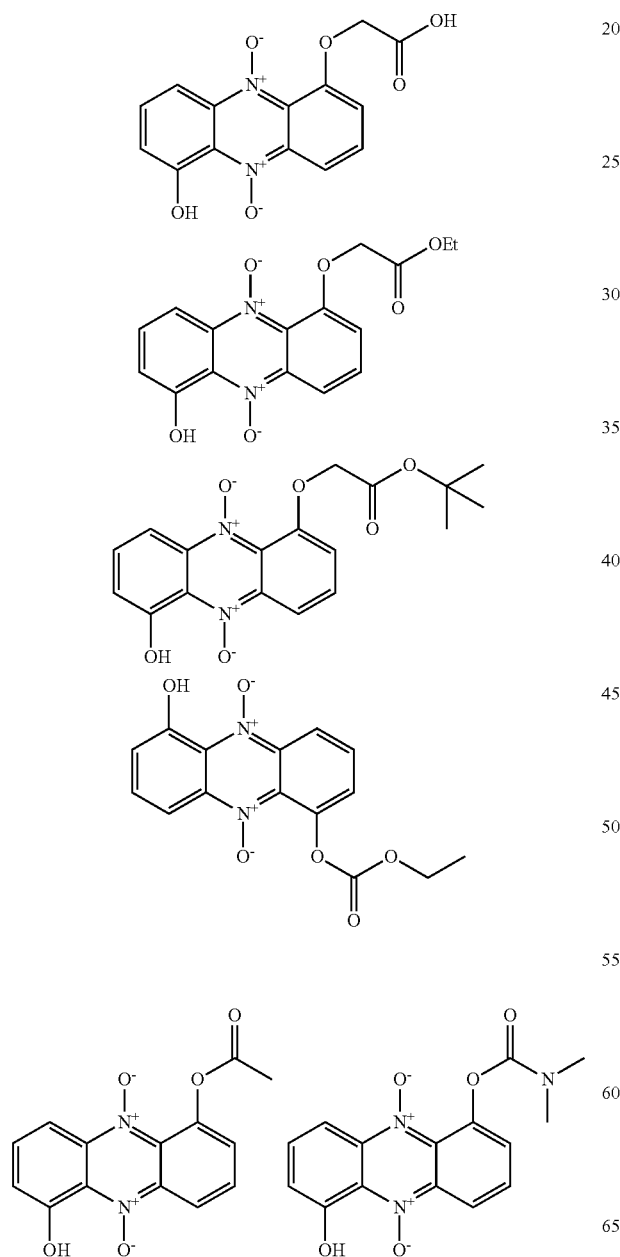
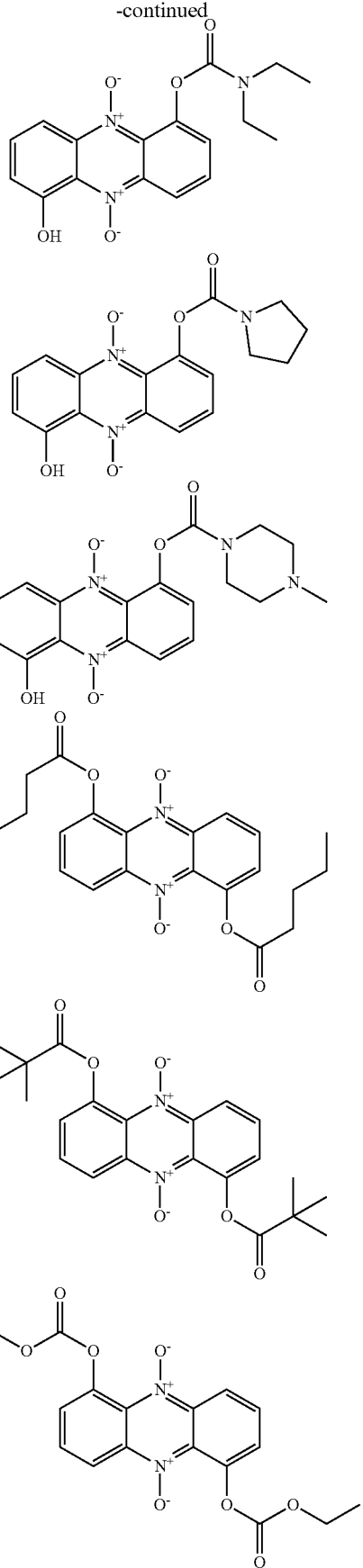

-continued

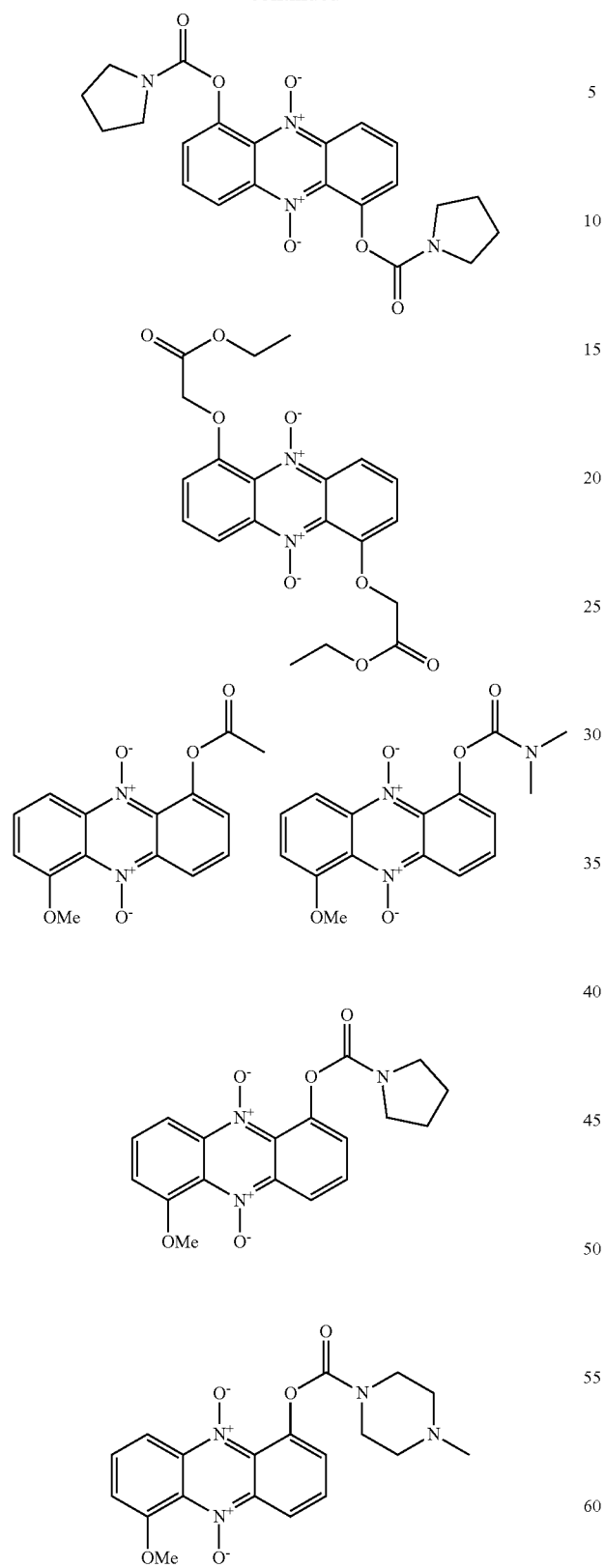

In another embodiment the invention relates to compounds of general formula (IV') and their pharmaceutically acceptable salts:

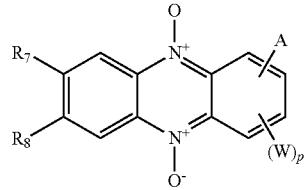

wherein:
A is either —OR or —NR$_{18}$R$_{19}$;
R is selected from any of the following groups:
- —(CH$_2$), —CO—OR" (where n is an integer from 1 to 3, e.g. 1, and R" is either —H or C$_{1-6}$ alkyl);
- —CO—OR" (where R" is either —H or C$_{1-6}$ alkyl);
- —CO—(C$_{1-6}$ alkyl);
- —CO—NR$_{11}$R$_{12}$ in which R$_{11}$ and R$_{12}$ are as hereinbefore defined;
- —(CH$_2$)$_n$—CO—NR$_{11}$R$_{12}$ in which R$_{11}$ and R$_{12}$ are as hereinbefore defined;
- —CO—O—CH$_2$—C≡CH;
- —CS—NR"$_2$ (where each R" is either —H or C$_{1-6}$ alkyl);

R$_{18}$ is H or C$_{1-3}$ alkyl;
R$_{19}$ is selected from any of the following groups:
- —COCF$_3$;
- —CO—O—(CH$_2$)$_n$—NR$_{11}$R$_{12}$ (where n is an integer from 1 to 3, e.g. 1 or 2, and R$_{11}$ and R$_{12}$ are as hereinbefore defined);

or R$_{18}$ and R$_{19}$ together may form a 5- or 6-membered heterocyclic ring which may further comprise one or more (preferably one) —O—, —S—, or —NH— ring atoms, and wherein the heterocyclic ring may optionally be substituted by one or more lower alkyl (e.g. C$_{1-6}$ alkyl) or —CO—C$_{1-6}$ alkyl groups;

or —NR$_{18}$R$_{19}$ represents a group —N=CH—NR"$_2$ (where each R" is either —H or C$_{1-6}$ alkyl); each W is independently selected from lower alkyl (e.g. C$_{1-6}$ alkyl), halogen (e.g. F, Cl, Br, I), OH, and an acidic group which is —COOH, —SO$_3$H, —PO$_3$H$_2$ or —B(OH)$_2$;

p is an integer from 0 to 3, preferably 0 or 1, e.g. 0; and
R$_7$ and R$_8$ are as hereinbefore defined.

In another embodiment the invention relates to compounds of general formula IV, and their pharmaceutically acceptable salts:

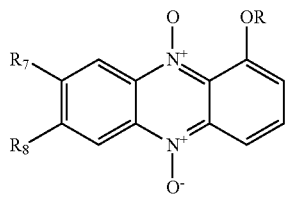

wherein:
R is selected from any of the following groups:
- —(CH$_2$)$_n$—CO—OR" (where n is an integer from 1 to 3, e.g. 1, and R" is either —H or C$_{1-6}$ alkyl);
- —CO—OR" (where R" is either —H or C$_{1-6}$ alkyl);
- —CO—(C$_{1-6}$ alkyl); and —CO—NR$_{11}$R$_{12}$ in which R$_{11}$ and R$_{12}$ are as hereinbefore defined; and R$_7$ and R$_8$ are as hereinbefore defined.

In the case where R in formula (IV) is a group —CO—NR$_{11}$R$_{12}$, R$_{11}$ and R$_{12}$ may independently be selected from —H and lower alkyl (e.g. C$_{1-6}$ alkyl), or R$_{11}$ and R$_{12}$ together may form a 5- or 6-membered heterocyclic ring which may further comprise an additional —NH— group, and wherein the heterocyclic ring may optionally be substituted by one or more lower alkyl groups (e.g. C$_{1-6}$ alkyl, preferably methyl). Examples of suitable heterocyclic rings include piperazine, N-methyl piperazine and pyrrolidine.

In one embodiment of formula (IV') or formula (IV), R$_{11}$ and R$_{12}$ may both be —H.

In formula (IV') or formula (IV), R$_7$ and R$_8$ are preferably independently selected from H, F, Cl, Br, C$_{1-3}$ alkyl, and phenyl, more preferably from H, F, Cl, Br, and C$_{1-3}$ alkyl. Preferably both R$_7$ and R$_8$ are hydrogen.

Examples of compounds of formula (IV') and formula (IV) include the following:

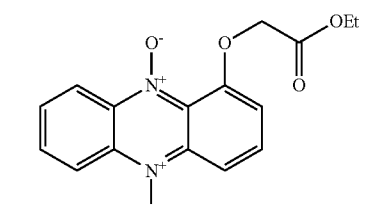

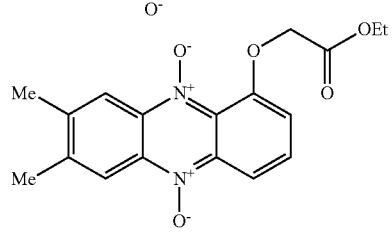

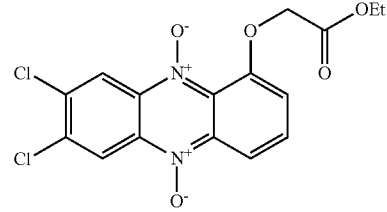

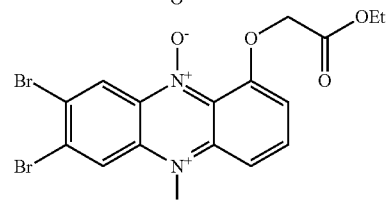

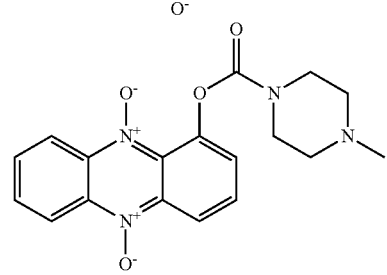

-continued

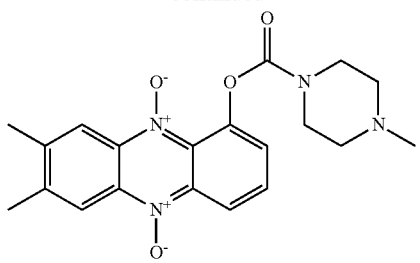

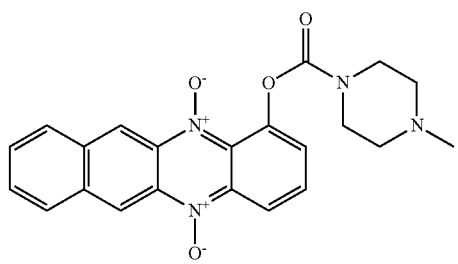

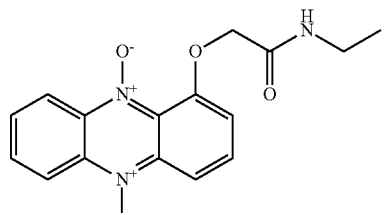

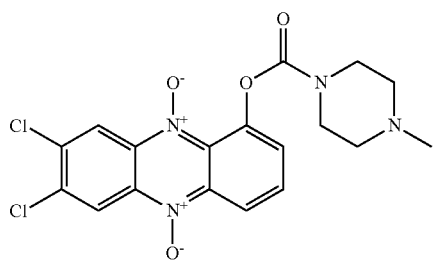

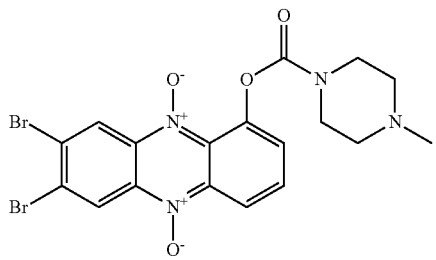

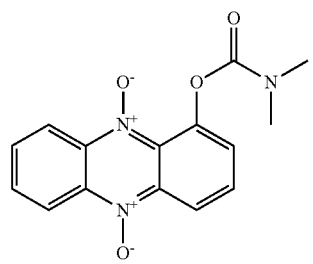

-continued
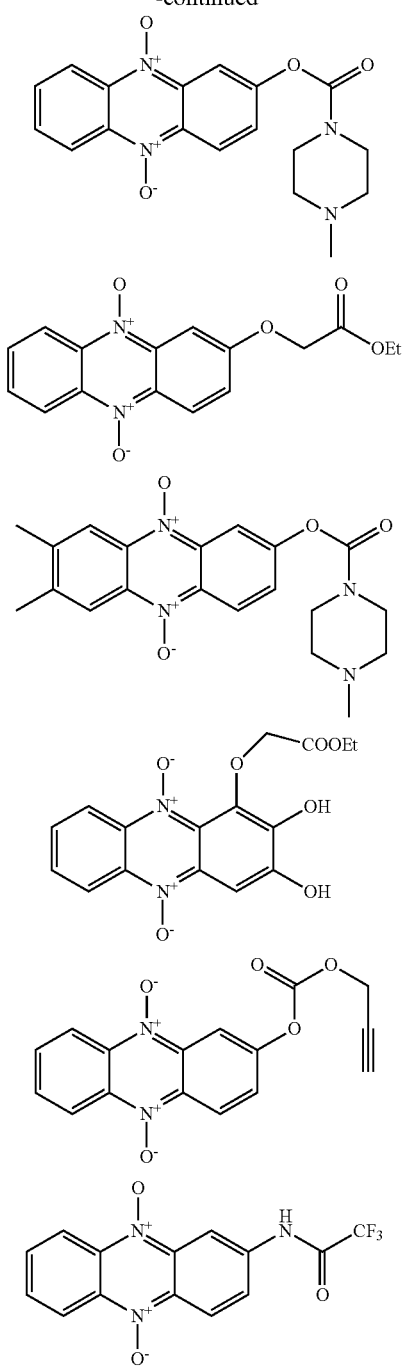
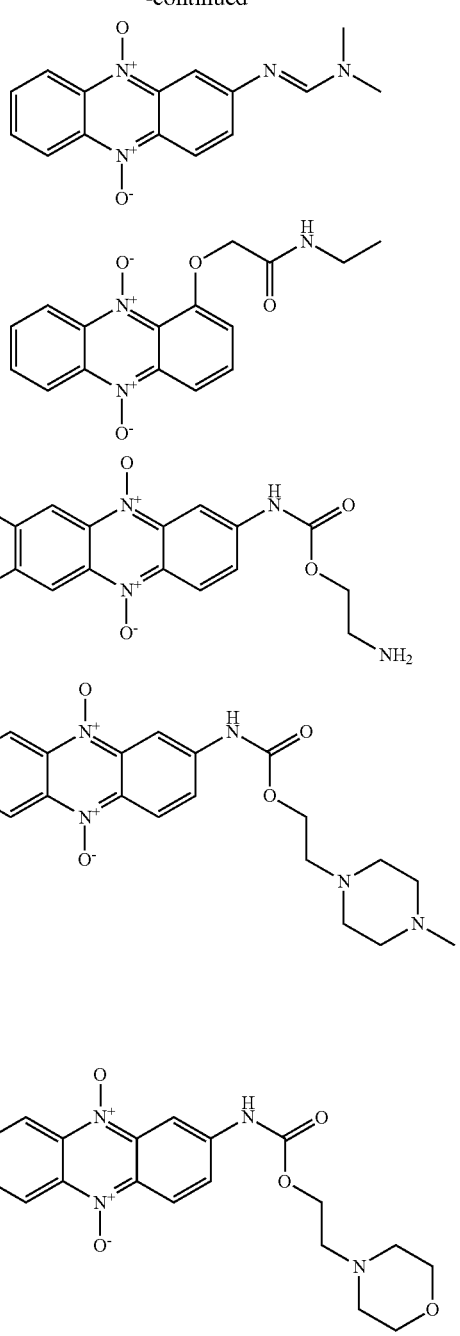
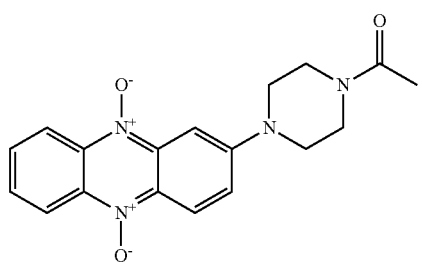
In another embodiment the invention relates to compounds of general formula (Va) and (Vb), and their pharmaceutically acceptable salts:
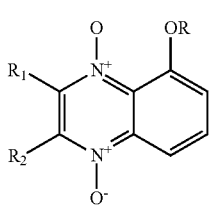
(Va)

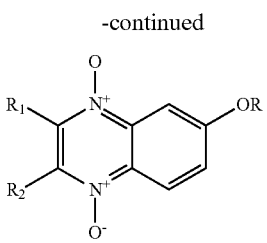

wherein:

R is selected from any of the following groups:
—(CH$_2$)$_n$—CO—OR" (where n is an integer from 1 to 3, e.g. 1, and R" is either —H or C$_{1-6}$ alkyl);
—CO—OR" (where R" is either —H or C$_{1-6}$ alkyl);
—CO—(C$_{1-6}$ alkyl);
—CO—NR$_{11}$R$_{12}$ in which R$_{11}$ and R$_{12}$ are as hereinbefore defined; and
—C$_{1-6}$ alkyl (preferably C$_{1-3}$ alkyl, e.g. methyl); and
R$_1$ and R$_2$ are as hereinbefore defined.

In the case where R in formula (Va) or formula (Vb) is a group —CO—NR$_{11}$R$_{12}$, R$_{11}$ and R$_{12}$ may independently be selected from —H and lower alkyl (e.g. C$_{1-6}$ alkyl), or R$_{11}$ and R$_{12}$ together may form a 5- or 6-membered heterocyclic ring which may further comprise an additional —NH— group, and wherein the heterocyclic ring may optionally be substituted by one or more lower alkyl groups (e.g. C$_{1-6}$ alkyl, preferably methyl). Examples of suitable heterocyclic rings include piperazine, N-methyl piperazine and pyrrolidine.

In one embodiment of formula (Va) or formula (Vb), R$_{11}$ and R$_{12}$ may both be —H.

In formula (Va) or (Vb), R$_1$ and R$_2$ are preferably independently selected from hydrogen, lower alkyl (e.g. C$_{1-6}$ alkyl), halogen (e.g. F, Cl, Br, I), and an acidic group which is —COOH, —SO$_3$H, —PO$_3$H$_2$ or —B(OH)$_2$. More preferably, R$_1$ and R$_2$ are independently selected from hydrogen, lower alkyl (e.g. C$_{1-6}$ alkyl), and halogen (e.g. F, Cl, Br, I). In one embodiment R$_1$ and R$_2$ are both —H, or both methyl.

In formula (Va) or (Vb), R$_1$ and R$_2$ are preferably lower alkyl (e.g. methyl).

Examples of compounds of formula (Va) include the following:

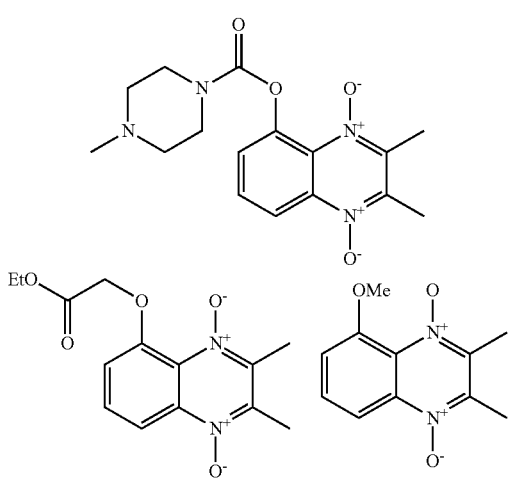

In one embodiment of the invention the compounds may be linked to one or more targeting groups, either via a bond (e.g. a covalent bond) or via a suitable linking group. Suitable linking groups may readily be determined by those skilled in the art.

The targeting groups include vectors capable of targeting the compound to a specific tissue. Suitable vectors may readily be selected by those skilled in the art, but include in particular proteins, peptides, carbohydrates, lipids, or any combination thereof. In one embodiment the vector is a monoclonal antibody (mab) or a drug. For the treatment of AML, groups on the surface of the target cells of interest include the folate receptor 2 which has been evaluated as a drug carrier target. Antigens such as CD33 (Gasiorowski et al., 2014), CD123, CD47 and IL1RAP (IL1R$_3$) also represent potential targets for antibody-based AML therapy strategies in the present invention.

The compounds of the present invention may have increased specificity by conjugation to proteins such as monoclonal antibodies (mab). Emtuzumab ozogamicin (GO) is a humanized anti-CD33 antibody conjugated to the cytotoxic natural product calicheamicin. It was withdrawn from market in June 2010 after a clinical trial showing the drug increased patient mortality and added no benefit over conventional cancer therapies because of limitations related to toxicity of the drug. A novel anti-CD33 conjugate (SGN-CD33A) by replacing calicheamicin with another cytotoxic agent, pyrrolobenzodiazepine (Kung Sutherland et al., 2013) is now in clinical trials (NCT02326584, NCT01902329). Even more advanced strategies are now under development, such as CD33/CD3-directed bispecific T-cell engager (BiTE) antibodies and bispecific killer cell engagers (BiKE) which target CD16 on NK cells and tumor-specific antigens, such as CD33. Any of these antibody strategies may be employed as suitable examples of the targeting groups (vectors) as mentioned herein.

One disadvantage with these examples of cytotoxic drugs attached to a monocolonal antibody is the use of non-selective, highly toxic compounds like calicheamicin, pyrrolobenzodiazepine, colcichin and other compounds that generate substantial side effects in patients suffering from AML. Unlike calicheamicin, pyrrolobenzodiazepine, colcichin and other compounds in the prior art, iodinin (1) has been shown to have a selective cytotoxic effect towards AML cells, and less toxicity towards healthy cells such as cardiomyocytes. It was recently reported that iodinin, extracted for a bioprospecting screen of marine actinomycetes bacteria, had a pronounced effect on AML cells (Myhren et al, Marine drugs 11 (2), 332 (2013) and was found to be particularly potent against leukaemia cell lines and AML-patient blasts. It was less toxic towards peripheral blood leukocytes (PBL), rat cardiomyoblasts and blood platelets than the gold standard drug presently used in the clinic, daunorubicin (DNR), at comparable anti-AML activity. Even direct infusion of a supra-saturated solution of iodinin into the gut of the mouse through a tube failed to cause any intestinal symptoms or histologically detectable alteration of the intestinal mucosa, like mucositis, which is common after anthracycline treatment.

Examples of N-oxide ionophores in accordance with the invention having enhanced membrane penetration compared to conventional hydroxylated N-heterocycles are given in Scheme 4:

Scheme 4
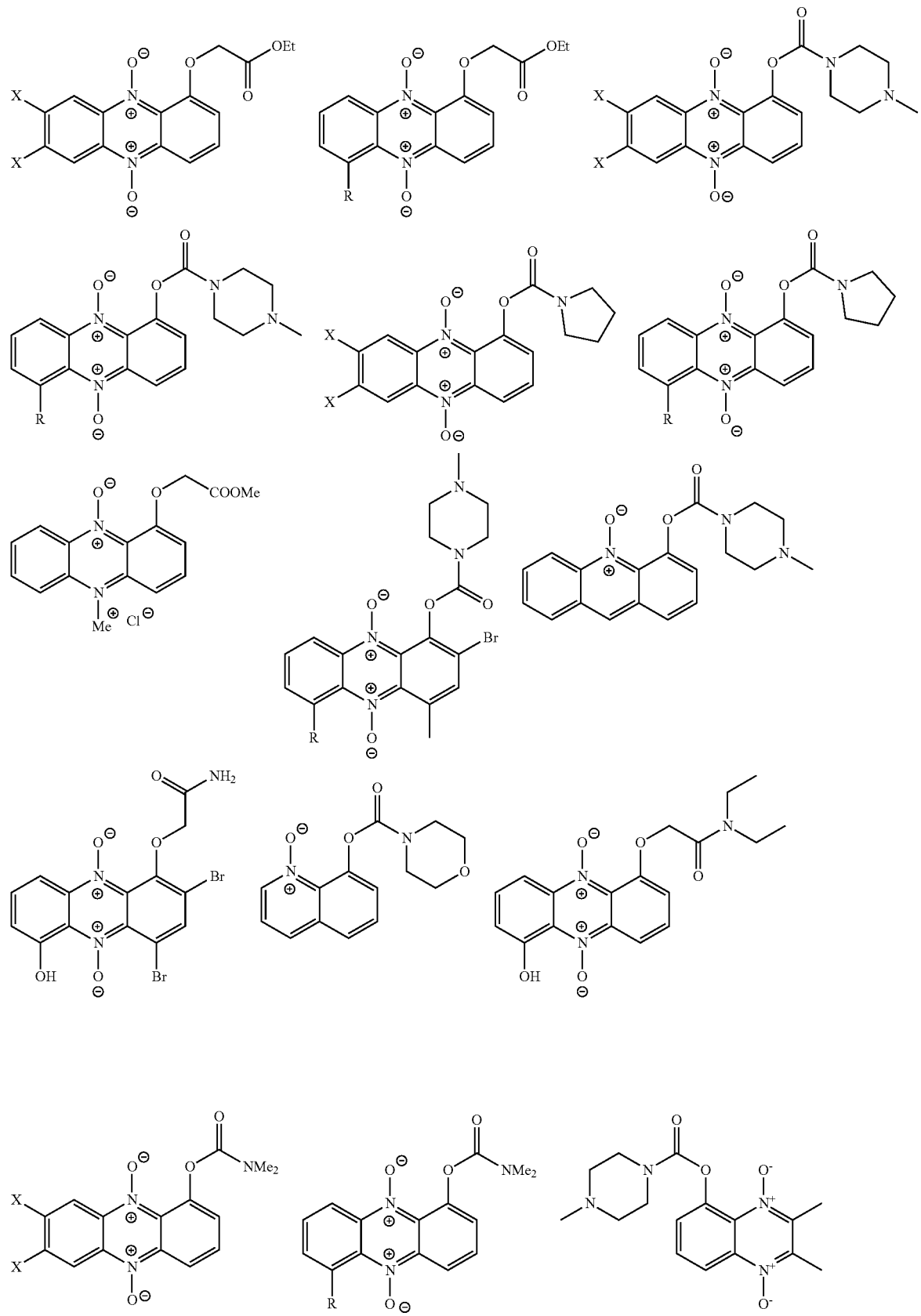

-continued

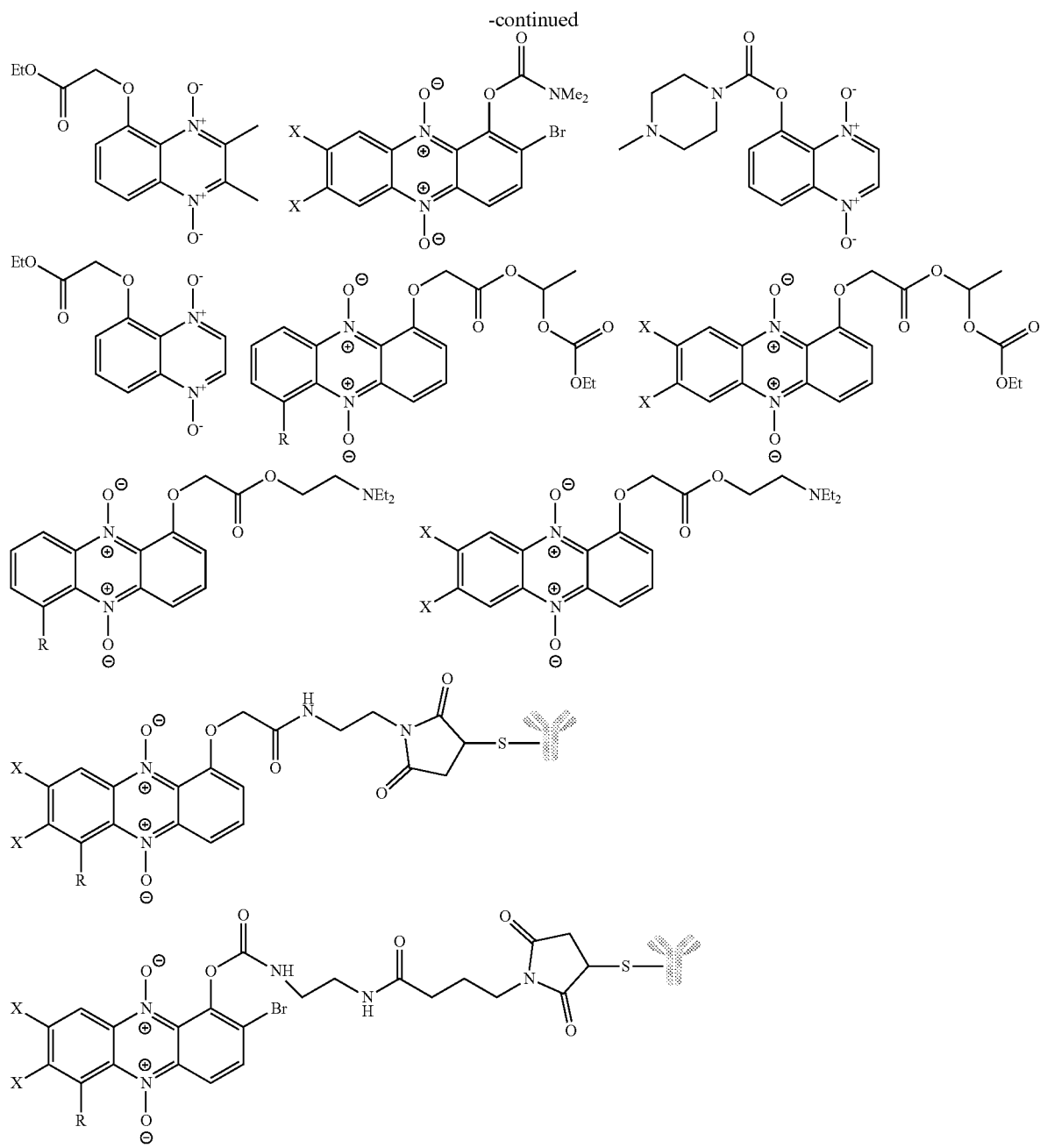

As will be understood, any of the compounds herein described may be provided in the form of a pharmaceutically acceptable salt. The compounds according to the invention may be converted into a salt thereof, particularly into a pharmaceutically acceptable salt thereof with an inorganic or organic acid or base. Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

The compounds herein described are useful in methods of therapy, in particular as anti-neoplastic and anti-infective agents.

In a further aspect the invention provides a compound as herein described for use in therapy or for use as a medicament.

In another aspect the invention provides a pharmaceutical composition comprising a compound as herein described together with at least one pharmaceutically acceptable carrier or excipient.

By "pharmaceutically acceptable" is meant that the ingredients must be compatible with other ingredients of the composition as well as physiologically acceptable to the recipient. Pharmaceutical compositions according to the present invention may be formulated according to techniques and procedures well known in the art and widely described in the literature and may comprise any of the known carriers, diluents or excipients. Other ingredients may of course also be included, according to techniques well known in the art, e.g. stabilisers, preservatives, etc.

The compounds and pharmaceutical compositions may be used in treating or preventing cancer. In particular, these may be used in preventing and/or retarding proliferation of tumor cells, for example in the treatment and/or prevention of any of the following cancers: acute lymphocytic leukemia (ALL), acute myeloid leukemia (AML), chronic lymphocytic leukemia (CLL), chronic myeloid leukemia (CML), breast cancer, prostate cancer, osteosarcoma, ovarian cancer, pancreatic cancer, adrenal cancer, liver cancer, bile duct cancer, bladder cancer, stomach cancer, bone cancer, neurobastoma, glioblastoma, melanoma, kidney cancer, Non-Hodgkin lymphoma, testicular cancer, multiple myeloma, brain/CNS tumors, cervical cancer, colon/rectum cancer, endometrial cancer, esophagus cancer, gallbladder cancer, gastrointestinal tumors, hodgkin disease, kaposi sarcoma, laryngeal and hypopharyngeal cancer, lung cancer, lymphoma, malignant mesothelioma, nasopharyngeal cancer, pituitary tumors, retinoblastoma, small intestine cancer, thymus cancer, thyroid cancer, and uterine sarcoma, preferably acute myeloid leukemia (AML).

Alternatively, the compounds and pharmaceutical compositions herein described may be used in treating an infection, preferably a bacterial or fungal infection, e.g. infections caused by *Pseudomonas aeruginosa, Bacteriocides fragilis, Escherichia coli, Aeromonas hydrophila, Klebsiella pneumoniae, Pseudomonas aeruginosa, Serratia marcescens, Stenotrophomonas maltophilia, Shigella flexneri, Alcaligenes, Aylosoxidans, Legionella gormanii, Chryseobacterium meningosepticum, Chhryseobaclerium indologenes, Acinelobacler baumannii, Citrobacter freundii*, and *Enterobacter cloacae*.

More specifically, the compounds of the invention and the pharmaceutical compositions herein described are useful against the bacteria: *Acetobacter aurantius, Acinetobacter bitumen, Actinomyces israelii, Agrobacterium radiobacter, Agrobacterium tumefaciens, Anaplasma phagocytophilum, Azorhizobium caulinodans, Azotobacter vinelandii, viridans streptococci, Bacillus Bacillus anthracis, Bacillus brevis Bacillus cereus, Bacillus fusiformis, Bacillus licheniformis, Bacillus megaterium, Bacillus mycoides, Bacillus stearothermophilus, Bacillus subtilis, Bacillus Thuringiensis, Bacteroides Bacteroides, fragilis Bacteroides, gingivalis Bacteroides, melaninogenicus* (now known as *Prevotella melaninogenica*), *Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae* (previously called *Chlamydia pneumoniae*), *Chlamydophila psittaci* (previously called *Chlamydia psittaci*), *Clostridium botulinum, Clostridium difficile, Clostridium perfringens* (previously called *Clostridium welchii*), *Clostridium tetani, Corynebacterium diphtheriae, Corynebacterium fusiforme, Coxiella burnetii, Diplococcus pneumoniae, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Klebsiella pneumoniae, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasmafermentans, Mycoplasma gallinarum, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Porphyromonas gingivalis, Prevotella melaninogenica* (previously called *Bacteroides melaninogenicus*), *Pseudomonas aeruginosa, Rhizobium radiobacter, Rickettsia Rickettsia prowazekii, Rickettsia psittaci, Rickettsia quintana, Rickettsia rickettsii, Rickettsia trachomae, Rochalimaea, Rochalimaea henselae, Rochalimaea quintana, Rothia dentocariosa, Salmonella enteritidis, Salmonella schottmuelleri, Salmonella typhi, Salmonella typhimurium, Serratia marcescens, Shigella dysenteriae, Spirillium Volutans, Staphylococcus aureus, Staphylococcus epidermidis, Stenotrophomonas maltophilia, Streptococcus agalactiae, Streptococcus avium Streptococcus bovis, Streptococcus cricetus, Streptococcus faceium, Streptococcus faecalis Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Wolbachia, Yersinia enterocolitica, Yersinia pestis*, and *Yersinia pseudotuberculosis*.

As described in the prior art, e.g. by Zhang et al, in Diagnostic Microbiology and Infectious Disease 88 (2017) 247-251, cancer patients often suffer from life-threatening infections due to an impaired immune system. Therefore, cancer patients often receive antibiotic therapy in combination with anti-cancer therapy. As documented in the examples herein, many of the compounds according to the present invention have both anti-cancer and antibacterial effects and are thus particularly suitable for the treatment of cancer patients who are suffering from an infection or who may be susceptible to such an infection, e.g. a bacterial or fungal infection such as any of those described herein.

Compositions according to the invention may also comprise combinations of two or more active compounds to provide the broadest possible therapy, e.g. two or more compounds according to the invention. Therapy using the compounds according to the invention may also be combined with conventional antibiotics used in the cancer clinic, e.g. β-lactams such as penicillins, carbapenems and cephalosporins, fluoroquinolones, polymyxins, macrolides, sulphonamides, aminoglycosides, tetracyclines and oxazolidinones. Compositions which contain one or more of such antibiotics, in addition to one or more compounds according to the invention, form a further aspect of the invention. Combination therapies in which one or more of the compounds of the invention are administered, either separately or simultaneously, with one or more conventional antibiotics also form part of the invention.

Compositions comprising the compounds are preferably formulated prior to administration. The active ingredients in such compositions may comprise from 0.05% to 99% by weight of the formulation. Appropriate dosages may depend on the modulator to be used, precise condition to be treated, age and weight of the patient etc. and may be routinely determined by the skilled practitioner according to principles well known in the art. By way of example, representative dosages may include 1 to 200 or 1-100 mg/kg, e.g. 5 to 70, 5-50, or 10 to 70 or 10 to 50 mg/kg.

The formulations may be in the form of sterile aqueous solutions and/or suspensions of the pharmaceutically active ingredients, aerosols, ointments and the like. Especially preferred in the present invention are the formulations in a sustained release form e.g. microparticles, nanoparticles, emulsions, nano-suspensions, lipid particles or oils.

The administration may be by any suitable method known in the medicinal arts, including oral, parenteral, topical, rectal or subcutaneous administration or by inhalation. The compounds or formulations comprising the compounds may be administered in a single dose to be taken at regular intervals e.g. once or twice a day, once every 48 hours or once every 72 hours, or as an infusion during several hours or days, e.g. in the case of use of ArC or DNR. Sustained formulations may be given at longer intervals e.g. 1 to 2 times a month or every three months. The precise dosage of the active compounds to be administered, the number of daily or monthly doses and the length of the course of treatment will depend on a number of factors, including the age of the patient and their weight.

The compositions may be formulated according to techniques and procedures well known in the literature and may comprise any of the known carriers, diluents or excipients. For example the compositions or formulations which can be used in the present invention which are suitable for parenteral administration conveniently may comprise sterile aqueous solutions and/or suspensions of pharmaceutically active ingredients preferably made isotonic with the blood of the recipient generally using sodium chloride, glycerin, glucose, mannitol, sorbitol and the like. In addition, the composition may contain any of a number of adjuvants, such as buffers, preservatives, dispersing agents, agents that promote rapid onset of action or prolonged duration of action. Compositions/formulations suitable for oral administration may be in sterile purified stock powder form, preferably covered by an envelope or envelopes which may contain any of a number or adjuvants such as buffers, preservative agents, or agents that promote prolonged or rapid release. Compositions/formulations for use in the present invention suitable for local or topical administration may comprise the compound mixed with known suitable ingredients such as paraffin, vaseline, cetanol, glycerol and the like, to form suitable ointments or creams.

Any of the compositions and formulations herein described may be combined with one or more conventional antioxidants, e.g. ascorbic acid, ascorbyl palmitate, ascorbyl stearate, BHA, BHT, citric acid, gum guaiac, lecithin, lecithin citrate, monoglyceride citrate, onoisopropyl citrate, propyl gallate, EDTA, tartaric acid, or any combination thereof.

SPECIFIC EMBODIMENTS i. A compound of general formula (I'), or a pharmaceutically acceptable salt thereof:

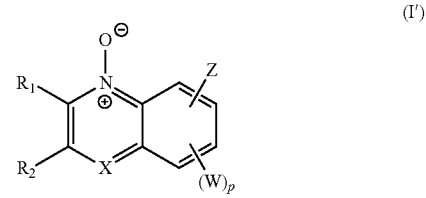

(I')

wherein:
X is an N-oxide functionality ($N^+$—$O^-$), or CH;
Z is a group susceptible to hydrolytic and/or enzymatic cleavage in vivo to form a group selected from —OH, —COOH, —CONH$_2$, —O-Q-COOH and —O-Q-CONH$_2$ (where Q is a straight chained or branched alkylene group, preferably $C_{1-3}$ alkylene, e.g. methylene), and
Z is optionally linked to one or more targeting groups;
$R_1$ and $R_2$ are independently selected from hydrogen, lower alkyl (e.g. $C_{1-6}$ alkyl), halogen (e.g. F, Cl, Br, I), an acidic group which is —COOH, —SO$_3$H, —PO$_3$H$_2$ or —B(OH)$_2$; and an aryl group (e.g. phenyl); or
$R_1$ and $R_2$, together with the intervening carbon atoms, form an optionally substituted aromatic group;
each W is independently selected from lower alkyl (e.g. $C_{1-6}$ alkyl), halogen (e.g. F, Cl, Br, I), OH, and an acidic group which is —COOH, —SO$_3$H, —PO$_3$H$_2$ or —B(OH)$_2$; and
p is an integer from 0 to 3.

ii. A compound as defined in embodiment i, of general formula (I), or a pharmaceutically acceptable salt thereof:

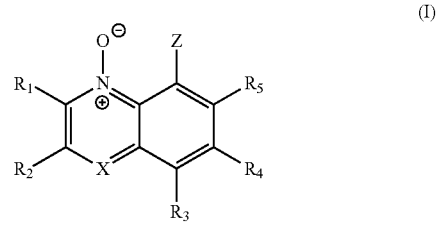

(I)

wherein:
X is an N-oxide functionality ($N^+$—$O^-$), or CH;
Z is a group susceptible to hydrolytic and/or enzymatic cleavage in vivo to form a group selected from —OH, —COOH, —CONH$_2$, —O-Q-COOH and —O-Q-CONH$_2$ (where Q is a straight chained or branched alkylene group, preferably $C_{1-3}$ alkylene, e.g. methylene), and
Z is optionally linked to one or more targeting groups;
$R_1$ and $R_2$ are independently selected from hydrogen, lower alkyl (e.g. $C_{1-6}$ alkyl), halogen (e.g. F, Cl, Br, I), an acidic group which is —COOH, —SO$_3$H, —PO$_3$H$_2$ or —B(OH)$_2$; and an aryl group (e.g. phenyl); or R<sub>1</sub> and R<sub>2</sub>, together with the intervening carbon atoms, form an optionally substituted aromatic group;

R<sub>3</sub>, R<sub>4</sub> and R<sub>5</sub> are independently selected from hydrogen, lower alkyl (e.g. $C_{1-6}$ alkyl), halogen (e.g. F, Cl, Br, I), and an acidic group which is —COOH, —SO<sub>3</sub>H, —PO<sub>3</sub>H<sub>2</sub> or —B(OH)<sub>2</sub>.

iii. A compound as defined in embodiments i or ii, wherein X is an N-oxide functionality.

4iv. A compound as defined in any one of embodiments i-iii, wherein Z is an organic group containing one or more ester, carbonate ester, or carbamate groups (including sterically hindered ester groups), which is optionally linked to one or more targeting groups.

v. A compound as defined in any one of the preceding embodiments, wherein Z is a group having the formula: -T-A-Y in which:

T is a group selected from —O—, —NR<sub>9</sub>—, —S—, —(C=O)—, —(CHR<sub>9</sub>)— (where R<sub>9</sub> is —H or $C_{1-3}$ alkyl), —COU— and —SO<sub>2</sub>U— (where U is —O—, —S—, —NR<sub>10</sub>— or —CHR<sub>10</sub>— in which R<sub>10</sub> is —H or $C_{1-3}$ alkyl);

A is —(C=O)—, lower alkylene (e.g. straight chained or branched $C_{1-6}$ alkylene), or an arylene group optionally substituted with one or more alkylamino (e.g. $C_{1-6}$ alkylamino) or alkoxy (e.g. $C_{1-6}$ alkoxy) groups; and Y is a hydrophilic monomeric, oligomeric or polymeric group comprising hydrogen bond donor and/or hydrogen bond acceptor atoms, for example selected from H, N, O, S and P, e.g. a hydrophilic group comprising one or more functional groups selected from —OH, —SH, —CO<sub>2</sub>H, —SO<sub>3</sub>H, —PO<sub>3</sub>H<sub>2</sub>, —B(OH)<sub>2</sub>, and aliphatic or aromatic nitrogen-containing groups; or Y is any of the groups mentioned above linked to one or more targeting groups.

vi. A compound as defined in embodiment 5, wherein Y is a group —NR<sub>11</sub>R<sub>12</sub> in which R<sub>11</sub> and R<sub>12</sub> are independently selected from —H, lower alkyl (preferably $C_{1-6}$ alkyl, e.g. methyl or ethyl) and aryl, or R<sub>11</sub> and R<sub>12</sub> together form a 5- or 6-membered heterocyclic ring which may further comprise one or more (preferably one) —O—, —S—, or —NH— ring atoms, and wherein the heterocyclic ring may optionally be substituted by one or more lower alkyl (e.g. $C_{1-6}$ alkyl) or aryl (e.g. phenyl) groups.

vii. A compound as defined in embodiment v, wherein Y is a group —(CHR<sub>13</sub>)—O—(C=O)—R<sub>14</sub> where R<sub>13</sub> is —H or $C_{1-3}$ alkyl, and R<sub>14</sub> is an aliphatic, aromatic or alicyclic group comprising 1-50 carbon atoms, for example a lower alkyl group (e.g. $C_{1-6}$ alkyl) or aryl group.

viii. A compound as defined in embodiment v, wherein Y is a group —(CHR<sub>15</sub>)—NR<sub>16</sub>—COOR<sub>17</sub> where R<sub>15</sub> is —H or $C_{1-3}$ alkyl, and R<sub>16</sub> and R<sub>17</sub> are independently —H, lower alkyl (e.g. $C_{1-6}$ alkyl) or aryl.

ix. A compound as defined in any one of embodiments i to 4, wherein Z is a group selected from the following:

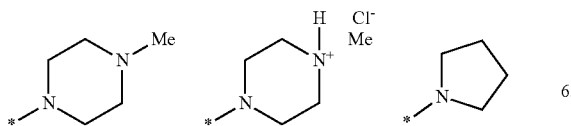

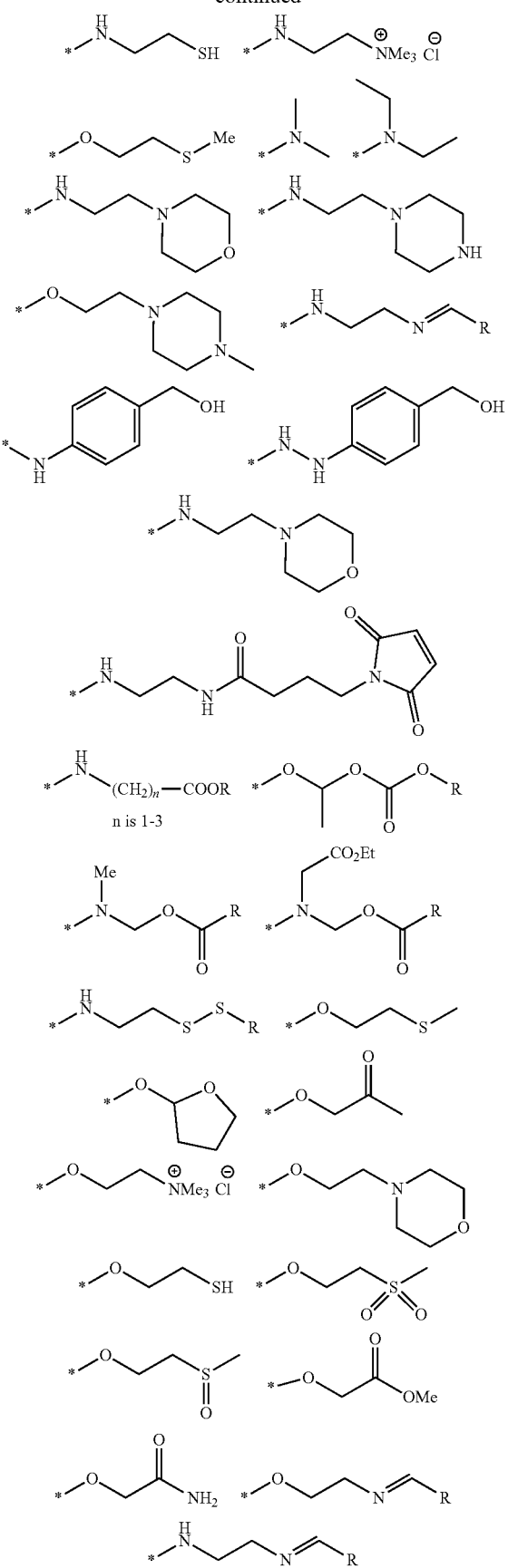

-continued

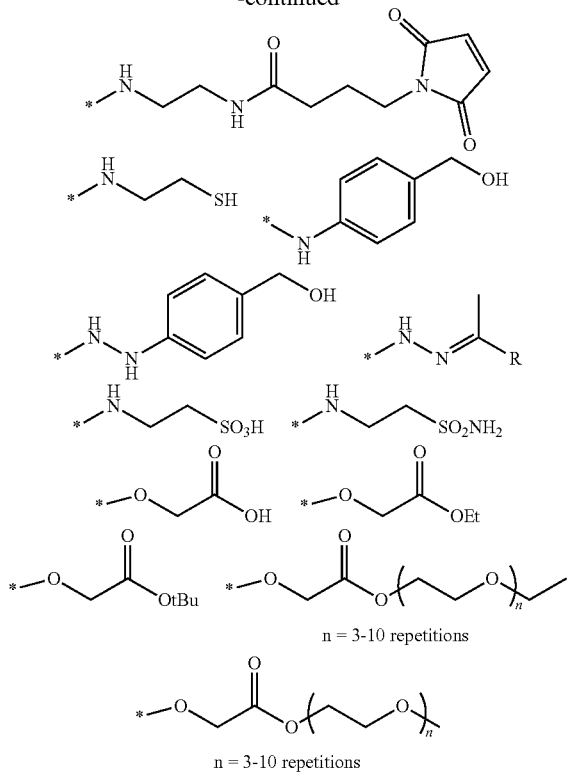

n = 3-10 repetitions

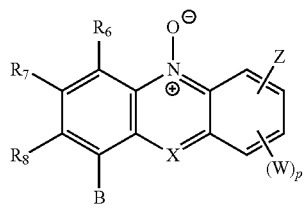

n = 3-10 repetitions

In which * denotes the point of attachment to the remainder of the molecule; and R is either -H or $C_{1-3}$ alkyl x. A compound as defined in embodiment i which is a compound of general formula (II'), or a pharmaceutically acceptable salt thereof:

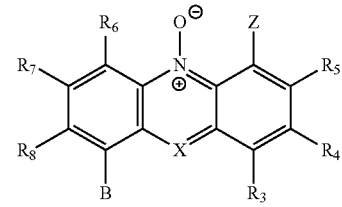
(II')

wherein X, Z, W and p are as defined in any one of embodiments i to ix;

$R_6$, $R_7$ and $R_8$ are independently selected from hydrogen, lower alkyl (e.g. $C_{1-6}$ alkyl), halogen (e.g. F, Cl, Br, I), and an acidic group which is —COOH, —$SO_3H$, —$PO_3H_2$ or —$B(OH)_2$;

$R_7$ and $R_8$ may also independently represent an aryl group (e.g. phenyl); and B is either a group Z as defined in any one of embodiments i to ix, or may be selected from —H, —OH, —SH, —OR or —SR (wherein R is $C_{1-6}$ alkyl, preferably $C_{1-3}$ alkyl, e.g. methyl), and halogen (e.g. F, Cl, Br, I).

xi. A compound as defined in embodiment i which is a compound of general formula (II), or a pharmaceutically acceptable salt thereof:

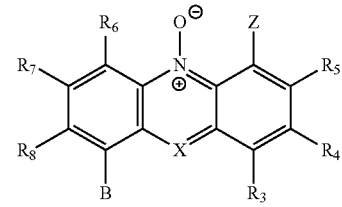
(II)

wherein X, Z, $R_3$, $R_4$ and $R_5$ are as defined in any one of embodiments i to ix;

$R_6$, $R_7$ and $R_8$ are independently selected from hydrogen, lower alkyl (e.g. $C_{1-6}$ alkyl), halogen (e.g. F, Cl, Br, I), and an acidic group which is —COOH, —$SO_3H$, —$PO_3H_2$ or —$B(OH)_2$;

$R_7$ and $R_8$ may also independently represent an aryl group (e.g. phenyl); and B is either a group Z as defined in any one of embodiments i to ix, or may be selected from —H, —OH, —SH, —OR or —SR (wherein R is $C_{1-6}$ alkyl, preferably $C_{1-3}$ alkyl, e.g. methyl), and halogen (e.g. F, Cl, Br, I).

xii. A compound as defined in embodiment x or embodiment xi, wherein B is selected from —H, —OH, —SH, —OR or —SR (wherein R is $C_{1-6}$ alkyl, preferably $C_{1-3}$ alkyl, e.g. methyl), and halogen (e.g. F, Cl, Br, I).

xiii. A compound as defined in embodiment i which is a compound of general formula (IIIa) or (IIIb), or a pharmaceutically acceptable salt thereof:

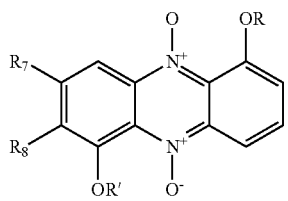
(IIIa)

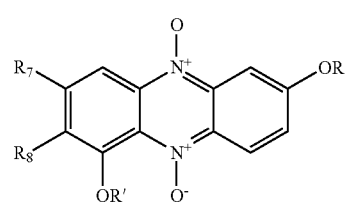
(IIIb)

wherein:

R is selected from any of the following groups:
—$(CH_2)_n$—CO—OR" (where n is an integer from 1 to 3, e.g. 1, and R" is either —H or $C_{1-6}$ alkyl);
—CO—OR" (where R" is either —H or $C_{1-6}$ alkyl);
—CO—($C_{1-6}$ alkyl); and
—CO—$NR_{11}R_{12}$ in which $R_{11}$ and $R_{12}$ are as defined in embodiment vi;

R' either corresponds to group R or is selected from —H and $C_{1-6}$ alkyl (preferably $C_{1-3}$ alkyl, e.g. methyl); and $R_7$ and $R_8$ are as defined in embodiment x.

xiv. A compound as defined in embodiment i which is a compound of general formula (IIIa), or a pharmaceutically acceptable salt thereof:

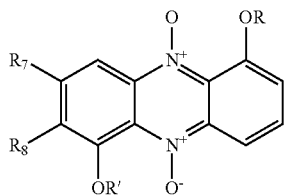

(IIIa)

wherein:
R is selected from any of the following groups:
—(CH$_2$)$_n$—CO—OR" (where n is an integer from 1 to 3, e.g. 1, and R" is either —H or C$_{1-6}$ alkyl);
—CO—OR" (where R" is either —H or C$_{1-6}$ alkyl);
—CO—(C$_{1-6}$ alkyl); and
—CO—NR$_{11}$R$_{12}$ in which R$_{11}$ and R$_{12}$ are as defined in embodiment vi;
R' either corresponds to group R or is selected from —H and C$_{1-6}$ alkyl (preferably C$_{1-3}$ alkyl, e.g. methyl); and
R$_7$ and R$_8$ are as defined in embodiment x.

xv. A compound as defined in embodiment xiii or embodiment xiv, wherein R' is —H or methyl.
xvi. A compound as defined in any one of embodiments xiii to xv, wherein R and/or R' in formula (IIIa) or formula (IIIb) is a group —CO—NR$_{11}$R$_{12}$, in which R$_{11}$ and R$_{12}$ may independently be selected from —H and lower alkyl (e.g. C$_{1-6}$ alkyl), or R$_n$ and Ru together may form a 5- or 6-membered heterocyclic ring which may further comprise an additional —NH— group, and wherein the heterocyclic ring may optionally be substituted by one or more lower alkyl groups (e.g. C$_{1-6}$ alkyl, preferably methyl).
xvii. A compound as defined in embodiment xvi, wherein R$_{11}$ and R$_{12}$ are both —H.
xviii. A compound as defined in any one of embodiments xiii to xvii, wherein R$_7$ and R$_8$ are independently selected from H, F, Cl, Br, C$_{1-3}$ alkyl and phenyl, more preferably from H, F, Cl, Br, and C$_{1-3}$ alkyl.
xix. A compound as defined in embodiment xiii or embodiment xiv which is selected from the following:

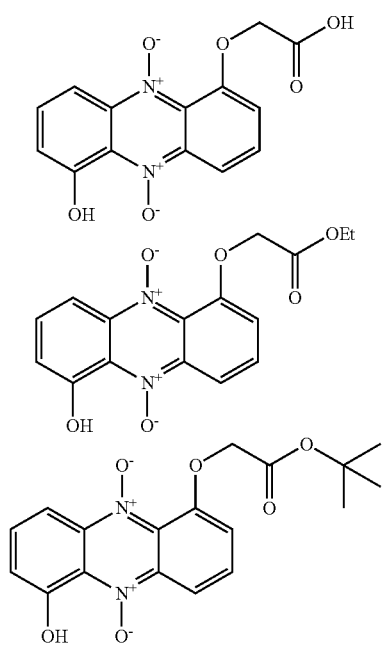

-continued

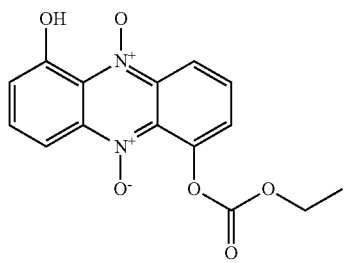

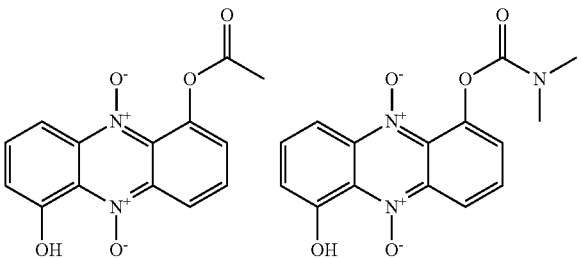

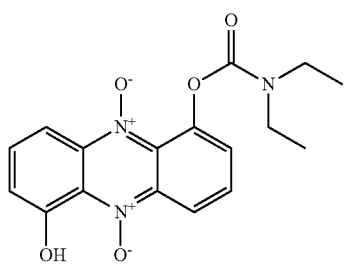

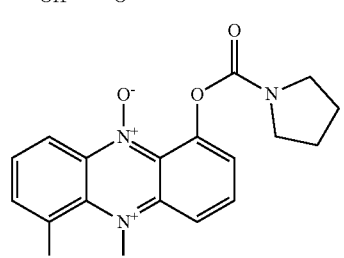

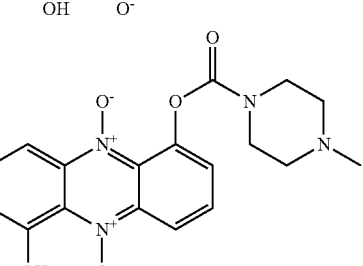

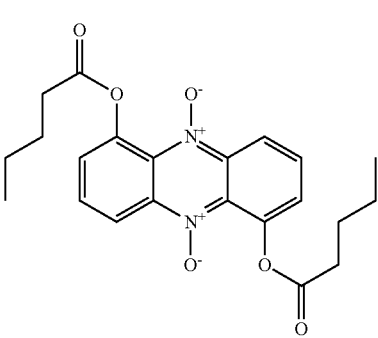

-continued

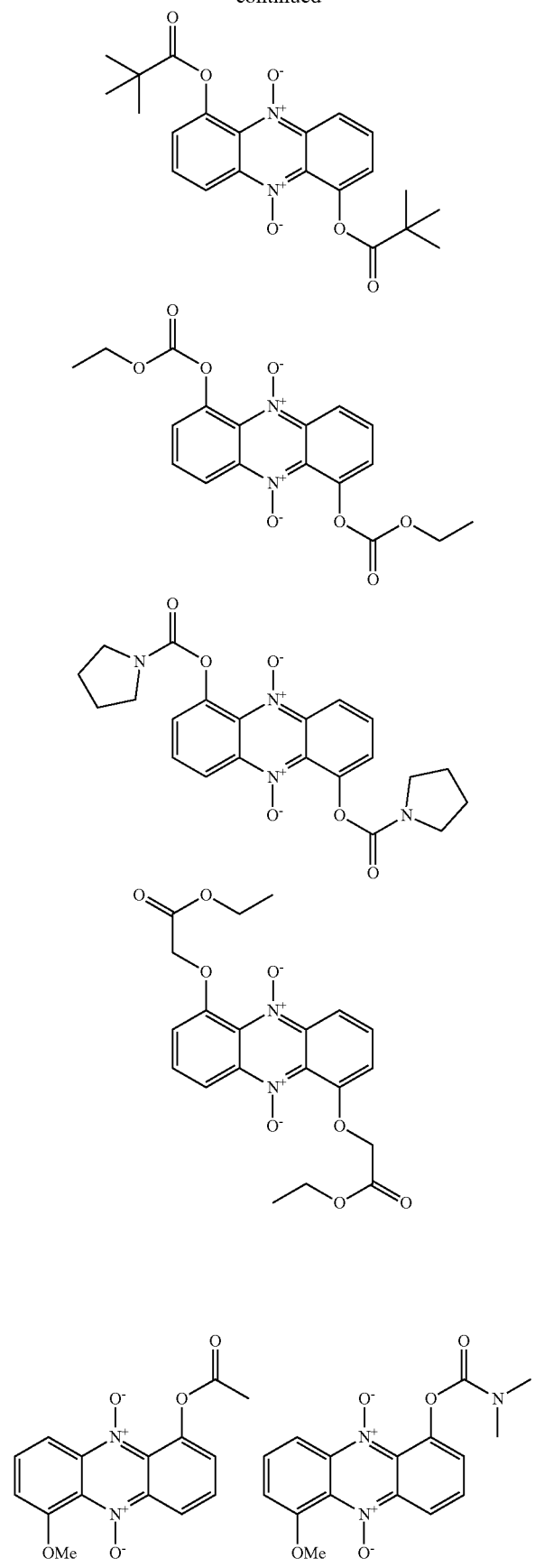

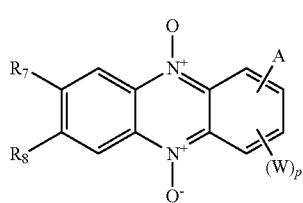

xx. A compound as defined in embodiment i which is a compound of general formula (IV'), or a pharmaceutically acceptable salt thereof:

(IV')

wherein:
A is either —OR or —NR$_{18}$R$_{19}$;
R is selected from any of the following groups:
—(CH$_2$)—CO—OR" (where n is an integer from 1 to 3, e.g. 1, and R" is either —H or C$_{1-6}$ alkyl);
—CO—OR" (where R" is either —H or C$_{1-6}$ alkyl);
—CO—(C$_{1-6}$ alkyl);
—CO—NR$_{11}$R$_{12}$ in which R$_{11}$ and R$_{12}$ are as defined in embodiment vi;
—(CH$_2$)$_n$—CO—NR$_{11}$R$_{12}$ in which R$_{11}$ and R$_{12}$ are as defined in embodiment vi;
—CO—O—CH$_2$—C≡CH;
—CS—NR"$_2$ (where each R" is either —H or C$_{1-6}$ alkyl);
R$_{18}$ is H or C$_{1-3}$ alkyl;
R$_{19}$ is selected from any of the following groups:
—COCF$_3$;
—CO—O—(CH$_2$)$_n$—NR$_{11}$R$_{12}$ (where n is an integer from 1 to 3, e.g. 1 or 2, and R$_{11}$ and R$_{12}$ are as defined in embodiment vi);
or R$_{18}$ and R$_{19}$ together may form a 5- or 6-membered heterocyclic ring which may further comprise one or more (preferably one) —O—, —S—, or —NH— ring atoms, and wherein the heterocyclic ring may optionally be substituted by one or more lower alkyl (e.g. C$_{1-6}$ alkyl) or —CO—C$_{1-6}$ alkyl groups;
or —NR$_{18}$R$_{19}$ represents a group —N═CH—NR"$_2$ (where each R" is either —H or C$_{1-6}$ alkyl); each W is independently selected from lower alkyl (e.g. C$_{1-6}$ alkyl), halogen (e.g. F, Cl, Br, I), OH, and an acidic group which is —COOH, —SO$_3$H, —PO$_3$H$_2$ or —B(OH)$_2$;

p is an integer from 0 to 3, preferably 0 or 1, e.g. 0; and
$R_7$ and $R_8$ are as defined in embodiment x.

xxi. A compound as defined in embodiment i which is a compound of general formula (IV), or a pharmaceutically acceptable salt thereof:

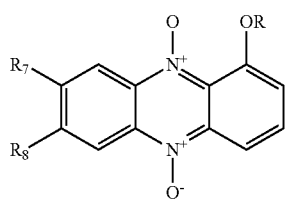

(IV)

wherein:

R is selected from any of the following groups:

—$(CH_2)_n$—CO—OR" (where n is an integer from 1 to 3, e.g. 1, and R" is either —H or $C_{1-6}$ alkyl);

—CO—OR" (where R" is either —H or $C_{1-6}$ alkyl);

—CO—($C_{1-6}$ alkyl); and

—CO—$NR_{11}R_{12}$ in which $R_{11}$ and $R_{12}$ are as defined in embodiment vi; and $R_7$ and $R_8$ are as defined in embodiment x.

xxii. A compound as defined in embodiment xx or embodiment xxi, wherein R and/or R' is a group —CO—$NR_{11}R_{12}$ in which $R_{11}$ and $R_{12}$ may independently be selected from —H and lower alkyl (e.g. $C_{1-6}$ alkyl), or $R_{11}$ and $R_{12}$ together may form a 5- or 6-membered heterocyclic ring which may further comprise an additional —NH— group, and wherein the heterocyclic ring may optionally be substituted by one or more lower alkyl groups (e.g. $C_{1-6}$ alkyl, preferably methyl).

xxiii. A compound as defined in embodiment xxii, wherein $R_7$ and $R_{12}$ are both —H.

xxiv. A compound as defined in any one of embodiments xx to xxiii, wherein $R_7$ and $R_8$ are independently selected from H, F, Cl, Br, $C_{1-3}$ alkyl, and phenyl, more preferably from H, F, Cl, Br, and $C_{1-3}$ alkyl.

xxv. A compound as defined in embodiment xxiv, wherein $R_7$ and $R_8$ are both hydrogen.

xxvi. A compound as defined in embodiment xx or embodiment xxi which is selected from the following:

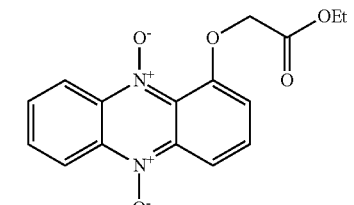

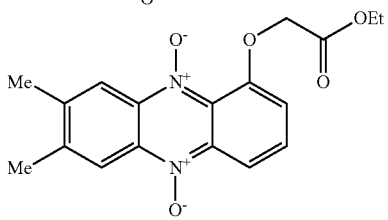

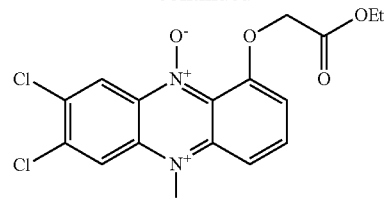

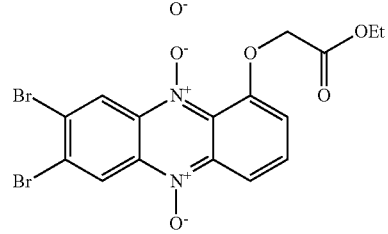

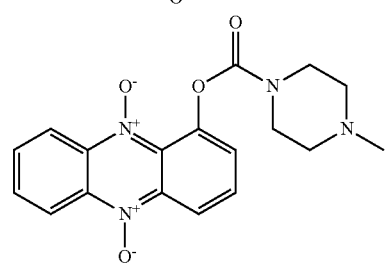

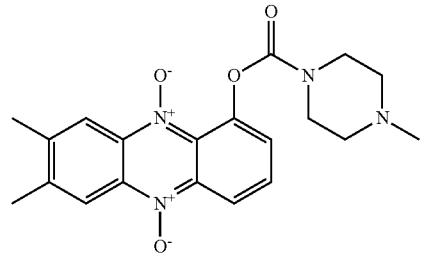

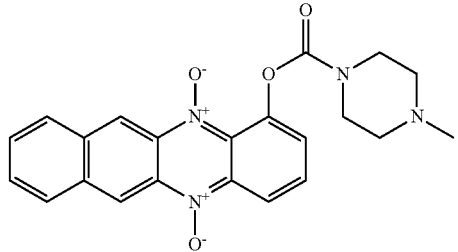

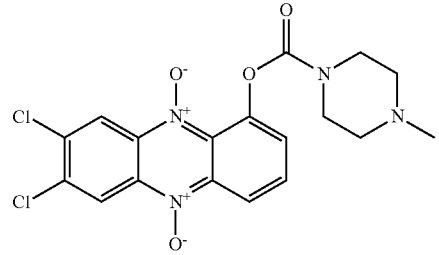

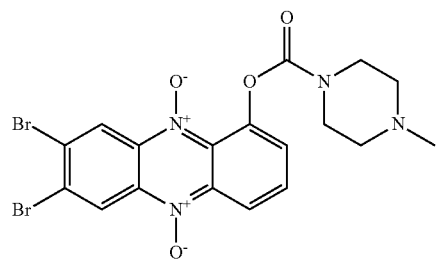

-continued

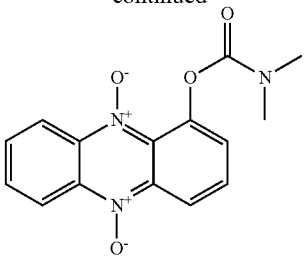

xxvii. A compound as defined in embodiment i which is a compound of general formula (Va) or (Vb), or a pharmaceutically acceptable salt thereof:

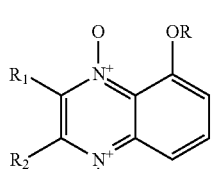
(Va)

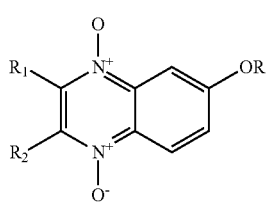
(Vb)

wherein:
R is selected from any of the following groups:
—(CH$_2$)$_n$—CO—OR" (where n is an integer from 1 to 3, e.g. 1, and R" is either —H or C$_{1-6}$ alkyl);
—CO—OR" (where R" is either —H or C$_{1-6}$ alkyl);
—CO—(C$_{1-6}$ alkyl);
—CO—NR$_{11}$R$_{12}$ in which R$_{11}$ and R$_{12}$ are as defined in embodiment vi; and
—C$_{1-6}$ alkyl (preferably C$_{1-3}$ alkyl, e.g. methyl); and
R$_1$ and R$_2$ are as defined in embodiment i or embodiment 2.

xxviii. A compound as defined in embodiment i which is a compound of general formula (Va), or a pharmaceutically acceptable salt thereof:

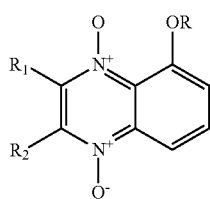
(Va)

wherein:
R is selected from any of the following groups:
—(CH$_2$)$_n$—CO—OR" (where n is an integer from 1 to 3, e.g. 1, and R" is either —H or C$_{1-6}$ alkyl);
—CO—OR" (where R" is either —H or C$_{1-6}$ alkyl);
—CO—(C$_{1-6}$ alkyl);
—CO—NR$_{11}$R$_{12}$ in which R$_{11}$ and R$_{12}$ are as defined in embodiment vi; and
—C$_{1-6}$ alkyl (preferably C$_{1-3}$ alkyl, e.g. methyl); and
R$_1$ and R$_2$ are as defined in embodiment i or embodiment 2.

xxix. A compound as defined in embodiment xxvii or embodiment xxviii, wherein R in formula (Va) or formula (Vb) is a group —CO—NR$_{11}$R$_{12}$ in which R$_{11}$ and R$_{12}$ may independently be selected from —H and lower alkyl (e.g. C$_{1-6}$ alkyl), or R$_{11}$ and R$_{12}$ together may form a 5- or 6-membered heterocyclic ring which may further comprise an additional —NH— group, and wherein the heterocyclic ring may optionally be substituted by one or more lower alkyl groups (e.g. C$_{1-6}$ alkyl, preferably methyl).

xxx. A compound as defined in embodiment xxix, wherein R$_{11}$ and R$_{12}$ are both —H.

xxxi. A compound as defined in any one of embodiments xxvii to xxx, wherein R$_1$ and R$_2$ are independently selected from hydrogen, lower alkyl (e.g. C$_{1-6}$ alkyl), halogen (e.g. F, Cl, Br, I), and an acidic group which is —COOH, —SO$_3$H, —PO$_3$H$_2$ or —B(OH)$_2$.

xxxii. A compound as defined in any one of embodiments xxvii to xxx, wherein R$_1$ and R$_2$ are both —H, or both methyl.

xxxiii. A compound as defined in embodiment xxvii or embodiment xxviii which is selected from the following:

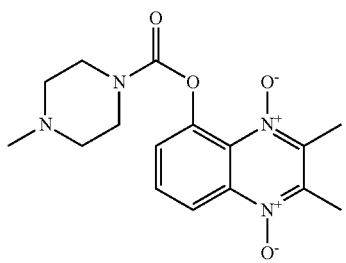

xxxiv. A compound as defined in any one of the preceding embodiments which is linked to one or more targeting groups.

xxxv. A compound as defined in embodiment xxxiv, wherein said targeting groups are selected from proteins, peptides, carbohydrates, lipids, or any combination thereof.

xxxvi. A compound as defined in embodiment xxxiv, wherein said targeting groups are selected from a monoclonal antibody (mab) and a drug.

xxxvii. A compound as defined in embodiment i which is selected from any of the following:
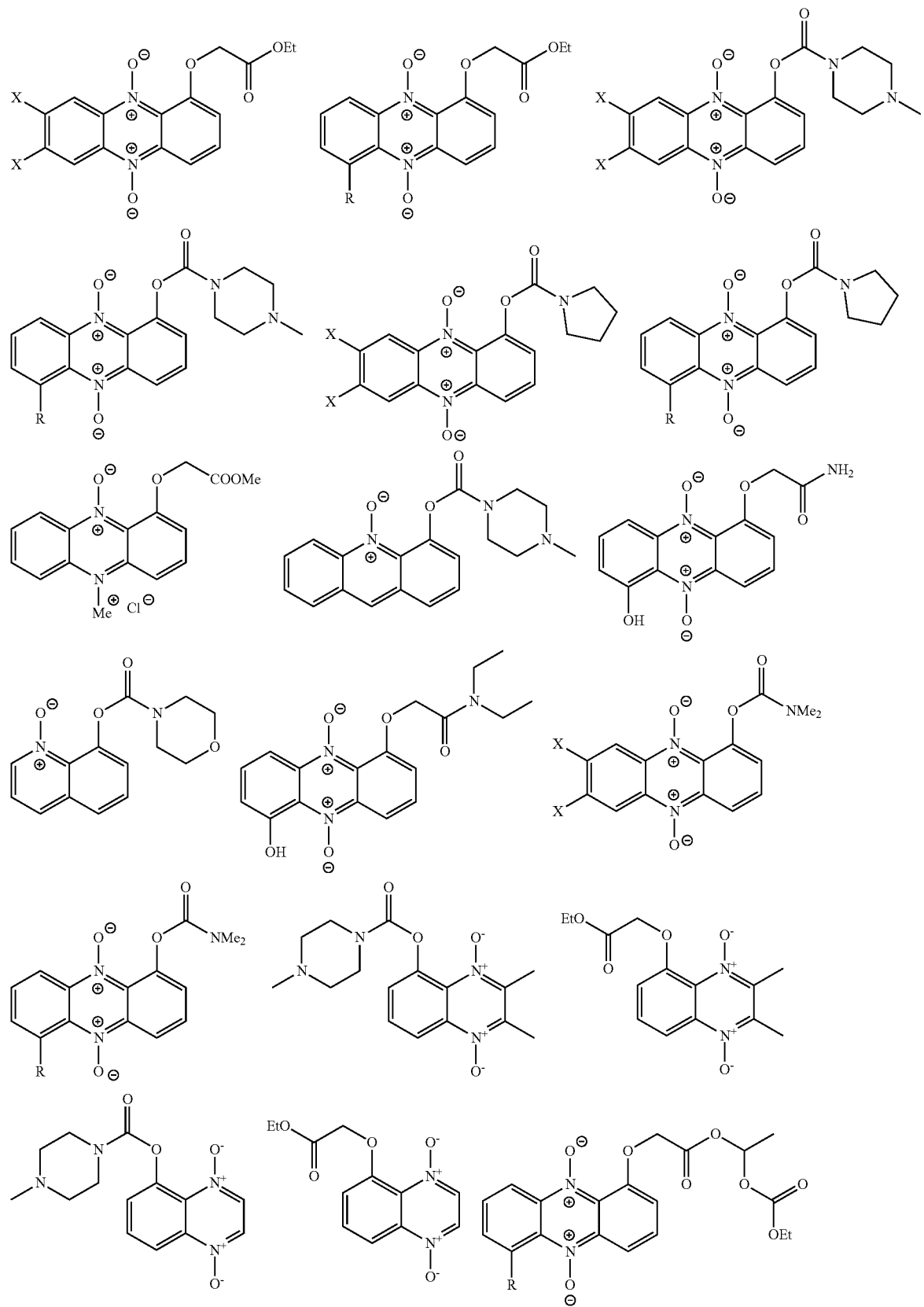

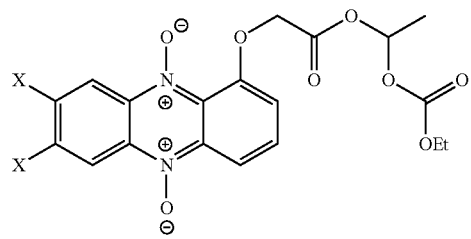
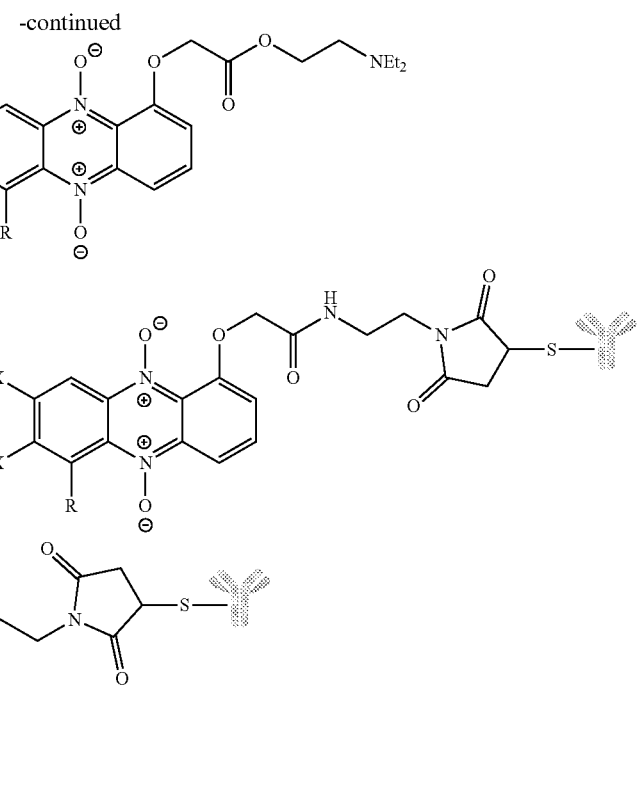

xxxviii. A pharmaceutical composition comprising a compound as defined in any one of embodiments i to xxxvii together with at least one pharmaceutically acceptable carrier or excipient.

xxxix. A compound as defined in any one of embodiments i to xxxvii, or a pharmaceutical composition as defined in embodiment xxxviii for use in therapy or for use as a medicament.

xl. A compound as defined in any one of embodiments i to xxxvii, or a pharmaceutical composition as defined in embodiment xxxviii for use as an anti-neoplastic or anti-infective agent.

xli. A compound as defined in any one of embodiments i to xxxvii, or a pharmaceutical composition as defined in embodiment xxxviii for use in treating or preventing cancer.

xlii. A compound for use as defined in embodiment xli in preventing and/or retarding proliferation of tumor cells, for example in the treatment and/or prevention of any of the following cancers: acute lymphocytic leukemia (ALL), acute myeloid leukemia (AML), chronic lymphocytic leukemia (CLL), chronic myeloid leukemia (CML), breast cancer, prostate cancer, osteosarcoma, ovarian cancer, pancreatic cancer, adrenal cancer, liver cancer, bile duct cancer, bladder cancer, stomach cancer, bone cancer, neurobastoma, glioblastoma, melanoma, kidney cancer, Non-Hodgkin lymphoma, testicular cancer, multiple myeloma, brain/CNS tumors, cervical cancer, colon/rectum cancer, endometrial cancer, esophagus cancer, gallbladder cancer, gastrointestinal tumors, hodgkin disease, kaposi sarcoma, laryngeal and hypopharyngeal cancer, lung cancer, lymphoma, malignant mesothelioma, nasopharyngeal cancer, pituitary tumors, retinoblastoma, small intestine cancer, thymus cancer, thyroid cancer, or uterine sarcoma.

xliii. A compound as defined in any one of embodiments i to xxxvii, or a pharmaceutical composition as defined in embodiment xxxviii for use in treating a bacterial or fungal infection, e.g. an infection caused by *Acetobacter aurantius, Acinetobacter bitumen, Actinomyces israelii, Agrobacterium radiobacter, Agrobacterium tumefaciens, Anaplasma phagocytophilum, Azorhizobium caulinodans, Azotobacter vinelandii, viridans streptococci, Bacillus Bacillus anthracis, Bacillus brevis Bacillus cereus, Bacillus fusiformis, Bacillus lichenformis, Bacillus megaterium, Bacillus mycoides, Bacillus stearothermophilus, Bacillus subtilis, Bacillus Thuringiensis, Bacteroides Bacteroides, fragilis Bacteroides, gingivalis Bacteroides, melaninogenicus* (now known as *Prevotella melaninogenica*), *Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulo-*

*matis, Campylobacter coli, Campylobacter fetus, Campylobacter jejuni, Campylobacter pylori, Chlamydia trachomatis, Chlamydophila pneumoniae* (previously called *Chlamydia pneumoniae*), *Chlamydophila psittaci* (previously called *Chlamydia psittaci*), *Clostridium botulinum, Clostridium difficile, Clostridium perfringens* (previously called *Clostridium welchii*), *Clostridium tetani, Corynebacterium diphtheriae, Corynebacterium fusiforme, Coxiella burnetii, Diplococcus pneumoniae, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Klebsiella pneumoniae, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma gallinarum, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Porphyromonas gingivalis, Prevotella melaninogenica* (previously called *Bacteroides melaninogenicus*), *Pseudomonas aeruginosa, Rhizobium radiobacter, Rickettsia Rickettsia prowazekii, Rickettsia psittaci, Rickettsia quintana, Rickettsia rickettsii, Rickettsia trachomae, Rochalimaea, Rochalimaea henselae, Rochalimaea quintana, Rothia dentocariosa, Salmonella enteritidis, Salmonella schottmuelleri, Salmonella typhi, Salmonella typhimurium, Serratia marcescens, Shigella dysenteriae, Spirillium Volutans, Staphylococcus aureus, Staphylococcus epidermidis, Stenotrophomonas maltophilia, Streptococcus agalactiae, Streptococcus avium Streptococcus bovis, Streptococcus cricetus, Streptococcus faceium, Streptococcus faecalis Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Wolbachia, Yersinia enterocolitica, Yersinia pestis,* or *Yersinia pseudotuberculosis.* xliv. Use of a compound as defined in any one of embodiments i to xxxvii in the manufacture of a medicament for use as defined in any one of embodiments xl to xliii.xlv.

A method of treatment of a human or non-human animal body to combat or prevent cancer or to treat an infection (preferably a cancer or infection as defined in embodiment xlii or embodiment xliii), said method comprising the step of administering to said body an effective amount of a compound as defined in any one of embodiments a to xxxvii, or a pharmaceutical composition as defined in embodiment xxxviii.

The compounds according to the invention find particular use as anti-neoplastic and anti-infective agents. The invention will now be further described with reference to the following non-limiting examples:

Example 1—Synthetic Route to Iodinin 2-bromo-3-methoxyaniline
CAS 112970-44-4
Commercially available in bulk Brettphos-Pd(II) G1
Argon, $Cs_2CO_3$
KHDMS, dry toluene,
120° C., 79%

BBr3
Reflux, 5 h
100% mCPBA
argon, dry toluene,
75%

Iodinin a) Synthesis of 1,6-dimethoxyphenazine (1a)

A dry round-bottom flask with a reflux condenser was charged with 2-bromo-3-methoxyanilin (1.00 g, 4.95 mmol), KHMDS (32 mg, 0.16 mmol, 0.03 eq), BrettPhos Pd G1 Methyl-t-Butyl Ether adduct (118 mg, 0.15 mmol, 0.03 eq) and $Cs_2CO_3$ (3.22 g, 9.88 mmol, 2.0 eq). The system was sealed by a rubber septum before air was removed under reduced pressure and replaced by argon (repeated 3 times). Anhydrous toluene (20 mL) was transferred to the flask and the resulting orange coloured suspension gradually warmed up to reflux and left stirring for 24 h. The heating was removed and the crude mixture was cooled to reach rt. The reaction mixture was filtered through a funnel of Celite and undissolved material washed with DCM until no yellow solution came through the funnel. The resulting crude mixture was dry-loaded on silica and purified by flash column chromatography on silica gel (1:7 EtOAc/DCM as eluent) affording 468 mg (79%) of the yellow solid. $R_f$: 0.51 (100% EtOAc) $^1$H-NMR (400 MHz, CDCl$_3$) δ 7.94 (dd, J=8.9, 1.1 Hz, 2H), 7.67 (dd, J=8.9, 7.6 Hz, 2H), 7.02 (dd, J=7.7, 1.1 Hz, 2H), 4.11 (s, 6H). $^{13}$C-NMR (101 MHz, CDCl$_3$) δ 154.9, 143.0, 136.9, 130.1, 122.1, 106.9, 56.5. HRMS (EI): Exact mass calculated for $C_{14}H_{12}N_2O_2$: 240.0899, found 240.0894 (1.8 ppm).

$^1$H- and $^{13}$C-NMR data are in accordance with published literature: M. Weigele and W. Leimgruber, *Tetrahedron Lett,* 1967, 8, 715-718, and G. Chowdhury, U. Sarkar, S. Pullen, W. R. Wilson, A. Ajapakse, T. Fuchs-Knotts and K. S. Gates, *Chem Res Toxicol,* 2012, 25, 197-206.

b) Synthesis of 1,6-dihydroxyphenazine (1b)

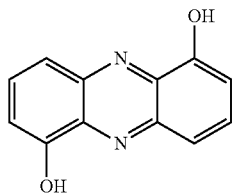 [SMILES: Oc1cccc2nc3c(O)cccc3nc12]

The procedure was performed with slight modification according to previously described method by Alonso et al. Boron tribromide (5.0 g, 20 mmol) was transferred to a dry round-bottom flask containing 1,6-dimethoxyphenazine (4) (460 mg, 1.91 mmol) and a magnetic bar under argon atm. The mixture was gradually warmed up to 91° C. and refluxed for 5 h. The mixture was cooled down to −78° C. and quenched by a drop-wise addition of ice water and allowed to reach rt. The pH of the solution was adjusted to 7 by 1.0 M NaOH. The goldenrod precipitate was filtered off and washed with cold water. The afforded crude material was dried in vacuo yielding 425 mg of 1,6-dihydroxyphenazine (>99%). No further purification was undertaken. $R_f$: 0.42 (100% EtOAc). $^1$H-NMR (600 MHz, DMSO-d$_6$) δ 10.49 (s, 2H), 7.79-7.70 (m, 4H), 7.19 (dd, J=7.2, 1.4 Hz, 2H). $^{13}$C-NMR (151 MHz, DMSO-d$_6$) δ 153.4, 142.1, 135.7, 131.3, 119.2, 110.6. $^1$H- and $^{13}$C-NMR data are in accordance with prior literature: A. Mateo Alonso, R. Horcajada, H. J. Groombridge, R. Chudasama, M. Motevalli, J. H. P. Utley and P. B. Wyatt, *Organic & Biomolecular Chemistry,* 2005, 3, 2832-2841.

c) Synthesis of 1,6-dihydroxyphenazine 5,10-dioxide (1c, iodinin)

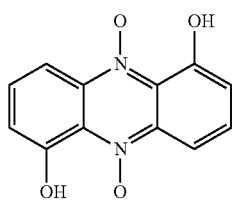

A dry round bottomed flask (with a reflux condenser) was loaded with 1,6-dihydroxyphenazine (1.23 g, 3.79 mmol) at rt under argon atm. The goldenrod solid was suspended in 100 mL of anhydrous toluene and stirred for 15 min at rt. mCPBA (2.0 g, ≤77% purity; Sigma-Aldrich) was added before the mixture was shielded from light and gradually warmed to 80° C. and added 0.8 g mCPBA in pulses every h (i.e. repeated 4 times). After 5 h at 80° C., 1.0 g of mCPBA was added and the reaction mixture stirred for additional 60 min. The reaction mixture was cooled down on ice bath before it was concentrated in vacuo to a dark and slurry crude material. The resulting crude product was dispersed in MeOH/Et$_2$O (1:1) and filtered on a filter paper in relatively small portions. Each portion was roughly washed by 20 mL NaHCO$_3$ (saturated aqueous sol.), 20 mL MeOH and 20 mL Et$_2$O. These portions were collected and combined and washed again by saturated sol. of NaHCO$_3$ (200 mL), H$_2$O (50 mL), MeOH (200 mL) and Et$_2$O (200 mL) or until a homogenous dark-purple color was obtained and clear transparent solvent runs through the filter paper. The remaining product was collected from the filter paper and the product was dried in vacuo affording 938 mg (76%) of 1 as a deep-purple solid with a cuppery luster. No further purification was necessary. $R_f$: 0.61 (100% DCM). $^1$H-NMR (600 MHz, DMSO-d$_6$) δ 14.25 (s, 2H), 7.92 (dd, J=9.0, 1.1 Hz, 2H), 7.82 (dd, J=9.0, 7.8 Hz, 2H), 7.19 (dd, J=7.8, 1.1 Hz, 2H). $^{13}$C-NMR (151 MHz, DMSO-d$_6$) δ 152.5, 135.0, 133.4, 126.7, 114.0, 107.4. HRMS (EI): Exact mass calculated for $C_{12}H_8N_2O_4$: 244.0484, found 244.0487 (−1.2 ppm). $^1$H- and $^{13}$C-NMR spectral data are in accordance with prior literature: H. Sletta, K. F. Degnes, L. Herfindal, G. Klinkenberg, E. Fjaervik, K. Zahlsen, A. Brunsvik, G. Nygaard, F. L. Aachmann, T. E. Ellingsen, S. O. Doskeland and S. B. Zotchev, *Appl Microbiol Biotechnol,* 2014, 98, 603-610.

Example 2: General Procedure for the Synthesis of 1-Methoxyphenazines 7,8-substituted phenazines were synthesized according to procedures published in the prior art by Cushman et al in J. Med. Chem. 2010, 53, 8688-8699 and Huigens III in *Angew. Chem. Int. Ed.* 2015, 54, 14819-14823.

A dry round bottomed flask was charged with 3-methoxychatechol (10-20 mmol, under argon atm. Anhydrous Et$_2$O was added (30-60 mL) at room temp and stirred until a clear solution was obtained. This solution was cooled down to −78° C. before O-chloranil (12.5-25 mmol) was added. The temperature (−78° C.) was maintained for 4 h. The resulting crude mixture was filtered twice using a filter paper on a Buchner funnel. The dark crude material obtained was washed with cold ether (−78° C.) and left to dry for 10 min. The solid crude was then transferred to 250 mL round bottom flask containing a solution of the corresponding orthodiphenylamine (2a-e) in 1:1 PhMe/AcOH. The afforded mixture was stirred for 20-24 h at room temperature. The mixture was concentrated in vacuo to a dark slurry material before the mixture was carefully neutralized using NaHCO$_3$ saturated aqueous solution (250-500 mL). Before transferring to a separatory funnel for extraction, the obtained solution was filtered and the remaining residues on top washed with DCM (100 mL). The organic phase was separated and the aqueous phase extracted with DCM (4×50 mL). Combined organic phases were dried over MgSO$_4$ and filtered. The resulting solution of crude compound was absorbed onto silica gel.

Example 2a: Preparation of 1-Methoxyphenazine

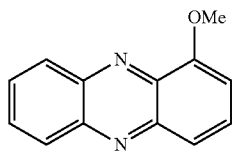 [SMILES: COc1cccc2nc3ccccc3nc12]

Synthesized according to the general procedure in Example 2. Flash column chromatography on silica (100% DCM) afforded 787 mg (60%) of the yellow solid. $R_f$: 0.41 (1:7 EtOAc/DCM). $^1$H NMR (400 MHz, Chloroform-d) δ 8.43-8.35 (m, 1H), 8.27-8.20 (m, 1H), 7.90-7.79 (m, 3H), 7.75 (dd, J=8.9, 7.5 Hz, 1H), 7.07 (dd, J=7.5, 1.1 Hz, 1H), 4.18 (s, 3H). $^{13}$C NMR (101 MHz, CDCl$_3$) δ 155.3, 144.3, 143.6, 142.4, 137.1, 131.0, 130.7, 130.4, 130.3, 129.4, 121.5, 106.6, 56.6. $^1$H and $^{13}$C NMR data are in accordance with literature.

Example 2b: Preparation of 1-methoxy-7,8-dimethylphenazine

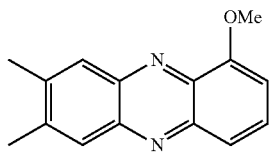 [SMILES: COc1cccc2nc3cc(C)c(C)cc3nc12]

Synthesized according to the general procedure in Example 2. Flash column chromatography on silica (100% DCM) afforded 280 mg (24%) of the yellow solid. $R_f$: 0.47 (10% EtOAc/DCM). $^1$H NMR (400 MHz, CDCl$_3$) δ 8.11 (s, 1H), 7.92 (s, 1H), 7.77 (dd, J=8.9, 1.1 Hz, 1H), 7.66 (dd, J=8.8, 7.5 Hz, 1H), 6.99 (dd, J=7.6, 1.1 Hz, 1H), 4.13 (s, 3H), 2.51 (s, 6H). $^{13}$C NMR (101 MHz, CDCl$_3$) δ 155.3, 143.9, 143.0, 142.3, 141.8, 141.5, 136.5, 129.8, 128.7, 127.7, 121.4, 106.1, 56.5, 20.8, 20.7. $^1$H and $^{13}$C NMR data are in accordance with literature.

Example 2c: Preparation of 1-methoxybenzo[b]phenazine

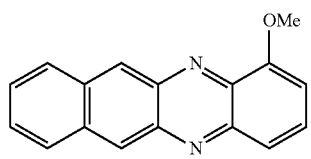 [SMILES: COc1cccc2nc3cc4ccccc4cc3nc12]

Synthesized according to the general procedure in Example 2. Flash column chromatography on silica 0-10% EtOAc/DCM) afforded 1551 mg (78%) of red solid. $R_f$: 0.13 (DCM). $^1$H NMR (400 MHz, Chloroform-d) δ 9.06 (s, 1H), 8.86 (s, 1H), 8.16-8.04 (m, 2H), 7.80 (dd, J=9.0, 1.2 Hz, 1H), 7.70 (dd, J=9.0, 7.4 Hz, 1H), 7.55-7.45 (m, 2H), 6.97 (d, J=7.4 Hz, 1H), 4.19 (s, 3H). $^{13}$C NMR (101 MHz, CDCl$_3$) δ 155.3, 145.3, 140.1, 139.0, 138.7, 135.0, 134.5, 131.0, 128.9, 128.7, 127.4, 127.2, 126.9, 121.9, 105.9, 56.6. $^1$H and $^{13}$C NMR data are in accordance with literature.

Example 2d: Preparation of 1-methoxy-7,8-dichlorophenazine

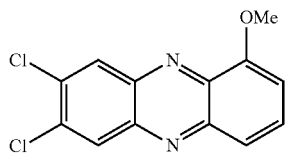 [SMILES: COc1cccc2nc3cc(Cl)c(Cl)cc3nc12]

Synthesized according to the general procedure in Example 2. Flash column chromatography on silica (100% DCM) affording 953 mg 45% of a yellow solid. $R_f$: 0.17 (100% DCM). $^1$H NMR (400 MHz, CDCl$_3$) δ 8.54 (s, 1H), 8.37 (s, 1H), 7.83-7.75 (m, 2H), 7.10 (dd, J=5.7, 3.0 Hz, 1H), 4.18 (s, 3H). $^{13}$C NMR (101 MHz, CDCl$_3$) δ 155.3, 144.6, 142.0, 140.7, 137.4, 136.1, 135.3, 131.8, 130.5, 129.6, 121.5, 107.4, 56.7. $^1$H and $^{13}$C NMR data are in accordance with literature.

Example 2e: Preparation of 1-methoxy-7,8-dibromophenazine

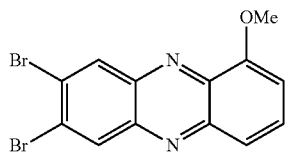 [SMILES: COc1cccc2nc3cc(Br)c(Br)cc3nc12]

Synthesized according to the general procedure in Example 2. Flash column chromatography on silica (0-10% EtOAc/DCM) affording 1.34 g 73% of a yellow solid. RJ: 0.68 (10% EtOAc/DCM). $^1$H NMR (400 MHz, Chloroform-d) δ 8.74 (s, 1H), 8.56 (s, 1H), 7.85-7.73 (m, 2H), 7.09 (dd, J=5.0, 3.6 Hz, 1H), 4.17 (s, 3H). $^{13}$C NMR (101 MHz, CDCl$_3$) δ 155.3, 144.8, 142.5, 141.1, 137.4, 134.0, 133.2, 131.8, 128.1, 127.3, 121.6, 107.4, 56.7. $^1$H and $^{13}$C NMR data are in accordance with literature.

Example 3: General Procedure for Synthesis of 1-hydroxyphenazines

Boron tribromide (5 g, 20 mmol) was transferred to a dry round bottom flask containing a methoxyphenazine of choice described in Examples 2a-2e under argon atm. The mixture was gradually warmed up to reflux and kept at that temperature for 5 hours. The mixture was cooled down on ice bath and quenched carefully by drop wise addition of H$_2$O. The pH of the aqueous mixture was adjusted to ~7 by 1M NaOH aqueous sol. The precipitated crude product was filtered and washed with cold H$_2$O. If necessary, the filtered crude product was further purified by flash column chromatography or recrystallization from appropriate solvent.

Example 3a: Preparation of Phenazine-1-ol

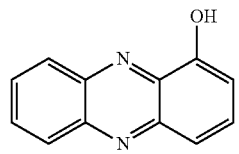 [SMILES: Oc1cccc2nc3ccccc3nc12]

Synthesized according to the general procedure in Example 3. If necessary after filtration of the crude product, Flash column chromatography on silica or recrystallization from appropriate mixture of solvents can be employed in order to obtain the purified product.

Example 3b: Preparation of 7,8-dimethylphenazin-1-ol

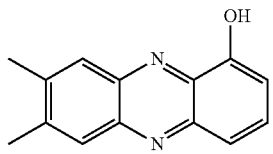 [SMILES: Cc1cc2nc3cccc(O)c3nc2cc1C]

Synthesized according to the general procedure in Example 3. Obtained filtrate was further purified by flash column chromatography on silica (0-10% EtOAC/DCM) which afforded 202 mg (87%) of a yellow solid. $R_f$: 0.56 (15% EtOAc/DCM). $^1$H NMR (400 MHz, CDCl$_3$) δ 8.20 (s, 1H), 7.99 (s, 1H), 7.93 (s, 1H), 7.80-7.64 (m, 2H), 7.19 (dd, J=7.1, 1.5 Hz, 1H), 2.55 (s, 6H). $^{13}$C NMR (101 MHz, CDCl$_3$) δ 151.8, 143.5, 143.2, 142.5, 142.1, 140.7, 134.3, 131.2, 128.0, 127.6, 119.8, 108.6, 20.9, 20.8.

Example 3c: Preparation of Benzo[b]phenazin-1-ol

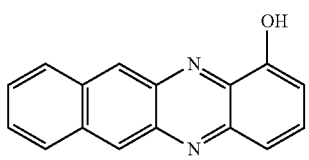 [SMILES: Oc1cccc2nc3cc4ccccc4cc3nc12]

After the filtrate was obtained according to general procedure 2, the crude product was filtered and washed with H$_2$O. Flash column chromatography on silica (0-10% EtOAc/DCM) afforded 837 mg (88%) of the cherry-red solid. $R_f$: 0.40 (100% DCM). $^1$H NMR (400 MHz, DMSO-d6) δ 10.63 (s, 1H), 9.03 (d, J=1.1 Hz, 1H), 8.97 (d, J=1.1 Hz, 1H), 8.36-8.19 (m, 2H), 7.77 (dd, J=9.0, 7.3 Hz, 1H), 7.68 (dd, J=8.9, 1.2 Hz, 1H), 7.66-7.55 (m, 2H), 7.14 (dd, J=7.3, 1.2 Hz, 1H). $^{13}$C NMR (101 MHz, DMSO) δ 153.3, 144.8, 139.5, 137.9, 137.6, 134.2, 133.8, 132.5, 128.5, 128.3, 127.5, 127.1, 127.1, 126.9, 119.4, 109.6.

Example 3d: Preparation of 7,8-dichlorophenazin-1-ol

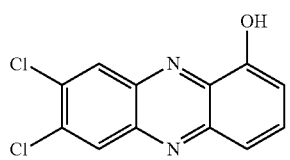 [SMILES: Oc1cccc2nc3cc(Cl)c(Cl)cc3nc12]

After the filtrate was obtained according to general procedure 2, it was washed with H$_2$O and EtOH before dried under vacuum. Orange solid was obtained (510 mg, >99%). $^1$H NMR (600 MHz, DMSO-d6) δ 10.79 (s, 1H), 8.58 (s, 1H), 8.55 (s, 1H), 7.85 (dd, J=8.8, 7.5 Hz, 1H), 7.69 (dd, J=8.8, 1.1 Hz, 1H), 7.24 (dd, J=7.5, 1.2 Hz, 1H). $^{13}$C NMR (151 MHz, DMSO) δ 153.7, 144.2, 141.5, 139.8, 136.3, 134.0, 133.2, 133.2, 130.0, 129.8, 119.0, 111.4.

Example 3e: Preparation of 7,8-dibromophenazin-1-ol

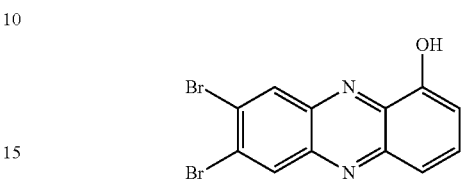

After the filtrate was obtained according to general procedure 2, the crude product was filtered and washed with H$_2$O and dried affording a beige solid (721 mg, 93%). For characterization, small amount was recrystallized from boiling CHCl$_3$ and filtered. $^1$H NMR (600 MHz, DMSO-d6) δ 10.77 (s, 1H), 8.69 (s, 1H), 8.67 (s, 1H), 7.84 (dd, J=8.8, 7.5 Hz, 1H), 7.67 (dd, J=8.8, 1.2 Hz, 1H), 7.24 (dd, J=7.5, 1.2 Hz, 1H). $^{13}$C NMR (151 MHz, DMSO) δ 153.7, 144.2, 141.9, 140.2, 136.3, 133.2, 133.2, 133.0, 126.9, 126.1, 119.0, 111.4.

Example 4—General procedure for synthesis of 1-hydroxyphenazine 5,10-dioxides

A dry round bottomed flask with a reflux condenser is loaded with appropriate 1-hydroxyphenazine described in example 3a-3e (0.2-5 mmol, 1 equiv) and dissolved in Toluene 20-200 mL under argon atm at room temperature. mCPBA, ≤77% purity; Sigma-Aldrich (2 molar equivalents) was added and before the mixture is shielded from light and gradually warmed to 80° C. After 60 min from first addition, mCPBA was added (1 molar equivalent). The addition of mCPBA was repeated every hour for the next 2 following hours. After 4 h reaction time, mCPBA (1.5 molar equivalents) was added for the last time and the reaction mixture stirred for 1 additional hour. Upon cooldown, the reaction mixture was concentrated to a slurry dark crude material in vacuo. The obtained crude was dispersed in ice-cold MeOH (30-40 mL) and filtered. The afforded filtrate was washed by NaHCO$_3$ (40-100 mL sat. aqueous sol.), H$_2$O (40-100 mL), followed by ice-cold MeOH and Et$_2$O (40-100 and 20-80 mL each). The collected crude material was further purified as stated below for each individual compound.

Example 4a: Preparation of 1-hydroxyphenazine 5,10-dioxide

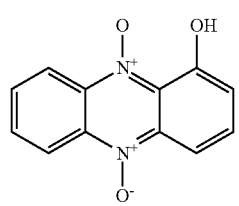 [SMILES: [O-][n+]1c2ccccc2[n+](O)c2c(O)cccc21]

Synthesized in accordance with the general procedure in Example 4. Flash column chromatography on silica (0-2%

MeOH/DCM) affording 131 mg (64%) of the dark red solid. $R_f$: 0.74 (1% MeOH/DCM). $^1$H-NMR (400 MHz, Chloroform-d) δ 14.48 (s, 1H), 8.69-8.59 (m, 2H), 8.06 (dd, J=9.0, 1.1 Hz, 1H), 7.89-7.77 (m, 2H), 7.68 (dd, J=9.0, 7.9 Hz, 1H), 7.14 (dd, J=7.9, 1.1 Hz, 1H). $^{13}$C-NMR (101 MHz, CDCl$_3$) δ 154.1, 137.5, 136.1, 133.8, 133.0, 131.8, 131.7, 126.6, 120.1, 119.4, 114.7, 108.7. HRMS (ESI+): Exact mass calculated for $C_{12}H_8N_2O_3$ Na [M+Na]+: 251.0427, found 251.0427 (0.1 ppm).

Example 4b: Preparation of 1-hydroxy-7,8-dimethylphenazine 5,10-dioxide

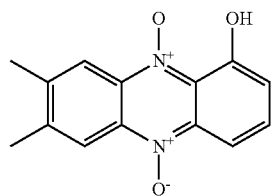 [SMILES: Cc1cc2c(cc1C)[n+](O)c1c(O)cccc1[n+]2[O-]]

Synthesized in accordance with the general procedure in Example 4. Flash column chromatography on silica (0-1% MeOH/DCM) afforded 185 mg (79%) of a brown solid. $R_f$: 0.22 (1% MeOH/DCM). $^1$H NMR (400 MHz, Chloroform-d) δ 14.52 (broad s, 1H), 8.40 (s, 1H), 8.38 (s, 1H), 8.05 (dd, J=9.0, 1.1 Hz, 1H), 7.65 (dd, J=8.9, 7.9 Hz, 1H), 7.11 (dd, J=7.9, 1.1 Hz, 1H), 2.57-2.51 (m, 6H). $^{13}$C NMR (101 MHz, CDCl$_3$) δ 154.0, 143.9, 143.7, 137.0, 134.7, 132.5, 132.4, 126.0, 118.7, 117.8, 114.2, 108.6, 20.8, 20.8.

Example 4c: Preparation of 1-hydroxybenzo[b]phenazine 5,12-dioxide

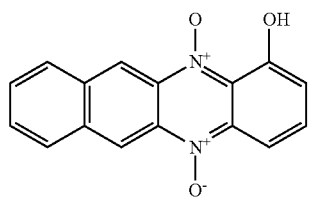 [SMILES: [O-][n+]1c2cc3ccccc3cc2[n+](O)c2c(O)cccc21]

Synthesized in accordance with the general procedure in Example 4. Flash column chromatography on silica afforded 126 mg (30%) of the dark-blue solid. $R_f$: 0.22 (100% DCM). $^1$H NMR (600 MHz, DMSO-d6) δ 14.80 (s, 1H), 9.30 (s, 1H), 9.24 (s, 1H), 8.38 (dt, J=6.8, 3.6 Hz, 2H), 7.92 (dd, J=9.1, 1.0 Hz, 1H), 7.77-7.66 (m, 3H), 7.09 (dd, J=7.7, 1.0 Hz, 1H). $^{13}$C NMR (151 MHz, DMSO) δ 152.87, 136.48, 133.81, 133.76, 133.47, 132.23, 131.32, 129.01, 128.84, 128.78, 126.63, 118.50, 118.14, 112.77, 108.18.

Example 4d: Preparation of 7,8-dichloro-1-hydroxyphenazine 5,10-dioxide

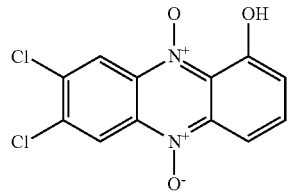

Synthesized in accordance with the general procedure in Example 4. Flash column chromatography (pure DCM) afforded crude material which was further purified by NaHCO$_3$/H$_2$O, MeOH and Et$_2$O (30 mL each) wash on a filter paper under vacuum and dried. This afforded 120 mg (31%) of a deep purple solid. $R_f$: 0.35 (DCM). $^1$H NMR (600 MHz, Chloroform-d) δ 14.29-13.96 (m, 1H), 8.80 (d, J=6.7 Hz, 2H), 8.06 (d, J=8.9 Hz, 1H), 7.79-7.63 (m, 1H), 7.20 (d, J=7.3 Hz, 1H). HRMS (ESI+): Exact mass calculated for $C_{12}H_6Cl_2N_2O_3$Na [M+Na]$^+$: 318.9648, found 318.9647 (0.4 ppm).

Example 4e: Preparation of 7,8-dibromo-1-hydroxyphenazine 5,10-dioxide

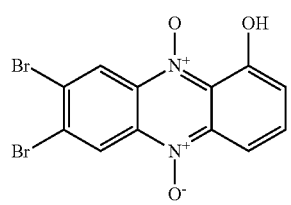

Synthesized in accordance with the general procedure in Example 4. Flash column chromatography (pure DCM) afforded crude material which was further purified by NaHCO$_3$/H$_2$O, MeOH and Et$_2$O (30 mL each) wash on a filter paper under vacuum and dried. The procedure afforded 143 mg (44%) of a deep purple solid. $^1$H NMR (600 MHz, Chloroform-d) δ 14.12 (s, 1H), 8.97 (d, J=1.1 Hz, 1H), 8.96 (d, J=1.1 Hz, 1H), 8.05 (d, J=9.0 Hz, 1H), 7.73 (ddd, J=9.0, 7.9, 1.2 Hz, 1H), 7.20 (dt, J=7.8, 1.2 Hz, 1H). $^{13}$C NMR (151 MHz, CDCl$_3$) δ 154.1, 137.8, 134.7, 133.6, 132.5, 130.2, 130.0, 126.7, 124.3, 123.7, 115.6, 109.0.

Example 5: General Procedure for the O-alkylation of 1,6-dihydroxyphenazine 5,10-dioxide (iodinin)

A dry round-bottom flask is charged with 1-hydroxy-6-methoxyphenazine 5.10-dioxide (iodinin, 0.1-1 mmol, 1.0 eq), K$_2$CO$_3$ (0.15-1.15 mmol, 1.5 eq) and 18-Crown-6 (0.15-1.5 mmol, 1.5 eq). The solids were dispersed in anhydrous DMF or THF (5-50 mL) under argon atm and shielded from light. After 15 min of stirring the resulting mixture had switched colour from dark violet towards emerald green, a drop wise addition of alkyl halide (0.1-5 mmol, 1-5 molar equivalents) of choice was carried out drop-wise before the mixture was left stirring for additional period of 1-24 h at rt. The reaction mixture was concentrated in vacuo, diluted with NH$_4$Cl (0.1-0.5 L 10% aqueous sol.) and the aqueous phase extracted by organic solvent of choice (4×30 mL EtOAc, or DCM). The pooled organic phases were washed with brine (100-400 mL), dried over MgSO$_4$, filtered and concentrated in vacuo before further purification by flash column chromatography on silica is performed as stated for each individual compound.

Example 5a: Synthesis of 1-hydroxy-6-methoxyphenazine 5.10-dioxide (Myxin)

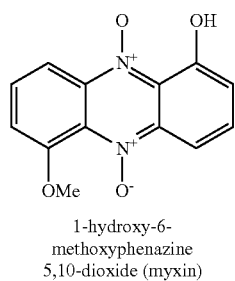 [SMILES: COc1cccc2c1[n+]([O-])c1cccc(O)c1[n+]2O]

1-hydroxy-6-methoxyphenazine 5,10-dioxide (myxin)

Synthesized in accordance with the general procedure in Example 5 using MeI as an alkyl halide. The resulting crude mixture was dry-loaded on silica and further purified by flash column chromatography on silica gel (20-80% EtOAc/Heptan as eluent) to afford 175 mg (72%) of myxin (2) as a bright cherry-red solid. R$_f$: 0.59 (100% EtOAc). $^1$H-NMR (600 MHz, CDCl$_3$) δ 14.59 (broad s, 1H), 8.24 (dd, J=9.1, 1.1 Hz, 1H), 8.03 (dd, J=9.0, 1.1 Hz, 1H), 7.68 (dd, J=9.1, 8.0 Hz, 1H), 7.63 (dd, J=9.1, 7.9 Hz, 1H), 7.12 (dd, J=7.9, 1.1 Hz, 1H), 7.08 (dd, J=8.0, 1.0 Hz, 1H), 4.09 (s, 3H). $^{13}$C-NMR (151 MHz, CDCl$_3$) δ 153.9, 153.8, 138.8, 136.0, 132.6, 131.8, 130.0, 126.0, 115.0, 110.7, 109.9, 109.0, 57.4. HRMS (EI): Exact mass calculated for C$_{13}$H$_{10}$N$_2$O$_4$: 258.0641, found 258.0643 (−0.8 ppm).

$^1$H and $^{13}$C NMR data are in accordance with literature (Chowdhury et al., *Chemical Research in Toxicology* 2011, 25 (1), 197-206).

Example 5b: Preparation of 1-(2-(tert-butoxy)-2-oxoethoxy)-6-hydroxyphenazine 5,10-dioxide

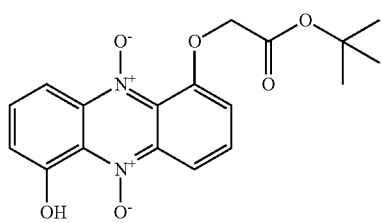 [SMILES: CC(C)(C)OC(=O)COc1cccc2c1[n+]([O-])c1cccc(O)c1[n+]2[O-]]

Synthesized in accordance with the general procedure in Example 5 using tert-butyl bromoacetate as an alkylating agent. Flash column chromatography on silica (10-25% EtOAc/Heptane) afforded 99 mg (43%) of the deep-red solid. R$_f$: 0.78 (100% EtOAc). $^1$H-NMR (300 MHz, Chloroform-d) δ 14.54 (s, 1H), 8.30 (dd, J=9.1, 1.1 Hz, 1H), 8.02 (dd, J=9.0, 1.1 Hz, 1H), 7.63 (ddd, J=9.0, 7.9, 4.8 Hz, 2H), 7.11 (dd, J=7.9, 1.1 Hz, 1H), 7.06 (dd, J=7.9, 0.9 Hz, 1H), 4.77 (s, 2H), 1.50 (s, 9H). $^{13}$C-NMR (151 MHz, CDCl$_3$) δ 166.8, 153.8, 151.9, 138.9, 136.0, 132.6, 131.4, 130.4, 126.0, 115.0, 113.4, 112.4, 109.1, 83.1, 68.2, 28.2. HRMS (TOF ES+): Exact mass calculated for C$_1$H$_1$N$_2$O$_6$ Na [M+Na]$^+$: 381.1062, found 381.1058.

Example 5c: Preparation of 1-(2-(ethoxy)-2-oxoethoxy)-6-hydroxyphenazine 5,10-dioxide

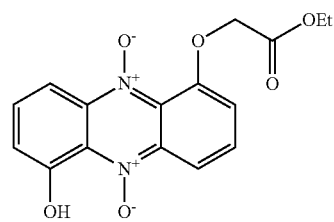 [SMILES: CCOC(=O)COc1cccc2c1[n+]([O-])c1cccc(O)c1[n+]2[O-]]

Synthesized in accordance with the general procedure in Example 5 using ethyl bromoacetate as an alkylating reagent. Flash column chromatography on silica (20-50% EtOAc in Heptane) afforded 16 mg (12%) of the red solid. $^1$H NMR (600 MHz, Chloroform-d) δ 14.52 (s, 1H), 8.34 (dd, J=9.1, 1.1 Hz, 1H), 8.03 (dd, J=9.1, 1.1 Hz, 1H), 7.64 (dt, J=9.0, 7.8 Hz, 2H), 7.13 (dd, J=7.8, 1.1 Hz, 2H), 4.88 (s, 2H), 4.31 (q, J=7.1 Hz, 2H), 1.32 (t, J=7.1 Hz, 3H). $^{13}$C NMR (151 MHz, CDCl$_3$) δ 167.94, 153.89, 151.67, 138.95, 135.97, 132.70, 131.35, 130.64, 126.03, 115.09, 114.58, 113.05, 109.02, 68.38, 61.87, 14.34. HRMS (TOF ES$^+$): Exact mass calculated for C$_{16}$H$_{14}$N$_2$O$_6$Na [M+Na]$^+$: 353.0749, found 353.0745 (−1.29 ppm).

Example 5d: Preparation of 1-Acetoxy-6-hydroxyphenazine 5,10-dioxide

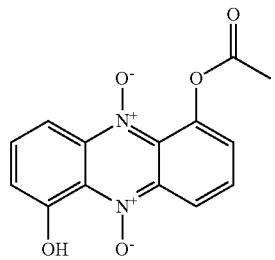

Molecular Weight: 286.24

The compound was prepared according to the procedure in Example 5e.

Example 5e: Preparation of 1-Acetoxy-6-methoxyphenazine 5,10-dioxide

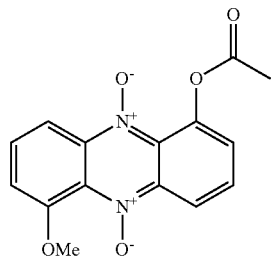 [SMILES: COc1cccc2c1[n+]([O-])c1cccc(OC(C)=O)c1[n+]2[O-]]

In a dry round bottom flask with a magnetic stir bar under argon atm, myxin (20 mg, 0.77 mmol 1 equiv.), N-(3-Dimethylaminopropyl)-N-ethylcarbodiimide hydrochloride (EDC-HCl)(3.08 mmol, 4 equiv.) and acetic acid (5.0 µL, 0.31 mmol, 4 equiv) were dissolved in DCM:THF/7:3 (1.5 mL). After 5 minutes, DMAP (4-dimetylaminopyridin, 0.25 equiv, 0.19 mmol) was added and the resulting mixture stirred for 3 hours at room temperature. The mixture was filtered through a plug of Celite using DCM as eluent and the resulting filtered solution concentrated in vacuo. Flash column chromatography on silica (0-50% EtOAc in DCM) afforded 17 mg (73%) of an orange solid. $R_f$: 0.17 (100% EtOAc). $^1$H NMR (600 MHz, CDCl$_3$) δ 8.60 (dd, J=9.1, 1.2 Hz, 1H), 8.20 (dd, J=9.0, 0.9 Hz, 1H), 7.65 (dd, J=9.1, 7.5 Hz), 7.60 (dd, J=9.0, 8.0 Hz, 1H), 7.32 (dd, J=7.5, 1.2 Hz, 1H), 7.06 (d, J=8.0 Hz, 1H), 4.05 (s, 3H), 2.48 (s, 3H). $^{13}$C NMR (151 MHz, CDCl$_3$) δ 169.5, 153.9, 142.8, 139.5, 139.1, 131.2, 130.3, 129.9, 129.6, 124.4, 118.8, 111.7, 110.3, 57.3, 21.1. HRMS (EI): Exact mass calculated for $C_{15}H_{12}N_2O_5$:300.0746, found 300.0751 (−1.5 ppm).

Example 6: General procedure for the alkylation of 1-hydroxyphenazine 5,10-dioxide, 7,8-disubstituted 1-hydroxyphenazine 5,10-dioxide Derivatives, and Myxin Derivatives

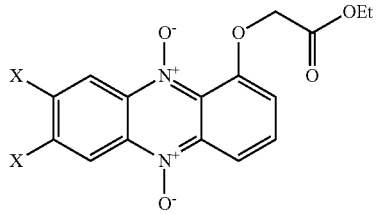

X = H, X = CH$_3$, X = Cl, X = Br,

A dry round bottomed flask was charged with any 1-hydroxyphenazine 5.10-dioxide or myxin (0.30 mmol, 1.0 eq), K$_2$CO$_3$ (0.45 mmol, 1.5 eq) and 18-Crown-6 (0.45 mmol, 1.5 eq) and a magnetic stir bar at room temperature. The mixture of solids was dispersed in DMF (5-10 mL anhydrous) and allowed to stir for 15 min before a corresponding electrophile (3 eq, 0.90 mmol of either methyl iodide, dimethyl sulfate, ethyl bromoacetate, tertbutyl-bromoacetate or 2-chloro-N,N-diethylacetamide) was added. In cases where 2-chloro-N,N-diethylacetamide was used, KI (0.09 mmol, 0.3 eq) was also added and the mixture left to stir overnight. In cases where bromoacetates were used, the resulting mixture was left stirring for 2-5 h at room temperature (depending on TLC). If starting material was still present after 3-4 hours (TLC analysis, 2-5% MeO), K$_2$CO$_3$ (0.23 mmol, 0.75 eq), 18-Crown-6 (0.23 mmol, 0.75 eq) and a corresponding bromoacetate (0.45 mmol, 1.5 eq) were added. The mixture was diluted with H$_2$O (50 mL) and HCl (~1 mL 1M aqueous sol.). The aqueous phase was extracted with DCM (3×30 mL or until no or very faint color was extracted from the aqueous phase). Pooled organic phases were washed with brine, dried over MgSO$_4$ and filtered before concentrated in vacuo. Further purification was undertaken as stated below for each individual compound.

Example 6a: Preparation of 1-(2-ethoxy-2-oxoethoxy)phenazine 5,10-dioxide

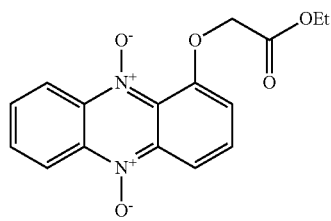 [SMILES: CCOC(=O)COc1cccc2c1[n+]([O-])c1ccccc1[n+]2[O-]]

Synthesized according to the general procedure in Example 6. Flash column chromatography on silica (2-5% MeOH/DCM) afforded 71 mg (81%) of the red solid. R. 0.46 (5% MeOH/DCM). $^1$H-NMR (400 MHz, Chloroform-d) δ 8.66 (td, J=8.2, 1.8 Hz, 2H), 8.41 (dd, J=9.1, 1.2 Hz, 1H), 7.84-7.72 (m, 2H), 7.62 (dd, J=9.1, 7.8 Hz, 1H), 7.14 (dd, J=7.8, 1.2 Hz, 1H), 4.88 (s, 2H), 4.29 (q, J=7.2 Hz, 2H), 1.31 (s, 3H). $^{13}$C-NMR (101 MHz, CDCl$_3$) δ 168.1, 151.9, 138.4, 137.6, 135.7, 131.7, 131.1, 130.8, 130.8, 120.7, 120.2, 115.1, 114.3, 68.6, 61.7, 14.3. HRMS (ESI+): Exact mass calculated for $C_{16}H_{14}N_2O_5Na$ [M+Na]$^+$: 337.0795, found 337.0795 (−0.1 ppm).

Example 6b: Preparation of 1-(2-ethoxy-2-oxoethoxy)-7,8-dimethylphenazine 5,10-dioxide

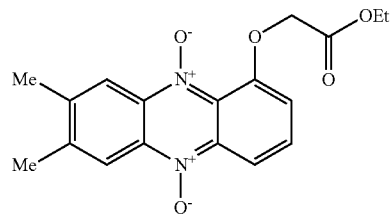 [SMILES: CCOC(=O)COc1cccc2c1[n+]([O-])c1cc(C)c(C)cc1[n+]2[O-]]

Synthesized according to the general procedure in Example 6. Flash column chromatography on silica (0-1% MeOH/DCM) afforded 185 mg (79%) of a brown solid. $R_f$: 0.22 (1% MeOH/DCM). $^1$H NMR (400 MHz, Chloroform-d) δ 14.52 (broad s, 1H), 8.40 (s, 1H), 8.38 (s, 1H), 8.05 (dd, J=9.0, 1.1 Hz, 1H), 7.65 (dd, J=8.9, 7.9 Hz, 1H), 7.11 (dd, J=7.9, 1.1 Hz, 1H), 2.57-2.51 (m, 6H). $^{13}$C NMR (101 MHz, CDCl$_3$) δ 154.0, 143.9, 143.7, 137.0, 134.7, 132.5, 132.4, 126.0, 118.7, 117.8, 114.2, 108.6, 20.8, 20.8.

Example 6c: Preparation of 7,8-dichloro-1-(2-ethoxy-2-oxoethoxy)phenazine 5,10-dioxide

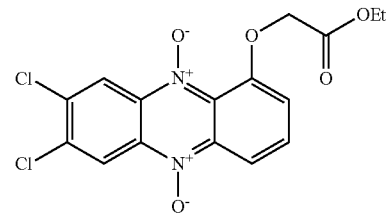 [SMILES: CCOC(=O)COc1cccc2c1[n+]([O-])c1cc(Cl)c(Cl)cc1[n+]2[O-]]

Synthesized according to the general procedure in Example 6. Flash column chromatography on silica (0-10% EtOAc/DCM) afforded 42 mg (95%) of a red solid. $R_f$: 0.27 (10% EtOAc/DCM). $^1$H NMR (400 MHz, Chloroform-d) δ 8.79 (s, 1H), 8.78 (s, 1H), 8.37 (dd, J=9.1, 1.2 Hz, 1H), 7.66 (dd, J=9.1, 7.9 Hz, 1H), 7.15 (dd, J=7.9, 1.2 Hz, 1H), 4.88 (s, 2H), 4.31 (q, J=7.1 Hz, 2H), 1.32 (t, J=7.1 Hz, 3H). $^{13}$C NMR (101 MHz, CDCl$_3$) δ 167.89, 152.03, 138.80, 137.80, 137.05, 135.85, 134.10, 131.50, 130.99, 121.93, 121.35, 115.20, 114.18, 77.16, 68.41, 61.88, 14.33. HRMS (ESI+): Exact mass calculated for $C_{16}H_{12}Cl_2N_2O_5Na$ [M+Na]$^+$: 405.0015, found 405.0015 (0.0 ppm).

Example 6d: Preparation of 7,8-dibromo-1-(2-ethoxy-2-oxoethoxy)phenazine 5,10-dioxide

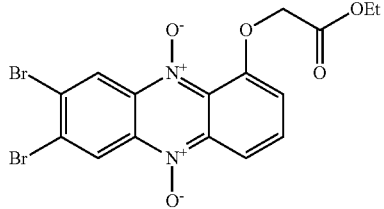

Synthesized according to the general procedure in Example 6. Flash column chromatography on silica (10% EtOAc/DCM) afforded 71 mg (over 100%). $R_f$=0.36 (10% EtOAc/DCM). $^1$H NMR (400 MHz, Chloroform-d) δ 8.95 (s, 1H), 8.95 (s, 1H), 8.37 (dd, J=9.1, 1.2 Hz, 1H), 7.66 (dd, J=9.1, 7.9 Hz, 1H), 7.15 (dd, J=7.9, 1.2 Hz, 1H), 4.31 (q, J=7.2 Hz, 2H), 1.32 (t, J=7.1 Hz, 3H). $^{13}$C NMR (101 MHz, CDCl$_3$) δ 168.0, 152.1, 138.8, 136.3, 134.5, 131.5, 131.0, 130.0, 129.1, 125.2, 124.6, 115.3, 114.2, 68.5, 61.9, 14.3.

Example 7: Synthesis of 1-(carboxymethoxy)-6-hydroxyphenazine 5,10-dioxide

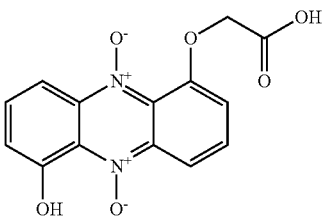 [SMILES: O=C(O)COc1cccc2c1[n+]([O-])c1cccc(O)c1[n+]2[O-]]

1-(2-(tert-butoxyl-2-oxoethoxy)-6-hydroxyphenazine 5.10-dioxide (87 mg, 0.08 mmol) from Example 5b was dissolved in 5 mL DCM. The red solution was cooled on ice bath and 1 mL H$_3$PO$_4$ (85% v/w aqueous sol.) added dropwise. The resulting mixture was stirred at 0° C. for 1 h before 1 mL of H$_3$PO$_4$ was added again. The resulting dispersion was left stirring over night at rt. The crude mixture was neutralized and pH adjusted to ~8 by NaHCO$_3$ (saturated aqueous sol.). The red aqueous phase was washed with DCM (3×20 mL, or until no color was observed within the organic phase). The resulting aqueous phase was collected and pH adjusted to 1 by HCl (37% w/w aqueous sol.) The red precipitate was filtered, washed with H$_2$O (50 mL), MeOH (20 mL) and Et$_2$O (40 mL). The filtered product was collected affording 67 mg (92%) of the dark-red solid. No further purification was necessary. RJ: not determined. $^1$H NMR (400 MHz, DMSO-d6) δ 14.93 (s, 1H), 13.17 (s, 1H), 8.16 (d, J=8.9 Hz, 1H), 7.89-7.75 (m, 2H), 7.71 (dd, J=9.0, 7.8 Hz, 1H), 7.27 (dd, J=8.0, 1.1 Hz, 1H), 7.12 (dd, J=7.9, 1.1 Hz, 1H), 4.92 (s, 2H). $^{13}$C NMR (101 MHz, DMSO) δ 169.3, 153.1, 151.3, 138.5, 135.5, 132.1, 131.9, 130.0, 125.5, 113.9, 113.3, 111.0, 108.2, 66.9. HRMS (TOF ES$^+$): Exact mass calculated for $C_{14}H_9N_2O_6$[M−H]$^-$: 301.0460, found 301.0465 (1.45 ppm).

Example 8: General Procedure for Synthesis of Phenazine 5,10-dioxide Carbamates

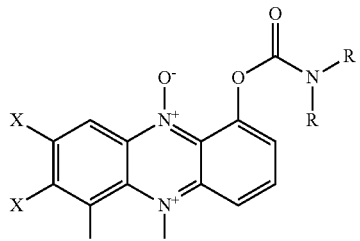

Where: —X = —H, —Cl, —Br, or phenyl —F, —CH$_3$

Or: —R = —H, —OH or —OCH$_3$

A dry round bottomed flask was charged with a hydroxyphenazine 5,10-dioxide of choice (0.5-5 mmol, 1 equiv.), DABCO (3-30 mmol, 6 equiv.) and dissolved/dispersed in anhydrous THV under argon atm at 0° C. To the reaction mixture, a carbamoyl chloride (1.5-15 mmol, 3 eq) was added and the reaction allowed to stir for 30 min before ice bath was removed and the reaction mixture gradually allowed to reach room temperature. The reaction mixture was stirred for 2-3 h. If TLC showed unreacted starting material, carbamoyl chloride (0.5-5 mmol) and DABCO (1.0-10 mmol) are added and the resulting mixture allowed to stir for 1-2 additional hours. The reaction mixture is diluted with NaHCO$_3$ (100-500 mL saturated aqueous sol.). The aqueous layer is extracted with dichloromethane (4×30 mL) or until the aqueous phase is rid of all color. Combined organic phases are dried over MgSO$_4$ and filtered before solvents were removed in vacuo. Obtained crude material was further purified by flash column chromatography on silica.

Example 8a: Preparation of 1-hydroxy-6-((4-methylpiperazine-1-carbonyl)oxy)phenazine 5,10-dioxide

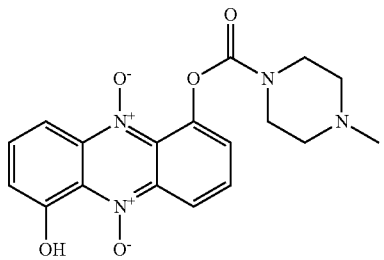 [SMILES: CN1CCN(C(=O)Oc2cccc3c2[n+]([O-])c2cccc(O)c2[n+]3[O-])CC1]

Synthesized in accordance with the general procedure in Example 8. Flash column chromatography on silica afforded 68 mg (33%) of the deep-red solid. $^1$H NMR (400 MHz, Chloroform-d) δ 14.42 (s, 1H), 8.55 (dd, J=9.2, 1.3 Hz, 1H), 7.96 (dd, J=9.0, 1.1 Hz, 1H), 7.72 (dd, J=9.1, 7.6 Hz, 1H), 7.63 (dd, J=9.0, 7.9 Hz, 1H), 7.38 (dd, J=7.5, 1.3 Hz, 1H), 7.12 (dd, J=7.9, 1.1 Hz, 1H), 3.87 (m, 2H), 3.67 (m, 2H), 2.67 (m, 2), 2.58 (m, 2H), 2.43 (s, 3H). $^{13}$C NMR (101 MHz, CDCl$_3$) δ 153.9, 153.3, 143.8, 138.6, 135.5, 132.8, 131.5, 131.0, 126.1, 124.7, 117.1, 115.1, 108.9, 54.8, 54.7, 46.4, 45.1, 44.4. HRMS (ESI+): Exact mass calculated for C$_{18}$H$_{19}$N$_4$O$_5$ [M+H]$^+$: 371.1350, found 371.1348 (0.5 ppm).

Example 8b: Preparation of 1-methoxy-6-((4-methylpiperazine-1-carbonyl)oxy)phenazine 5,10-dioxide

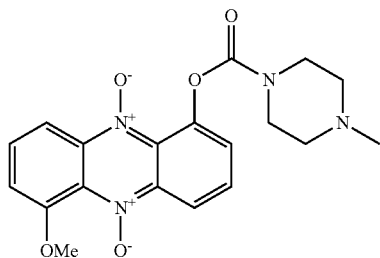 [SMILES: COc1cccc2c1[n+]([O-])c1cccc(OC(=O)N3CCN(C)CC3)c1[n+]2[O-]]

Synthesized in accordance with the general procedure in Example 8. Flash column chromatography on silica (2-5% MeOH/DCM) afforded 92 mg (86%). R$_f$: 0.19 (5% MeOH/DCM). $^1$H NMR (400 MHz, Chloroform-d) δ 8.59 (dd, J=9.2, 1.3 Hz, 1H), 8.22 (dd, J=9.1, 1.1 Hz, 1H), 7.65 (dd, J=9.1, 7.6 Hz, 1H), 7.59 (dd, J=9.1, 8.0 Hz, 1H), 7.06 (dd, J=8.1, 1.1 Hz, 1H), 4.06 (s, 3H), 3.93-3.76 (m, 2H), 3.73-3.53 (m, 2H), 2.79-2.47 (m, 4H), 2.40 (s, 3H). $^{13}$C NMR (101 MHz, CDCl$_3$) δ 153.9, 153.5, 143.8, 139.6, 139.2, 131.0, 131.0, 130.0, 129.6, 124.9, 118.5, 112.1, 110.4, 57.4, 54.8, 54.7, 46.3, 45.1, 44.3.

Example 8c: Preparation of 1-((4-methylpiperazine-1-carbonyl)oxy)phenazine 5,10-dioxide

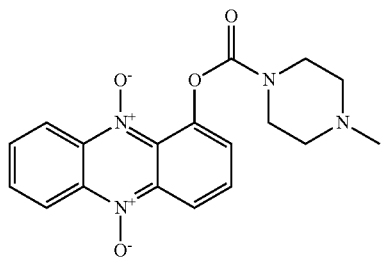 [SMILES: CN1CCN(C(=O)Oc2cccc3c2[n+]([O-])c2ccccc2[n+]3[O-])CC1]

This compound was synthesized according to the general procedure described in Example 8. Flash column chromatography on silica (2-5% MeOH/DCM) afforded 83 mg (73%) of the yellow solid. R$_f$: 0.13 (5% MeOH/DCM). $^1$H NMR (400 MHz, Chloroform-d) δ 8.69-8.59 (m, 3H), 7.84-7.74 (m, 2H), 7.71 (dd, J=9.1, 7.6 Hz, 1H), 7.38 (dd, J=7.6, 1.3 Hz, 1H), 3.88 (s, 2H), 3.68 (s, 2H), 2.75-2.53 (m, 4H), 2.43 (s, 3H). $^{13}$C NMR (101 MHz, CDCl$_3$) δ 153.5, 144.1, 138.0, 137.3, 135.8, 131.7, 131.5, 131.2, 130.5, 124.6, 120.5, 120.2, 118.3, 54.8, 54.7, 46.4, 45.1, 44.3. HRMS (ESI+): Exact mass calculated for C$_{18}$H$_{19}$N$_4$O$_4$ [M+H]$^+$: 355.1401, found 355.1401 (0.0 ppm).

Example 8d: Preparation of 7,8-dimethyl-1-((4-methylpiperazine-1-carbonyl)oxy)phenazine 5,10-dioxide

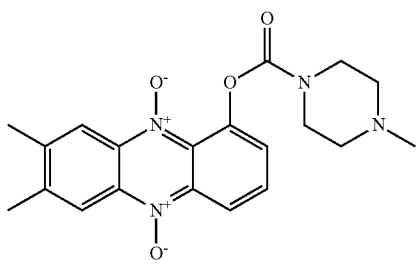

This compound was synthesized according to the general procedure described in Example 8. Flash column chromatography on silica (0-5% MeOH/DCM) afforded 34 mg (99%) of an orange solid. R$_f$: 0.12 (5% MeOH/DCM). $^1$H NMR (400 MHz, Chloroform-d) δ 8.62 (dd, J=9.1, 1.3 Hz, 1H), 8.41 (s, 1H), 8.37 (s, 1H), 7.67 (dd, J=9.1, 7.5 Hz, 1H), 7.35 (dd, J=7.5, 1.3 Hz, 1H), 3.88 (s, 2H), 3.68 (s, 2H), 2.72-2.54 (m, 4H), 2.54-2.47 (m, 6H), 2.42 (s, 3H). 13C NMR (101 MHz, CDCl$_3$) δ 153.6, 144.0, 143.5, 143.0, 137.5, 136.0, 134.5, 131.0, 130.0, 124.2, 119.3, 119.0, 118.2, 54.8, 54.7, 46.4, 45.0, 44.3, 20.6.

Example 8e: Preparation of 1-((4-methylpiperazine-1-carbonyl)oxy)benzo[b]phenazine 5,12-dioxide

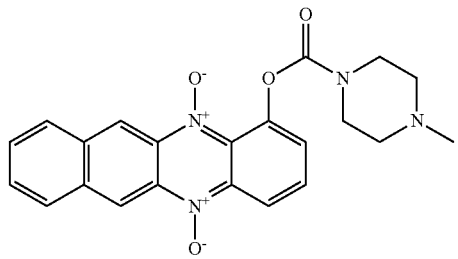 [SMILES: CN1CCN(C(=O)Oc2cccc3c2[n+]([O-])c2cc4ccccc4cc2[n+]3[O-])CC1]

This compound was synthesized according to the general procedure described in Example 8. Flash column chromatography on silica (2-5% MeOH/DCM) afforded 28 mg (97%) of the dark purple solid. R$_f$: 0.23 (5% MeOH/DCM). $^1$H NMR (400 MHz, Chloroform-d) δ 9.25 (s, 1H), 9.19 (s, 1H), 8.63 (dd, J=9.2, 1.3 Hz, 1H), 8.18-8.06 (m, 2H), 7.71-7.60 (m, 3H), 7.34 (dd, J=7.5, 1.3 Hz, 1H), 3.97 (s, 2H), 3.76 (s, 2H), 2.99-2.59 (m, 5H), 2.51 (s, 3H). $^{13}$C NMR (101 MHz, CDCl$_3$) δ 153.6, 143.9, 137.4, 134.7, 134.5, 134.3, 133.3, 131.2, 130.0, 129.1, 129.0, 128.9, 124.0, 119.9, 119.5, 118.3, 54.8, 54.7, 46.3, 45.0, 44.3.

Example 8f: Preparation of 7,8-dichloro-1-((4-methylpiperazine-1-carbonyl)oxy)phenazine 5,10-dioxide

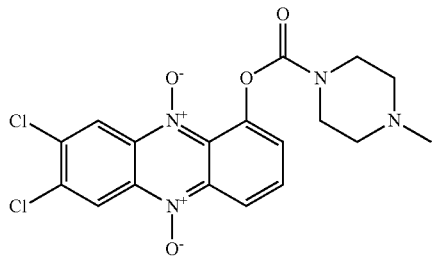

This compound was synthesized according to the general procedure described in Example 8. The obtained crude material was further purified by flash column chromatography on silica (0-5% MeOH/DCM) affording 23 mg (65%) of an orange solid. $R_f$: 0.13 (5% MeOH/DCM). $^1$H NMR (400 MHz, Chloroform-d) δ 8.79 (s, 1H), 8.73 (s, 1H), 8.58 (dd, J=9.2, 1.3 Hz, 1H), 7.74 (dd, J=9.1, 7.6 Hz, 1H), 7.41 (dd, J=7.6, 1.3 Hz, 1H), 3.88 (s, 2H), 3.70 (s, 2H), 2.85-2.53 (m, 4H), 2.46 (s, 3H). $^{13}$C NMR (101 MHz, CDCl$_3$) δ 153.3, 144.2, 138.4, 137.7, 137.3, 135.6, 134.2, 131.9, 131.2, 125.3, 121.7, 121.4, 118.3, 54.7, 53.6, 46.3, 44.9, 44.2. HRMS (ESI+): Exact mass calculated for $C_{18}H_{17}Cl_2N_4O_4$ [M+H]$^+$: 423.0621, found 423.0621 (0.1 ppm).

Example 8g: Preparation of 7,8-dibromo-1-((4-methylpiperazine-1-carbonyl)oxy)phenazine 5,10-dioxide

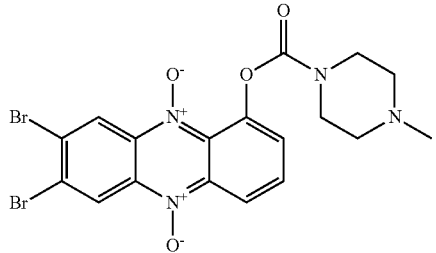 [SMILES: CN1CCN(C(=O)Oc2cccc3c2[n+]([O-])c2cc(Cl)c(Cl)cc2[n+]3[O-])CC1]

This compound was synthesized according to the general procedure described in Example 7. Flash column chromatography on silica (1-5% MeOH/DcM) afforded 63 mg (77%) of a red solid. $R_f$: 0.08 (3% MeOH/DCM). $^1$H NMR (400 MHz, Chloroform-d) δ 8.92 (s, 1H), 8.87 (s, 1H), 8.54 (dd, J=9.2, 1.3 Hz, 1H), 7.72 (dd, J=9.1, 7.6 Hz, 1H), 7.39 (dd, J=7.6, 1.3 Hz, 1H), 3.90-3.75 (m, 2H), 3.70-3.56 (m, 2H), 2.73-2.59 (m, 2H), 2.55 (t, J=5.0 Hz, 2H), 2.41 (s, 3H). $^{13}$C NMR (101 MHz, CDCl$_3$) δ 153.26, 144.20, 138.29, 135.96, 134.51, 131.86, 131.13, 129.77, 129.29, 125.21, 124.90, 124.53, 118.20, 77.16, 54.79, 54.69, 46.37, 45.06, 44.38.

Example 8h: Preparation of 1-((dimethylcarbamoyl)oxy)-6-hydroxyphenazine 5,10-dioxide

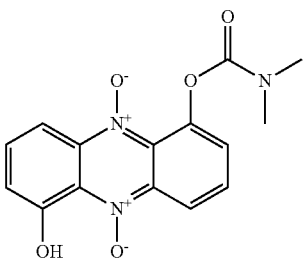 [SMILES: CN(C)C(=O)Oc1cccc2c1[n+]([O-])c1cccc(O)c1[n+]2[O-]]

This compound was synthesized according to the general procedure described in Example 8. Flash column chromatography on silica (1-5% MeOH/DCM) affording 19 mg (8%) of the deep red solid. $R_f$: 0.45 (5% MeOH/DCM). $^1$H NMR (400 MHz, Chloroform-d) δ 14.46 (s, 1H), 8.56 (dd, J=9.1, 1.3 Hz, 1H), 7.97 (dd, J=9.0, 1.1 Hz, 1H), 7.73 (dd, J=9.2, 7.6 Hz, 1H), 7.63 (dd, J=9.0, 7.9 Hz, 1H), 7.38 (dd, J=7.5, 1.3 Hz, 1H), 7.12 (dd, J=7.9, 1.1 Hz, 1H), 3.27 (s, 3H), 3.10 (s, 3H). $^{13}$C NMR (101 MHz, CDCl$_3$) δ 154.5, 153.8, 143.9, 138.6, 135.4, 132.7, 131.5, 130.9, 123.0, 124.6, 116.9, 114.9, 108.7, 37.0, 36.9. HRMS (ESI+): Exact mass calculated for $C_{15}H_{13}N_3O_5$ [M+K]$^+$: 354.0487, found 354.0487 (−0.1 ppm).

Example 8i: Preparation of 1-((diethylcarbamoyl)oxy)-6-hydroxyphenazine 5,10-dioxide

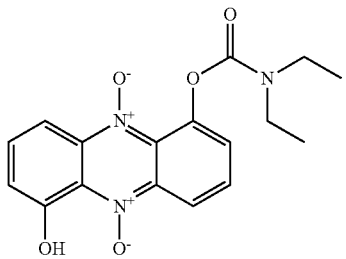 [SMILES: CCN(CC)C(=O)Oc1cccc2c1[n+]([O-])c1cccc(O)c1[n+]2[O-]]

This compound was synthesized according to the general procedure described in Example 8. Flash column chromatography on silica (0-50% EtOAc/Heptan) afforded the deep-red solid. $R_f$: 0.45 (1:1 EtOAc/Hep). $^1$H NMR (600 MHz, Chloroform-d) δ 14.49 (s, 1H), 8.55 (dd, J=9.1, 1.3 Hz, 1H), 7.96 (dd, J=9.0, 1.1 Hz, 1H), 7.72 (dd, J=9.1, 7.5 Hz, 1H), 7.61 (dd, J=9.0, 7.9 Hz, 1H), 7.38 (dd, J=7.5, 1.3 Hz, 1H), 7.11 (dd, J=8.0, 1.1 Hz, 1H), 3.63 (q, J=7.2 Hz, 2H), 3.45 (q, J=7.1 Hz, 2H), 1.40 (t, J=7.1 Hz, 3H), 1.28 (t, J=7.1 Hz, 4H). $^{13}$C NMR (151 MHz, CDCl$_3$) δ 154.0, 153.9, 144.1, 138.7, 135.5, 132.7, 131.8, 131.0, 126.1, 124.7, 116.9, 115.0, 108.9, 42.6, 42.4, 14.2, 13.4. HRMS (TOF ES+): Exact mass calculated for $C_{17}H_{17}N_3O_5$ Na [M+Na]$^+$: 366.1065, found 366.1060 (−1.61 ppm).

Example 8i: Synthesis of 1-hydroxy-6-((pyrrolidine-1-carbonyl)oxy)phenazine 5,10-dioxide

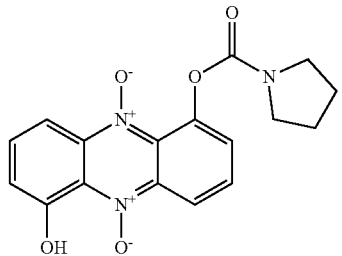 [SMILES: O=C(Oc1cccc2c1[n+]([O-])c1cccc(O)c1[n+]2[O-])N1CCCC1]

This compound was synthesized according to the general procedure described in Example 8. Flash column chromatography on silica (0-5% MeOH/DCM) afforded 24 mg (11%) of the red solid. $R_f$: 0.63 (3% MeOH/DCM). $^1$H-NMR (400 MHz, Chloroform-d) δ 14.49 (s, 1H), 8.55 (dd, J=9.2, 1.2 Hz, 1H), 7.97 (dd, J=9.0, 1.0 Hz, 1H), 7.72 (d, J=7.6 Hz, 1H), 7.61 (d, J=8.0 Hz, 1H), 7.40 (dd, J=7.6, 1.2 Hz, 1H), 7.12 (dd, J=7.9, 1.0 Hz, 1), 3.77 (t, J=6.7 Hz, 2H), 3.56 (t, J=6.7 Hz, 2H), 2.04 (dp, J=19.7, 6.6 Hz, 4H). $^{13}$C-NMR (101 MHz, CDCl$_3$) δ 153.92, 152.83, 143.89, 138.75, 135.56, 132.75, 131.75, 131.08, 126.08, 124.83, 116.98, 115.01, 108.90, 46.89, 46.87, 26.05, 25.29. HRMS (TOF ES+): Exact mass calculated for C$_{17}$H$_{15}$N$_3$O$_5$ Na [M+Na]$^+$: 364.364.0904, found 364.0896 (2.1 ppm).

Example 8k: Preparation of 1-((dimethylcarbamoyl)oxy)phenazine 5,10-dioxide

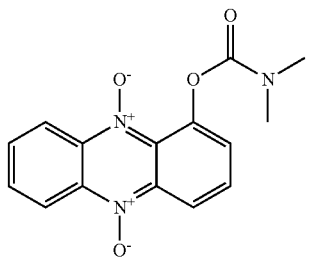 [SMILES: CN(C)C(=O)Oc1cccc2c1[n+]([O-])c1ccccc1[n+]2[O-]]

This compound was synthesized according to the general procedure described in Example 8. Flash column chromatography on silica (0-2% MeOH/DCM) afforded 79 mg (77%) of the orange/yellow solid. $R_f$: 0.39 (5% MeOH/DCM). $^1$H NMR (400 MHz, Chloroform-d) δ 8.72-8.60 (m, 3H), 7.83-7.74 (m, 2H), 7.71 (dd, J=9.1, 7.5 Hz, 1H), 7.39 (dd, J=7.5, 1.3 Hz, 1H), 3.28 (s, 3H), 3.11 (s, 3H). $^{13}$C NMR (101 MHz, CDCl$_3$) δ 154.8, 144.3, 138.0, 137.5, 135.9, 131.7, 131.7, 131.2, 130.5, 124.7, 120.6, 120.3, 118.2, 37.2, 37.1. HRMS (ESI+): Exact mass calculated for C$_{15}$H$_{13}$N$_3$O$_4$Na [M+Na]$^+$: 322.0798, found 322.0798 (−0.1 ppm).

Example 8l: Preparation of 1-methoxy-6-((pyrrolidine-1-carbonyl)oxy)phenazine 5,10-dioxide

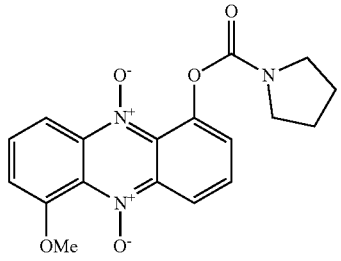 [SMILES: COc1cccc2c1[n+]([O-])c1cccc(OC(=O)N3CCCC3)c1[n+]2[O-]]

This compound was synthesized according to the general procedure described in Example 8. Flash column chromatography on silica (0-2% MeOH/DCM) afforded 44 mg (59%). $R_f$: 0.19 (5% MeOH/DCM). $^1$H NMR (400 MHz, Chloroform-d) δ 8.59 (dd, J=9.2, 1.3 Hz, 1H), 8.22 (dd, J=9.1, 1.1 Hz, 1H), 7.65 (dd, J=9.1, 7.5 Hz, 1H), 7.57 (dd, J=9.1, 8.0 Hz, 1H), 7.37 (dd, J=7.5, 1.3 Hz, 1H), 7.05 (dd, J=8.1, 1.1 Hz, 1H), 4.06 (s, 3H), 3.76 (t, J=6.7 Hz, 2H), 3.54 (t, J=6.6 Hz, 2H), 2.12-1.93 (m, 4H). $^{13}$C NMR (101 MHz, CDCl$_3$) δ 153.95, 153.0, 143.8, 139.7, 139.2, 131.3, 130.9, 130.1, 129.6, 125.0, 118.4, 112.1, 110.4, 57.4, 46.8, 26.0, 25.2.

Example 8m: Preparation of 1-((dimethylcarbamoyl)oxy)-6-methoxyphenazine 5,10-dioxide

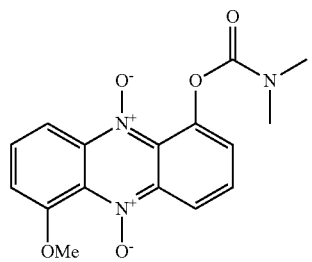 [SMILES: COc1cccc2c1[n+]([O-])c1cccc(OC(=O)N(C)C)c1[n+]2[O-]]

This compound was synthesized according to the general procedure described in Example 8 from myxin and dimethylcarbamoyl chloride. Flash column chromatography (1% MeOH/DCM) afforded 29 mg (46%) of an orange solid. $R_f$: 0.24 (3% MeOH/DCM). $^1$H NMR (400 MHz, Chloroform-d) δ 8.60 (dd, J=9.1, 1.3 Hz, 1H), 8.24 (dd, J=9.1, 1.1 Hz, 1H), 7.65 (dd, J=9.1, 7.5 Hz, 1H), 7.59 (dd, J=9.1, 8.0 Hz, 1H), 7.36 (dd, J=7.5, 1.3 Hz, 1H), 7.06 (dd, J=7.9, 1.1 Hz, 1H), 4.07 (s, 3H), 3.26 (s, 3H), 3.09 (s, 3H). $^{13}$C NMR (101 MHz, CDCl$_3$) δ 154.8, 154.0, 144.0, 139.7, 139.3, 131.2, 131.0, 130.0, 129.7, 125.0, 118.5, 112.2, 110.5, 57.4, 37.1, 37.0.

Examples 9a-f: General Example for Preparation of Hydrochloric Salts of Phenazine 5,10-Dioxides Conjugated to a Carbamate-Piperazine Moiety (Examples 8a-8f)

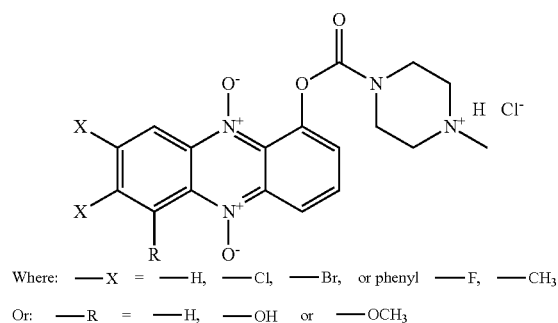

Where: —X = —H, —Cl, —Br, or phenyl —F, —CH₃
Or: —R = —H, —OH or —OCH₃

Piperazine phenzine 5,10 dioxide (0.1-5 mmol derivative from Examples 8a-8f) is placed in a dry round bottom flask at 0° C. Then, HCl, (0.1-50 mmol) using HCl (2.0 M in ether or 4.0 M in Dioxane) is added drop wise. The resulting dispersion is left stirring for 1-24 hours. The crude mixture is then concentrated in vacuo and if necessary, purified by chromatography on silica, C18 gel or recrystallization from appropriate solvent mixture.

Example 10: Preparation of 1-((ethoxycarbonyl)oxy)-6-hydroxyphenazine 5,10-dioxide

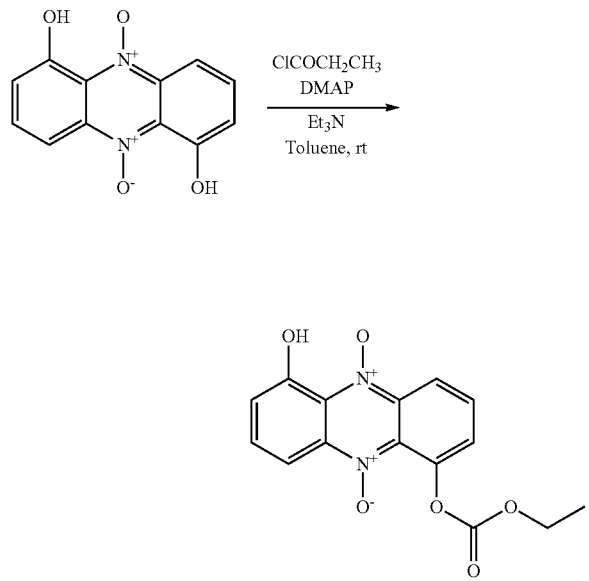

Iodinin (160 mg, 0.66 mmol, 1 eq) was placed in a dry round bottomed flask and dispersed in anhydrous toluene (10 mL) and cooled down to −40° C. under arg atm. Then added ethyl chloroformate (88 μL, 0.92 mmol, 1.4 eq) and DMAP (16 mg, 0.13 mmol, 0.2 eq). The resulting mixture was left for 10 min rotating before Et₃N (128 μL, 0.92 mmol, 1.4 eq) was added. The mixture was then allowed to stir for 1 hour before another portion of ethyl chloroformate (38 μL, 0.39 mmol, 0.6 eq) was added. At this point in time, dry ice-acetone bath was removed and the mixture gradually allowed warming towards rt over a period of 30 min. The resulting mixture was diluted by 30 mL of diethyl ether and re-cooled to −40° C. (to lower to solubility of unreacted iodinin). The reaction mixture was filtered through a sintered funnel and the remaining sediment on top washed with diethyl ether (20 mL) and MeOH (20 mL). The obtained solution was concentrated in vacuo and re-dissolved in EtOAc (50 mL). Combined organic phase was washed with 1M HCl (2×30 mL in order to remove DMAP). The organic phase was dried over MgSO₄, filtered and dry-loaded on silica. Flash column chromatography (20-50% EtOAc/Heptane) afforded 51 mg (25%) of the deep-red solid. R_f: 0.39 (1:1 EtOAc/Heptane). ¹H NMR (600 MHz, Chloroform-d) δ 14.32 (s, 1H), 8.59 (dd, J=9.1, 1.3 Hz, 1H), 7.98 (dd, J=9.0, 1.1 Hz, 1H), 7.74 (dd, J=9.1, 7.6 Hz, 1H), 7.65 (dd, J=9.0, 7.9 Hz, 1H), 7.44 (dd, J=7.6, 1.3 Hz, 1H), 7.13 (dd, J=7.9, 1.1 Hz, 1H), 4.44 (q, J=7.1 Hz, 2H), 1.47 (t, J=7.1 Hz, 3H). ¹³C NMR (151 MHz, CDCl₃) δ 153.9, 153.0, 143.1, 138.6, 135.5, 133.2, 130.9, 130.9, 126.2, 124.0, 117.9, 115.3, 108.8, 65.9, 14.4. HRMS (EI⁺): Exact mass calculated for C₁₅H₁₂N₂O₆: 316.0695, found 316.0686 (2.9 ppm).

Example 11: Preparation of 2,3-dimethylquinoxalin-5-ol

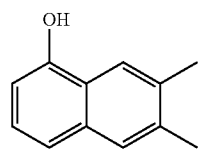

A round bottom flask with a reflux condenser was charged with 3-amino-2-nitrophenol (1.5 g, 9.7 mmol), Na₂S₂O₄ (25 mL, saturated aqueous solution), MeOH (20 mL) and Na₂CO₃ (5 g dissolved in 15 mL of H₂O). The resulting dispersion was warmed gradually to 100° C. and maintained stirring for 2 h. Upon cooldown, the mixture was concentrated in vacuo to a slurry paste crude material which was dispersed in PhMe/AcOH (90 mL, 1:1) in addition to glacial AcOH (10 mL). Diacetyl (1.16 mL, 12.17 mmol) was added to the dispersion and the mixture allowed to rotate at room temperature overnight. The reaction mixture was concentrated to a paste in vacuo before it was dispersed in NaHCO₃ (350 mL saturated aqueous solution). The aqueous phase was extracted using DCM (4×50 mL) and the combined organic phases were washed with (200 mL saturated aqueous solution), dried over MgSO₄ and filtered. Recrystallization of the crude material from hot ethanol afforded 693 mg of the purified product. The remaining material after recrystallization was concentrated and filtered through a plug of silica under vacuum. This purification step gave 641 mg of the purified product as well. Yield: 1334 mg (79%) after 2 steps. R_f: 0.63 (DCM). ¹H NMR (600 MHz, Chloroform-d) δ 7.92-7.80 (m, 1H), 7.57-7.51 (m, 1H), 7.51-7.46 (m, 1H), 7.10 (dd, J=7.4, 1.4 Hz, 1H), 2.71 (d, J=2.4 Hz, 3H), 2.67 (d, J=3.6 Hz, 3H). ¹³C NMR (151 MHz, CDCl₃) δ 154.4, 151.6, 151.3, 141.4, 131.0, 129.9, 118.8, 110.1, 23.2, 22.9.

Example 12: Preparation of 5-hydroxy-2,3-dimethylquinoxaline 1,4-dioxide

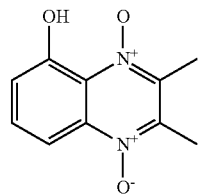

Upon cooldown of the reaction mixture described in general procedure 4, the mixture was diluted by NaHCO₃ (200 mL aqueous solution) and the aqueous phase extracted (4×50 mL toluene). The organic phase was dried over MgSO4, filtered and absorbed onto silica gel. Flash column chromatography on silica (100% DCM) affords the purified product.

Example 13: Preparation of 2,3-dimethyl-5-((4-methylpiperazine-1-carbonyl)oxy)quinoxaline 1,4-dioxide

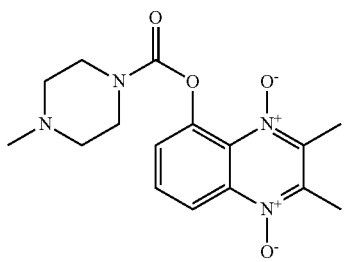

Synthesized according to the general procedure in Example 8 from 5-hydroxy-2,3-dimethylquinoxaline 1,4-dioxide (Example 12). The product is purified by flash column chromatography on silica using appropriate mixture of solvents as eluent or is recrystallized from appropriate solvent or mixture of solvents.

Example 14: Preparation of 5-(2-ethoxy-2-oxoethoxy)-2,3-dimethylquinoxaline 1,4-dioxide

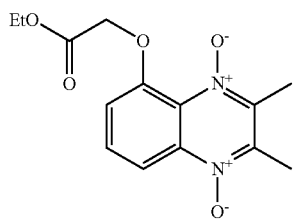 [SMILES: CCOC(=O)COc1cccc2c1[n+]([O-])c(C)c(C)[n+]2[O-]]

Synthesized according to the general procedure in Example 5 from 5-hydroxy-2,3-dimethylquinoxaline 1,4-dioxide using ethyl bromoacetate as the alkylating agent. The product is purified by flash column chromatography on silica using appropriate mixture of solvents as eluent or is recrystallized from appropriate solvent or mixture of solvents.

Example 15: Preparation of 5-methoxy-2,3-dimethylquinoxaline 1,4-dioxide

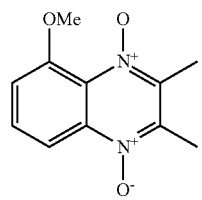 [SMILES: COc1cccc2c1[n+](O)c(C)c(C)[n+]2[O-]]

The compound was synthesized according to the general procedure in Example 5 from 5-hydroxy-2,3-dimethylquinoxaline 1,4-dioxide using methyl iodide as the alkylating agent. The product is purified by flash column chromatography on silica using appropriate mixture of solvents as eluent or is recrystallized from appropriate solvent or mixture of solvents.

Example 16: Preparation of Diverse Disubstituted Compounds

Example 16a: 1,6-bis((pyrrolidine-1-carbonyl)oxy)phenazine 5,10-dioxide

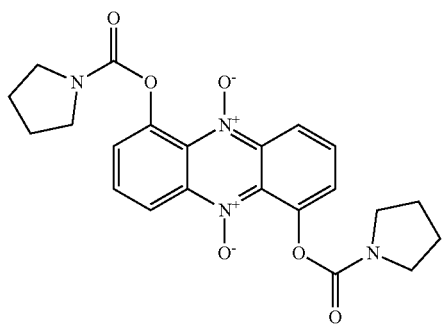

Molecular Weight: 438.44

The compound was isolated from the crude mixture described in Example 8j. After flash column chromatography on silica (0-5% MeOH/DCM) and evaporation of solvents in vacuo, the crude compound was dispersed in boiling EtOH. Then, CHCl₃ was added drop wise until a clear solution was obtained. The resulting solution was allowed to cool down slowly to rt where orange chrystals precipitated. Filtration and drying in vacuo afforded 74 mg (22%) of the orange crystalline solid. $R_f$: 0.23 (3% MeOH/DCM). $^1$H NMR (400 MHz, CDCl₃) δ 8.53 (dd, J=9.1, 1.3 Hz, 2H), 7.65 (dd, J=9.2, 7.6 Hz, 2H), 7.38 (dd, J=7.6, 1.3 Hz, 2H), 3.77 (t, J=6.7 Hz, 4H), 3.56 (t, J=6.7 Hz, 4H), 2.18-1.88 (m, 8H). $^{13}$C NMR (101 MHz, CDCl₃) δ 153.0, 144.0, 139.3, 131.5, 130.3, 125.1, 118.3, 46.8, 26.1, 25.3.

Example 16b: 1,6-bis(pentanoyloxy)phenazine 5,10-dioxide

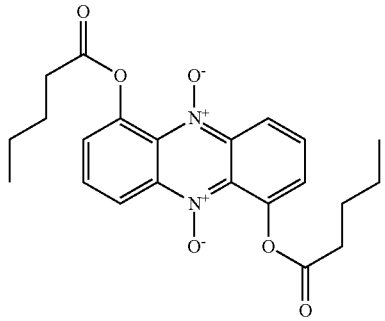

Molecular Weight: 412.44

A dry round bottomed flask was charged with iodinin (45 mg, 0.18 mmol) under argon atm and dispersed in anhydrous toluene (5 mL). The deep-purple dispersion was cooled down to 0° C. before valeric anhydride (218 µL, 1.11 mmol) was added dropwise. The mixture was stirred for 10 minutes before DMAP (4.5 mg, 0.04 mmol) was added, followed by Et$_3$N (102 µL, 0.74 mmol) upon which the mixture started to turn color rapidly from purple towards more yellow/orange. The mixture left stirring for a period of 16 hours gradually reaching room temperature before quenched with NH$_4$Cl (50 mL 10% aqueous sol.) The aqueous layer was extracted by DCM (2×30 mL) and pooled organic phases washed with HCl (50 mL 0.1M aqueous sol.), brine (50 mL), dried over MgSO$_4$ and filtered. Flash column chromatography on silica (10-50% EtOAc/heptane) afforded 30 mg (39%) of the orange solid. R$_f$: 0.33 (30% EtOAc/Heptane). $^1$H NMR (400 MHz, CDCl$_3$) δ 8.54 (dd, J=9.2, 1.3 Hz, 2H), 7.69 (dd, J=9.1, 7.6 Hz, 2H), 7.34 (dd, J=7.5, 1.3 Hz, 2H), 2.81 (t, J=7.6 Hz, 4H), 1.84 (p, J=7.6 Hz, 4H), 1.57-1.47 (m, 4H), 1.01 (t, J=7.4 Hz, 6H). $^{13}$C NMR (101 MHz, CDCl$_3$) δ 172.4, 143.3, 139.2, 130.9, 130.6, 124.7, 118.6, 34.1, 26.7, 22.5, 14.0. HRMS (TOF ES+): Exact mass calculated for C$_{22}$H$_{24}$N$_2$O$_6$ Na [M+Na]+: 435.1532, found 435.1530 (−0.47 ppm).

Example 16c: 1,6-bis(2-ethoxy-2-oxoethoxy)phenazine 5,10-dioxide

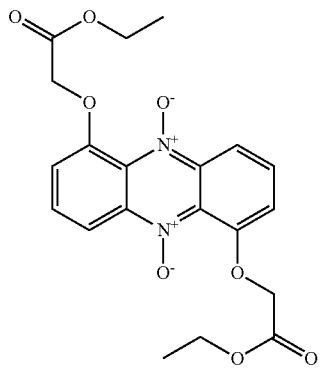 [SMILES: CCOC(=O)COc1cccc2c1[n+]([O-])c1cccc(OCC(=O)OCC)c1[n+]2[O-]]

This product was isolated as a by-product from the same crude material afforded after the work-up described for Example 5c. Flash column chromatography, first 30-100% EtOAc/heptane to remove the monoalkylated product, then switching to 1:7 EtOAc/DCM) afforded 43 mg (14%) of an orange solid. R$_f$: 0.23 (3% MeOH/DCM). $^1$H-NMR (600 MHz, CDCl$_3$) δ 8.41 (dd, J=9.0, 1.2 Hz, 2H), 7.60 (dd, J=9.1, 7.8 Hz, 2H), 7.16 (dd, J=7.9, 1.2 Hz, 2H), 4.88 (s, 4H), 4.30 (q, J=7.1 Hz, 4H), 1.30 (t, J=7.2 Hz, 6H). $^{13}$C-NMR (151 MHz, CDCl$_3$) δ 168.19, 151.66, 139.86, 130.57, 115.66, 114.69, 77.16, 68.68, 61.75, 14.32. HRMS (TOF ES+): Exact mass calculated for C$_{20}$H$_{20}$N$_2$O$_8$Na [M+Na]+: 439.1117, found 439.1121 (0.82 ppm).

Example 16d: 1,6-bis(pivaloyloxy)phenazine 5,10-dioxide

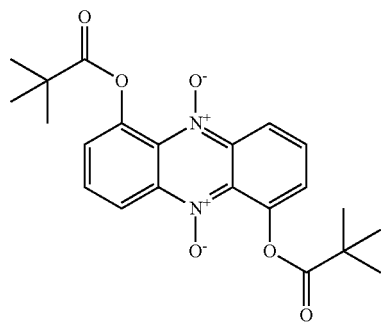 [SMILES: CC(C)(C)C(=O)Oc1cccc2c1[n+]([O-])c1cccc(OC(=O)C(C)(C)C)c1[n+]2[O-]]

Iodinin (50 mg, 0.20 mmol) was weighed in a dry round bottom flask under an argon atmosphere. Toluene (4 mL) was added and the dispersion cooled down to −40° C. Pivalyl chloride was added drop wise (0.15 mL, 1.23 mmol) followed by Et$_3$N (0.17 mL, 1.23 mmol) and the resulting mixture stirred for 1 hour. DMAP (10 mg, 0.08 mmol) was added upon which the color of the mixture started immediately to turn from from dark purple towards brown/yellow. The mixture was stirred for 30 min or until no starting material observed by TLC and then quenched with H$_2$O (50 mL). The aqueous phase was extracted by EtOAc (3×25 mL). Pooled organic phases were washed with HCl (1M aqueous sol.), dried over MgSO$_4$ and filtered before solvents were removed in vacuo. Flash column chromatography on silica (20% EtOAc/heptane) afforded 33 mg (39%) of an orange solid. R$_f$: 0.28 (20% EtOAc/Heptane)$^1$H NMR (600 MHz, CDCl$_3$) δ 8.55 (dd, J=9.1, 1.3 Hz, 2H), 7.65 (dd, J=9.1, 7.5 Hz, 2H), 7.28 (dd, J=7.5, 1.3 Hz, 2H), 1.50 (s, 18H). $^{13}$C NMR (151 MHz, CDCl$_3$) δ 176.86, 143.73, 139.21, 131.10, 130.23, 124.46, 118.71, 39.21, 27.41. HRMS (TOF ES$^-$): Exact mass calculated for C$_{22}$H$_{24}$N$_2$O$_6$Na [M+Na]$^+$: 435.1532, found 435.1540 (1.82 ppm).

Example 16e:
1,6-bis((ethoxycarbonyl)oxy)phenazine 5,10-dioxide

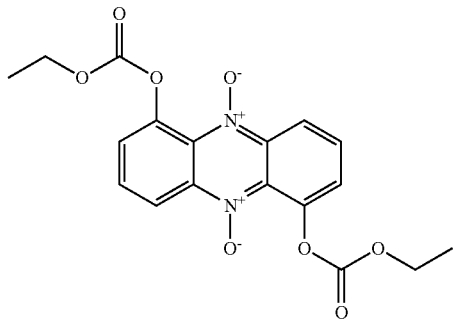 [SMILES: CCOC(=O)Oc1cccc2c1[n+]([O-])c1cccc(OC(=O)OCC)c1[n+]2[O-]]

A dry round bottomed flask was charged with iodinin (60 mg, 0.25 mmol, 1 eq) and dispersed in anhydrous toluene (4 mL). The purple dispersion was cooled down to 0° C. before ethyl chloroformate (105 μL. 1.10 mmol) was added. The mixture was stirred for 10 minutes before DMAP (15 mg, 0.12 mmol, 0.5 eq) was added followed by Et$_3$N (30 μL, 0.20 mmol, 0.8 eq) which upon the mixture starting to shift color. The resulting mixture was left stirring for 30 min before another addition of ethyl chloroformate (50 μL, 0.52 mmol, 2.1 eq) and Et$_3$N (30 μL, 0.20 mmol, 0.8 eq) was added. The mixture was stirred at 0° C. for 90 minutes before filtered and the retained material on top (mostly unreacted iodinin (3)) washed with ice-cold Et$_2$O and MeOH (30 mL each). The filtered mixture was concentrated in vacuo, dispersed in H$_2$O (50 mL) and the aqueous layer extracted with EtOAc (4×30 mL). Combined organic phases were washed with HCl (1M aqueous sol., 150 mL), brine (150 mL), dried over MgSO$_4$, filtered and concentrated in vacuo. Flash column chromatography on silica (20-50% EtOAc/Heptane) afforded 64 mg (67%), orange solid. R$_f$: 0.39 (1:1 EtOAc/Heptane). $^1$H NMR (600 MHz, CDCl$_3$) δ 8.59 (dd, J=9.1, 1.3 Hz, 2H), 7.70 (dd, J=9.1, 7.5 Hz, 2H), 7.46 (dd, J=7.6, 1.3 Hz, 2H), 4.44 (q, J=7.1 Hz, 4H), 1.47 (t, J=7.1 Hz, 6H). $^{13}$C NMR (151 MHz, CDCl$_3$) δ 153.1, 143.4, 139.1, 130.8, 130.6, 124.4, 119.0, 65.9, 14.4. HRMS (EI): Exact mass calculated for C$_{18}$H$_{16}$N$_2$O$_8$: 388.0907, found 388.0900 (1.8 ppm).

Example 17: Preparation of the Building Block 1-hydroxyphenazine 5,10-dioxide by Beirut Diketone Application

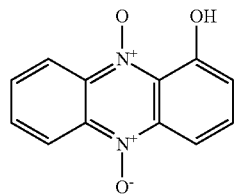 [SMILES: [O-][n+]1c2ccccc2[n+](O)c2c(O)cccc21]

Synthesized according to a published procedure by Haddadin et al. with small modifications. Benzofuroxan (6.0 g, 44 mmol, 2 eq) dissolved in diethylamine (60 mL) was added drop wise via a dropping funnel to a stirring solution of 1.2-cyclohexanedione (2.47 g, 22.0 mmol, 1 eq) diethylamine (25 mL) at 0° C. Upon complete addition, the mixture was stirred for 30 min before the ice bath was removed, then stirred for 60 min gradually reaching room temperature. The resulting reaction mixture was pored over ice followed and neutralized with AcOH (drop-wise, ~60 mL). The precipitated red crude compound was filtered and the retained filter cake washed with cold H$_2$O and dried. The red crude material was placed in a 250 mL round bottomed flask and dispersed in toluene (150 mL). mCPBA (2.5 g, Sigma Aldrich, ≤77%) was added and the mixture gradually warmed up to 80° C. mCPBA (1.5 g, Sigma Aldrich, ≤77%) was added again 1 h from start, 2 h from start and 3 h from start. The resulting mixture was left stirring for 60 min after addition of the last portion before cooled down on ice bath. After cooldown, the mixture was transferred to a 1 L round bottomed flask and carefully concentrated to a dark slurr in vacuo. The crude afforded was re-dissolved in minimum amount of DCM and the crude mixture absorbed onto silica gel. The silica-absorbed crude material was placed on top of a silica plug (8 cm high, 5 cm in diameter) and eluted trough silica using 0-50% EtOAc/DCM only collecting solution of intense red brown color. The dark-red solution was concentrated in vacuo and the obtained crude material dispersed in MeOH and filtered (Buchner funnel with filter paper). The retained filter cake on top was washed further in the following order; H$_2$O (100 mL), MeOH (50 mL), NaHCO$_3$ (sat. aqueous sol., 100 mL), H$_2$O (100 mL) and MeOH (50 mL). The brown-red filter cake was now dried before the material on top was collected, dissolved in minimum amount of CHCl$_3$ and concentrated in vacuo affording 2.0 g (40% over 2 steps) of brown-red powder. R$_f$. 0.74 (1% MeOH/DCM). $^1$H-NMR (400 MHz, CDCl$_3$) δ 14.48 (s, 1H), 8.69-8.59 (m, 2H), 8.06 (dd, J=9.0, 1.1 Hz, 1H), 7.89-7.77 (m, 2H), 7.68 (dd, J=9.0, 7.9 Hz, 1H), 7.14 (dd, J=7.9, 1.1 Hz, 1H). $^{13}$C-NMR (101 MHz, CDCl$_3$) δ 154.1, 137.5, 136.1, 133.8, 133.0, 131.8, 131.7, 126.6, 120.1, 119.4, 114.7, 108.7. HRMS (ESI+): Exact mass calculated for C$_{12}$H$_8$N$_2$O$_3$ Na [M+Na]$^+$: 251.0427, found 251.0427 (0.1 ppm).

Example 18: Preparation of the Building Block 1-methoxyphenazine 5,10-dioxide

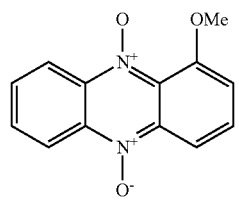 [SMILES: COc1cccc2c1[n+](O)c1ccccc1[n+]2[O-]]

Synthesized in accordance to general procedure 5 starting from 1-hydroxyphenazine 5,10-dioxide (15 mg, 0.07 mmol) using MeI as a methylating reagent. Flash column chromatography on silica (1% MeOH/DCM) afforded 10 mg (63%) of an orange solid. R$_f$. 0.13 (1% MeOH/DCM). $^1$H NMR (400 MHz, CDCl$_3$) δ 8.69 (td, J=8.3, 1.1 Hz, 2H), 8.34 (dd, J=9.0, 1.1 Hz, 1H), 7.86-7.74 (m, 2H), 7.67 (dd, J=9.1, 7.9 Hz, 1H), 7.13-7.05 (m, 1H), 4.10 (s, 3H). $^{13}$C NMR (101 MHz, CDCl$_3$) δ 154.2, 138.5, 137.5, 135.7, 131.8, 131.4, 131.0, 130.1, 120.7, 120.2, 112.0, 110.0, 57.4. HRMS (ESI+): Exact mass calculated for C$_{13}$H$_{10}$N$_2$O$_3$Na [M+Na]$^+$: 265.0584, found 265.0584 (0.1 ppm).

Example 19: Preparation of 1-(2-(tert-butoxy)-2-oxoethoxy)phenazine 5,10-dioxide

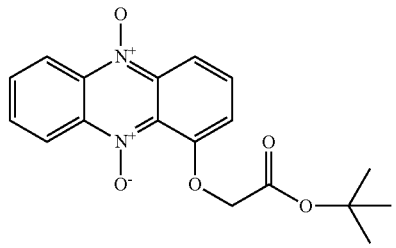 [SMILES: CC(C)(C)OC(=O)COc1cccc2c1[n+]([O-])c1ccccc1[n+]2O]

Prepared in accordance to general procedure 6 from 1-hydroxyphenazine 5,10-dioxide. Flash column chromatography (dry-load) on silica (60-100% EtOAc/heptane) gave 58 mg (82%) of an orange solid. $R_f$: 0.41 (100% EtOAc). $^1$H NMR (400 MHz, CDCl$_3$) δ 8.73-8.60 (m, 2H), 8.38 (dd, J=9.1, 1.2 Hz, 1H), 7.86-7.73 (m, 2H), 7.61 (dd, J=9.1, 7.9 Hz, 1H), 7.08 (dd, J=7.9, 1.2 Hz, 1H), 4.77 (s, 2H), 1.48 (s, 9H). $^{13}$C NMR (101 MHz, CDCl$_3$) δ 167.0, 152.2, 138.4, 137.6, 135.7, 131.7, 131.0, 130.8, 130.6, 120.7, 120.1, 113.9, 113.7, 82.9, 68.4, 28.2. HRMS (ESI+): Exact mass calculated for C$_{18}$H$_{18}$N$_2$O$_5$Na [M+Na]$^+$: 365.1108, found 365.1107 (0.4 ppm).

Example 20: Preparation of 1-(carboxymethoxy)phenazine 5,10-dioxide

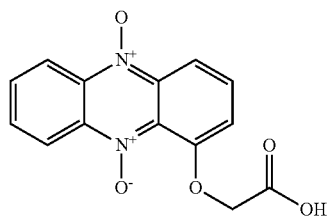 [SMILES: O=C(O)COc1cccc2c1[n+]([O-])c1ccccc1[n+]2O]

A round bottom flask cooled on ice bath is charged with 1-(2-(tert-butoxy)-2-oxoethoxy)phenazine 5,10-dioxide (1 mmol, 1 equiv) from example 19 and dissolved in minimum amount of DCM. To the solution, H$_3$PO$_4$ (85% aqueous sol, 0.5-1 mL) is added drop wise. The reaction mixture is stirred until the starting material is consumed (judged by TLC). The crude mixture is thereafter neutralized and the pH adjusted to ~8 by NaHCO$_3$ (saturated aqueous sol.). The aqueous phase is washed with DCM (3×10 mL, or until no color is observed within the organic phase). The resulting aqueous phase is collected and the pH adjusted to 1 by HCl (1 M aqueous sol.) The resulting precipitate is filtered filtered on a Buchner funnel and washed with H$_2$O (20 mL), MeOH (20 mL) and Et$_2$O (30 mL) and dried. If needed, further purification is undertaken using recrystallization from appropriate solvent, C18 chromatography or flash column chromatography on silica.

Example 21: Preparation of 1-(2-(diethylamino)-2-oxoethoxy)phenazine 5,10-dioxide

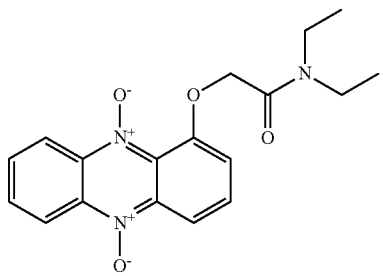 [SMILES: CCN(CC)C(=O)COc1cccc2c1[n+]([O-])c1ccccc1[n+]2[O-]]

Prepared in accordance to general procedure 6 from 1-hydroxyphenazine 5,10-dioxide (200 mg) treated with 2-chloro-N,N-diethylacetamide and potassium iodide cat in the presence of potassium carbonate and 18-Crown-6. Flash column chromatography on silica (2-5% MeOH/DCM) and subsequent recrystallization from hot EtOH afforded 75 mg (25%) of the orange solid. $R_f$: 0.22 (5% MeOH/DCM) $^1$H NMR (400 MHz, CDCl$_3$) δ 8.73-8.61 (m, 2H), 8.39 (dd, J=9.1, 1.2 Hz, 1H), 7.85-7.73 (m, 2H), 7.64 (dd, J=9.0, 7.9 Hz, 1H), 7.33 (dd, J=7.9, 1.2 Hz, 1H), 4.98 (s, 2H), 3.55 (q, J=7.1 Hz, 2H), 3.42 (q, J=7.1 Hz, 2H), 1.22 (t, J=7.1 Hz, 3H), 1.13 (t, J=7.1 Hz, 3H). $^{13}$C NMR (101 MHz, CDCl$_3$) δ 166.3, 152.4, 138.5, 137.6, 135.8, 131.7, 131.2, 131.0, 130.6, 120.7, 120.3, 114.7, 113.6, 70.6, 41.7, 40.5, 14.5, 13.0.

Example 22: Preparation of 1-(2-(4-(ethoxycarbonyl)piperazin-1-yl)-2-oxoethoxy)phenazine 5,10-dioxide

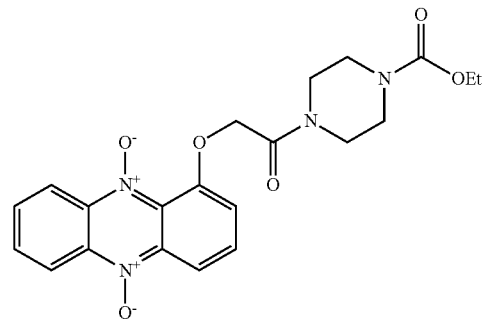 [SMILES: CCOC(=O)N1CCN(C(=O)COc2cccc3c2[n+]([O-])c2ccccc2[n+]3[O-])CC1]

In a round bottom flask, ethyl piperazine-1-carboxylate 2.9 mL (20 mmol) was dissolved in DCM (30 mL) under argon atm and the resulting solution cooled to 0° C. To this solution, chloroacetyl chloride (1.4 mL, 18 mmol), dissolved in DCM (40 mL) was added drop-wise via dropping funnel. The resulting mixture was stirred overnight before transferred to a separatory funnel and diluted by 250 mL HCl (0.1 M aqueous sol). The organic phase was collected followed by extraction of the aqueous phase using DCM (3×30 mL). The pooled organic phases were washed with brine (200 mL), dried over MgSO$_4$ and filtered before solvent were removed in vacuo. This effort gave 2.78 g clear transparent viscous oil (approx. 70% purity of ethyl 4-(2-chloroacetyl)piperazine-1-carboxylate judged by $^1$H NMR)

which was not purified further. Next, 0.75 g of the clear transparent oil was added to a stirring solution of 1-hydroxyphenazine 5,10-dioxide (150 mg, 0.66 mmol), KI (33 mg, 0.20 mmol), $K_2CO_3$ (274 mg, 1.98 mmol) and 18-Crown-6 (523 mg, 1.98 mmol) in DMF (15 mL). The resulting solution was left stirring overnight at room temperature. The day after, the reaction mixture was diluted with $H_2O$ (200 mL) and 2 mL of HCl (1M aqueous sol.) and the aqueous phase was extracted using DCM (4×30 mL). The pooled organic phases were washed with brine (200 mL), dried over $MgSO_4$ and filtered before solvents were removed in vacuo. Flash column chromatography on silica (5% MeOH/DCM) and subsequent recrystallization from hot EtOH gave 84 mg (30% from 1-hydroxyphenazine 5,10-dioxide) of 1-(2-(4-(ethoxycarbonyl)piperazin-1-yl)-2-oxoethoxy)phenazine 5,10-dioxide as a red powder. $R_f$: 0.16 (5% MeOH/DCM). $^1$H NMR (400 MHz, $CDCl_3$) δ 8.76-8.56 (m, 2H), 8.41 (dd, J=9.0, 1.1 Hz, 1H), 7.89-7.73 (m, 2H), 7.64 (dd, J=9.0, 7.9 Hz, 1H), 7.29 (dd, J=7.9, 1.2 Hz, 1H), 4.97 (s, 2H), 4.13 (q, J=7.1 Hz, 2H), 3.89-3.75 (m, 2H), 3.68-3.43 (m, 6H), 1.24 (t, J=7.1 Hz, 3H). $^{13}$C NMR (101 MHz, $CDCl_3$) δ 166.0, 155.4, 151.7, 138.4, 137.5, 135.8, 131.8, 131.2, 131.1, 130.3, 120.6, 120.3, 114.0, 113.9, 70.6, 61.8, 45.7, 44.2, 43.6, 42.2, 14.8. MS (ESI, positive mode) m/z 449.1 $[M+Na]^+$, HR-MS (ESI, pos. mode) m/z 449.1432 calculated for $C_{21}H_{22}N_4O_6Na$, found m/z 449.1432.

Example 23: Preparation of 1-((morpholine-4-carbonyl)oxy)phenazine 5,10-dioxide

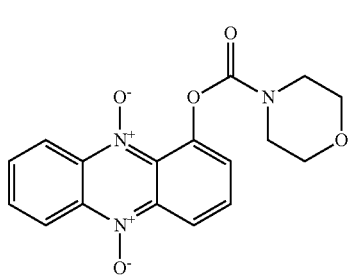 [SMILES: O=C(Oc1cccc2c1[n+]([O-])c1ccccc1[n+]2[O-])N1CCOCC1]

Synthesized according to the general procedure in Example 8 from 1-hydroxphenazine and 4-morpholinecarbonyl chloride. After flash column chromatography on silica 1-3% (MeOH in DCM), the compound was recrystallized from hot EtOH. $^1$H NMR (400 MHz, $CDCl_3$) δ 8.76-8.54 (m, 3H), 7.85-7.75 (m, 2H), 7.71 (dd, J=9.1, 7.5 Hz, 1H), 7.39 (dd, J=7.5, 1.4 Hz, 1H), 4.02-3.76 (m, 6H), 3.75-3.58 (m, 2H). $^{13}$C NMR (101 MHz, $CDCl_3$) δ 153.7, 144, 138.0, 137.4, 135.9, 131.7, 131.4, 131.3, 130.5, 124.6, 120.5, 120.2, 118.3, 66.8, 45.7, 44.8. MS (ESI, positive mode) m/z 364.1 $[M+Na]^+$, HR-MS (ESI, pos. mode) m/z 364.0904 calculated for $C_{17}H_{15}N_3O_5Na$, found m/z 364.0905.

Example 24: Preparation of 1-((pyrrolidine-1-carbonyl)oxy)phenazine 5,10-dioxide

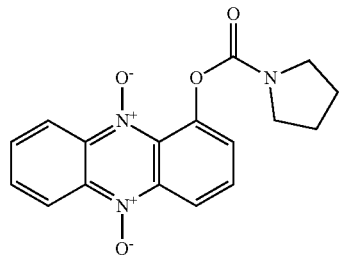 [SMILES: O=C(Oc1cccc2c1[n+]([O-])c1ccccc1[n+]2[O-])N1CCCC1]

Synthesized according to the general procedure in Example 8 from 1-hydroxphenazine and 1-pyrrolidinecarbonyl chloride. Flash column chromatography on silica (0-1% MeOH/DCM) afforded 63 mg (87%) of an orange solid. $R_f$: 0.05 (2% MeOH/DCM). $^1$H NMR (400 MHz, $CDCl_3$) δ 8.69-8.54 (m, 1H), 7.81-7.64 (m, 1H), 7.37 (dd, J=7.5, 1.3 Hz, 0H), 3.75 (t, J=6.7 Hz, 1H), 3.54 (t, J=6.6 Hz, 1H), 2.13-1.94 (m, 1H). $^{13}$C NMR (101 MHz, $CDCl_3$) δ 152.9, 144.1, 137.9, 137.4, 135.7, 131.7, 131.6, 131.0, 130.5, 124.6, 120.5, 120.1, 118.0, 46.8, 46.8, 26.0, 25.2. HRMS (ESI+): Exact mass calculated for $C_{17}H_{15}N_3O_4Na$ $[M+Na]^+$: 348.0955, found 348.0953 (0.4 ppm).

Example 25: Preparation of 1-((4-methylpiperazin-1-ium-1-carbonyl)oxy)phenazine 5,10-dioxide

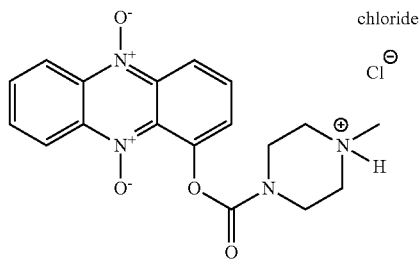 [SMILES: C[NH+]1CCN(C(=O)Oc2cccc3c2[n+]([O-])c2ccccc2[n+]3[O-])CC1 ; [Cl-]]

The compound is prepared using the general procedure in Example 9, and adding 1 equivalent of HCl.

Example 26: Preparation of 1-((dimethylcarbamothioyl)oxy)phenazine 5,10-dioxide

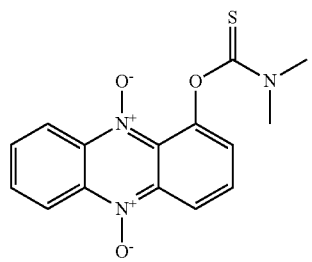 [SMILES: CN(C)C(=S)Oc1cccc2c1[n+]([O-])c1ccccc1[n+]2[O-]]

Synthesized according to the general procedure in Example 8 from 1-hydroxphenazine and dimethylthiocarbamoyl chloride. The crude product is purified by either flash column chromatography on silica or recrystallization from appropriate solvent, such as EtOH.

Example 27: Preparation of 1-hydroxy-6-((2-oxo-3,6,9,12-tetraoxatetradecyl)oxy)phenazine 5,10-dioxide

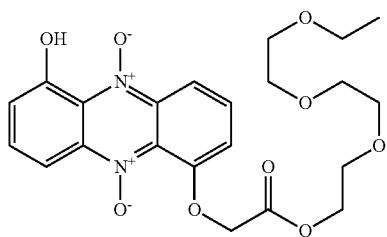 [SMILES: CCOCCOCCOCCOC(=O)COc1cccc2c1[n+]([O-])c1cccc(O)c1[n+]2[O-]]

The compound is prepared as described in Example 6, general procedure.

Example 28: Preparation of N,N-diethyl-2-((6-hydroxy-5,10-di(1-oxidaneyl)-514,1014-phenazin-1-yl)oxy)acetamide

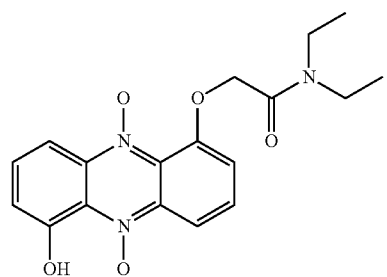

The compound is prepared using the general procedure in Example 19.

Example 29: Preparation of 6-hydroxy-5,10-di(1-oxidaneyl)-514,1014-phenazin-1-yl diisopropylcarbamate

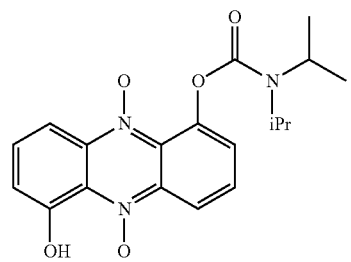

DABCO (300 mg, 2.56 mmol) was added to a suspension of iodinin (300 mg, 1.22 mmol) in dry THE (20 ml) at room temperature under argon. The reaction mixture was stirred for 10 min. followed by addition of diisopropylcarbamoyl chloride (420 mg, 2.56 mmol). The reaction mixture was stirred for 110 min, concentrated and purified directly by flash column chromatography on silica (1-5% MeOH in DCM) affording 120 mg of a deep red solid. HPLC showed unsatisfactory purity and this material was therefore subjected to preparative HPLC to give 31 mg (7%) of the title compound as a bright red solid. $^1$H NMR (400 MHz, CDCl$_3$) δ 8.53 (dd, J=9.1, 1.3 Hz, 1H), 7.95 (dd, J=9.0, 1.3 Hz, 1H), 7.72 (dd, J=9.0, 7.7 Hz, 1H), 7.60 (dd, J=9.0, 7.9 Hz, 1H), 7.37 (dd, J=7.6, 1.3 Hz, 1H), 7.11 (dd, J=7.9, 1.2 Hz, 1H), 4.38 (p, J=6.9 Hz, 1H), 3.87 (p, J=6.8 Hz, 1H), 1.44 (d, J=6.7 Hz, 6H), 1.37 (d, J=6.7 Hz, 6H).

Example 30: Preparation of 1-hydroxy-6-((4-methylpiperazin-1-ium-1-carbonyl)oxy)phenazine 5,10-dioxide

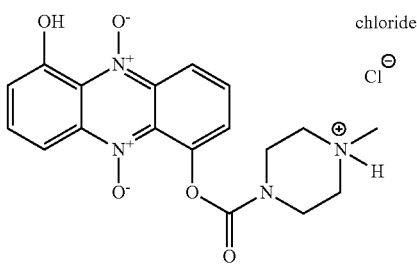 [SMILES: C[NH+]1CCN(C(=O)Oc2cccc3c2[n+]([O-])c2cccc(O)c2[n+]3[O-])CC1 ; [Cl-]]

The compound is prepared using the general procedure in Example 9, and adding 1 equivalent of HCl.

Example 31: Preparation of 6-hydroxy-5,10-di(1-oxidaneyl)-514,1014-phenazin-1-yl methoxy(methyl)carbamate

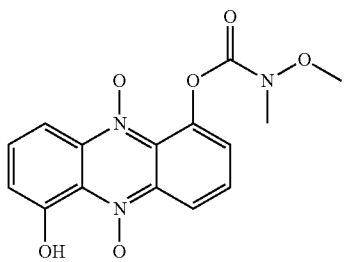

DABCO (580 mg, 5.2 mmol) was added to a suspension of iodinin (600 mg, 2.5 mmol) in dry THE (20 ml) at 0° C. under nitrogen. The reaction mixture was stirred for 5 min. followed by dropwise addition of N-methoxy-N-methylcarbamoyl chloride (0.52 mL, 5.2 mmol). The reaction mixture was stirred for two hours at 0° C. The reaction mixture was poured into 50 mL water and the phases were separated. The aqueous phase was extracted with 4×100 mL EtOAc. The organic phases were combined, dried over Na$_2$SO$_4$, filtered and reduced in vacuo. Purification by flash column chromatography on silica (10-40% EtOAc in heptane) gave 29 mg (4%) of the title compound. $^1$H NMR (400 MHz, CDCl$_3$) δ 14.40 (s, 1H), 8.59 (dd, J=9.2, 1.3 Hz, 1H), 8.00 (dd, J=9.0, 1.1 Hz, 1H), 7.75 (dd, J=9.2, 7.5 Hz, 1H), 7.64 (dd, J=9.0, 7.9 Hz, 1H), 7.44 (dd, J=7.6, 1.3 Hz, 1H), 7.13 (dd, J=7.9, 1.1 Hz, 1H), 3.95 (s, 3H), 3.43 (s, 3H).

Example 32: Preparation of O-(6-hydroxy-5,10-di(1-oxidaneyl)-514,1014-phenazin-1-yl) Dimethylcarbamothioate

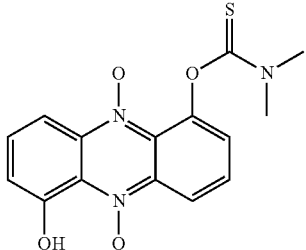

DABCO (1.10 g, 9.84 mmol) was added to a suspension of iodinin (600 mg, 2.46 mmol) in dry THF (20 ml) at 0° C. under nitrogen. The reaction mixture was stirred for 5 min. followed by dropwise addition of dimethylthiocarbamoyl chloride (1.22 g, 9.84 mmol). The reaction mixture was stirred for five hours at 0° C. The reaction mixture was poured into 100 mL water and the phases were separated. The aqueous phase was extracted with 5×100 mL EtOAc. The organic phases were combined, dried over $Na_2SO_4$, filtered and reduced in vacuo. Purification by flash column chromatography on silica (10-40% EtOAc in heptane) gave 61 mg (7%) of a deep red solid. $^1$H NMR (400 MHz, $CDCl_3$) δ 13.54 (s, 1H), 8.49 (dd, J=9.2, 1.2 Hz, 1H), 7.76 (dd, J=9.1, 7.4 Hz, 1H), 7.69 (dd, J=8.7, 7.6 Hz, 1H), 7.62 (dd, J=8.9, 1.3 Hz, 1H), 7.58 (dd, J=7.3, 1.2 Hz, 1H), 7.06 (dd, J=7.5, 1.2 Hz, 1H), 3.60 (s, 3H), 3.54 (s, 3H).

Example 33: Preparation of the building block 1,6-dimethoxyphenazine 5,10-dioxide

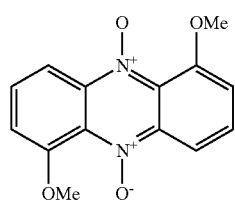 [SMILES: COc1cccc2c1[n+]([O-])c1cccc(OC)c1[n+]2O]

Isolated as a by-product from the same crude material afforded after the work-up described for the synthesis of myxin (example 5a). Flash column chromatography on silica gel (0-3% MeOH/DCM) yielded 30 mg (12%) of the orange solid. $R_f$: 0.06 (100% EtOAc). $^1$H-NMR (600 MHz, $CDCl_3$) δ 8.31 (dd, J=9.1, 1.1 Hz, 2H), 7.60 (dd, J=9.1, 7.9 Hz, 2H), 7.08 (dd, J=7.9, 0.7 Hz, 2H), 4.07 (s, 6H). $^{13}$C-NMR (151 MHz, $CDCl_3$) δ 153.8, 139.7, 130.8, 129.5, 112.3, 110.5, 57.4. HRMS (EI): Exact mass calculated for $C_{14}H_{12}N_2O_4$: 272.0797, found 272.0795 (0.9 ppm). $^1$H- and $^{13}$C-NMR data are in accordance with prior literature.[41]

Example 34: Preparation of 1-(2-(tert-butoxy)-2-oxoethoxy)-6-methoxyphenazine 5,10-dioxide

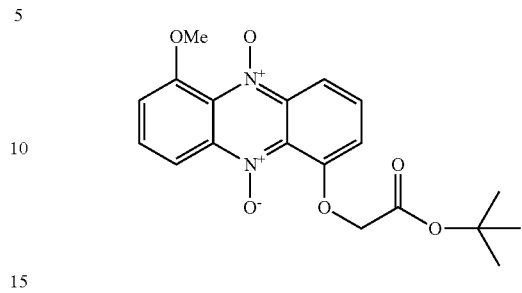

A dry round bottom flask was charged with Myxin (36 mg, 0.14 mmol, 1 eq), $K_2CO_3$ (30 mg, 0.28 mmol, 2 eq) and 18-crown-6-ether (74 mg, 0.28 mmol, 2 eq). The flask was sealed by a rubber septum, shielded from light and flushed thoroughly with argon before anhydrous THF (2.5 mL) was added to disperse the ingredient. After 15 minutes of rotation at rt, tert-butyl bromoacetate (0.07 mL, 0.46 mmol, 4 eq) was added drop wise. The resulting mixture was allowed to rotate for 90 minutes (no starting material observed by TLC: 100% EtOAc). The reaction mixture was diluted by 15 mL of DCM and dry loaded directly on silica. Flash column chromatography (50-100% EtOAc in Heptane) afforded 45 mg (87%) of bright-orange-red solid. $R_f$: 0.1 (100% EtOAc). $^1$H NMR (600 MHz, $CDCl_3$) δ 8.38 (dd, J=9.0, 1.1 Hz, 1H), 8.30 (dd, J=9.0, 1.1 Hz, 1H), 7.58 (ddd, J=16.9, 9.1, 7.9 Hz, 2H), 7.08 (ddd, J=8.0, 4.3, 1.1 Hz, 2H), 4.77 (s, 2H), 4.07 (s, 3H), 1.48 (s, 9H). $^{13}$C NMR (151 MHz, $CDCl_3$) δ 167.05, 153.83, 151.79, 139.87, 139.69, 130.84, 130.35, 130.06, 129.52, 114.41, 114.11, 112.30, 110.48, 82.86, 68.44, 57.36, 28.19. HRMS (TOF ES+): Exact mass calculated for $C_{19}H_{20}N_2O_6Na$ [M+H]+: 373.1399, found 373.1393.

Example 35: Preparation of 1-methoxy-6-(2-(((R)-1-(((R)-1-methoxy-1-oxopropan-2-yl)amino)-1-oxopropan-2-yl)amino)-2-oxoethoxy)phenazine 5,10-dioxide

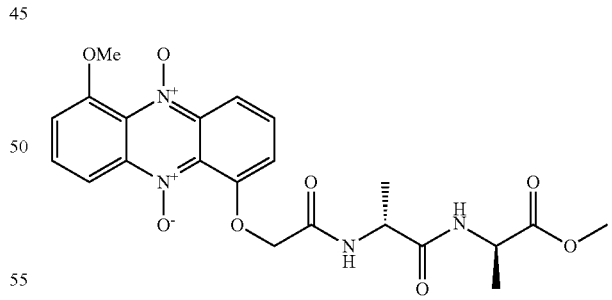

Prepared according to the general procedure in Example 6 from myxin and methyl (2-bromoacetyl)-D-alanyl-D-alaninate. $^1$H NMR (400 MHz, Chloroform-d) δ 9.31 (d, J=7.4 Hz, 1H), 8.38 (dd, J=9.1, 1.1 Hz, 1H), 8.33 (dd, J=9.1, 1.1 Hz, 1H), 7.71-7.59 (m, 2H), 7.16-7.03 (m, 2H), 7.01-6.87 (m, 1H), 4.77 (s, 2H), 4.58 (dt, J=11.5, 7.2 Hz, 2H), 4.09 (s, 3H), 3.70 (s, 3H), 1.60 (d, J=7.0 Hz, 3H), 1.38 (d, J=7.2 Hz, 3H). $^{13}$C NMR (101 MHz, $CDCl_3$) δ 173.4, 171.6, 168.1, 154.0, 151.1, 139.7, 139.6, 131.5, 130.5, 129.8, 129.3, 114.1, 113.5, 112.2, 110.6, 70.1, 57.4, 52.5, 49.2, 48.3, 18.5, 17.3. HRMS (TOF ES+): Exact mass calculated for C$_{22}$H$_{24}$N$_4$O$_8$ Na [M+Na]+: 495.1491, found 495.1489 (−0.57 ppm).

Example 36: Preparation of 1,6-bis(2-(tert-butoxy)-2-oxoethoxy)phenazine 5,10-dioxide

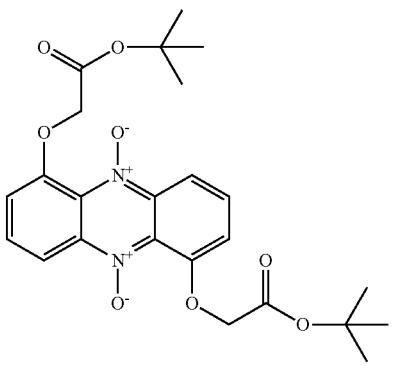 [SMILES: CC(C)(C)OC(=O)COc1cccc2c1[n+]([O-])c1cccc(OCC(=O)OC(C)(C)C)c1[n+]2[O-]]

A dry roundbottom flask was loaded with iodinin (71 mg, 0.29 mmol, 1 eq), K$_2$CO$_3$ (60 mg, 0.44 mmol, 1.5 eq) and 18-crown-6-ether (114 mg, 0.44 mmol, 1.5 eq). The sealed flask was shielded from light and flushed thoroughly with argon before anhydrous THF (4 mL) was added to disperse the ingredients. After 15 minutes of rotation at rt, tert-butyl bromoacetate (0.15 mL, 1.02 mmol) was added dropwise. The resulting mixture was allowed to rotate until no starting material observed by TLC (16 h). The reaction mixture was diluted by 15 mL of DCM and dry loaded directly on silica. Flash column chromatography (10-50% EtOAc in Heptane) afforded 64 mg (47%) of bright-orange-red solid. R$_f$: 0.43 (100% EtOAc). $^1$H-NMR (600 MHz, CDCl$_3$) δ 8.37 (dd, J=9.0, 1.1 Hz, 2H), 7.56 (dd, J=9.1, 7.8 Hz, 2H), 7.07 (dd, J=8.0, 1.2 Hz, 2H), 4.76 (s, 4H), 1.47 (s, 18H). $^{13}$C-NMR (151 MHz, CDCl$_3$) δ 167.0, 151.8, 139.8, 130.4, 130.0, 114.4, 114.1, 82.8, 68.4, 28.2. HRMS (TOF ES+): Exact mass calculated for C$_{24}$H$_{28}$N$_2$O$_8$Na [M+Na]$^+$: 495.1743, found 495.1729 (2.90 ppm).

Example 37: Preparation of 1,6-bis(carboxymethoxy)phenazine 5,10-dioxide

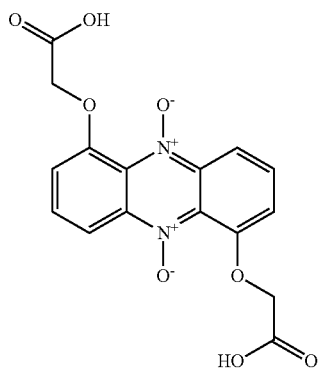 [SMILES: O=C(O)COc1cccc2c1[n+]([O-])c1cccc(OCC(=O)O)c1[n+]2[O-]]

1,6-bis(2-(tert-butoxy)-2-oxoethoxy)phenazine 5,10-dioxide (113 mg, 0.24 mmol) from example 36 was dissolved in DCM (4 mL) and pipetted dropwise to stirring aqueous solution of H$_3$PO$_4$ (3 mL; ≥85 wt. % in H$_2$O). The resulting mixture was stirred for 5 h at room temperature before the mixture was diluted by 50 mL of sat. NaHCO$_3$ aqueous solution and placed in a separatory funnel. The aqueous phase (orange colored) was washed with 2×20 mL of DCM in order to wash out unreacted starting material. The pH of the aqueous solution was adjusted by dropwise addition of HCl (37% w/v) and the precipitated product flittered and dried affording 76 mg (88%) of the wanted orange solid. No further purification was necessary. $^1$H-NMR (600 MHz, DMSO-d$_6$) δ 13.17 (s, 2H), 8.17 (dd, J=9.1, 1.1 Hz, 2H), 7.72 (dd, J=9.0, 7.9 Hz, 2H), 7.30 (dd, J=8.0, 1.2 Hz, 2H), 4.91 (s, 4H). $^{13}$C-NMR (151 MHz, DMSO-d$_6$) δ 169.6, 151.4, 139.1, 130.7, 129.3, 114.7, 112.7, 67.6. HRMS (TOF ES$^+$): Exact mass calculated for C$_{16}$H$_{10}$N$_2$O$_8$Na [M−2H+Na]$^-$: 381.0334, found 381.0339 (1.08 ppm).

Example 38: Preparation of 1,6-bis((dimethylcarbamoyl)oxy)phenazine 5,10-dioxide

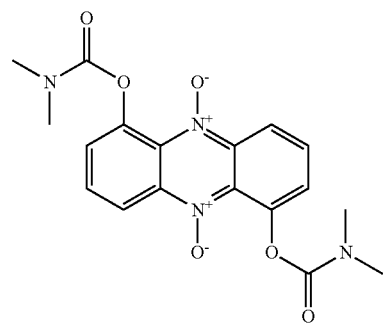

DABCO (10 mmol) is added to a suspension of iodinin (2 mmol) in dry THF (30 mL) 0° C. under nitrogen. The reaction mixture is stirred for 5 min followed by dropwise addition of dimethylcarbamoyl chloride (10 mmol). The resulting mixture is stirred for 5 hours or until the starting material is consumed judged by TLC. The reaction mixture is quenched with water (250 mL) and the aqueous phase extracted using DCM (4×40 mL). The pooled organic phase is dried over MgSO$_4$, filtered and reduced in vacuo. Purification is undertaken by flash column chromatography on silica, C18-silica or by recrystallization from appropriate solvent or mixture of solvents.

Example 39: Preparation of 1,6-bis((isobutoxycarbonyl)oxy)phenazine 5,10-dioxide

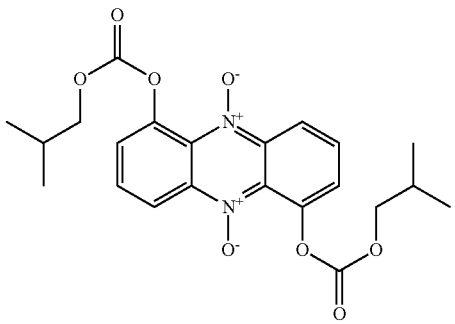 [SMILES: CC(C)COC(=O)Oc1cccc2c1[n+]([O-])c1cccc(OC(=O)OCC(C)C)c1[n+]2[O-]]

A dry round bottomed flask was charged with iodinin (152 mg, 90% by $^1$H NMR, 0.56 mmol, 1 eq) under argon atm at 25° C. and dispersed in anhydrous toluene (10 mL). The dispersion was cooled down to 0° C. before DMAP (21 mg, 0.17 mmol, 0.3 eq) was added followed by Et$_3$N (117 μL, 0.84 mmol, 1.5 eq). The resulting mixture was allowed to rotate for 10 min before isobutyl chloroformate (37 μL, 0.31 mmol, 0.6 eq) was added. The mixture was allowed rotating for 1 h before another portion of isobutyl chloroformate was added (37 μL, 0.31 mmol, 0.6 eq). This addition was repeated once more after 60 minutes. The resulting reaction mixture was allowed to reach rt and quenched with H$_2$O (50 mL) and the aqueous phase extracted with DCM (3×25 mL). the combined organic phases were washed with 0.1M HCl, brine and filtered with MgSO$_4$. Flash column chromatography on silica (5-20% EtOAc/Heptane) afford 68 mg (27%) of the orange solid. R$_f$: 0.66 (1:1 EtOAc/Heptane). $^1$H NMR (400 MHz, Chloroform-d) δ 8.59 (dd, J=9.2, 1.3 Hz, 2H), 7.70 (dd, J=9.1, 7.6 Hz, 2H), 7.46 (dd, J=7.6, 1.3 Hz, 2H), 4.16 (d, J=6.7 Hz, 4H), 2.24-2.08 (m, 2H), 1.05 (d, J=6.7 Hz, 12H). $^{13}$C NMR (101 MHz, CDCl$_3$) δ 153.20, 143.44, 139.10, 130.80, 130.62, 124.42, 118.98, 77.36, 75.79, 27.96, 19.07. HRMS (TOF ES+): Exact mass calculated for C$_{22}$H$_{24}$N$_2$O$_8$ Na [M+Na]$^+$: 467.1430, found 467.1421 (−2.00 ppm).

Example 40: Preparation of the building block 2-bromo-1-hydroxyphenazine 5,10-dioxide

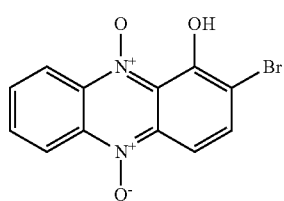 [SMILES: [O-][n+]1c2ccccc2[n+](O)c2c(O)c(Br)ccc21]

A round bottomed flash was charged with 1-hydroxyphenazine 5,10-dioxide (200 mg, 0.87 mmol) dissolved in DCM (9 mL). NBS (171 mg, 0.96 mmol) and the mixture stirred at rt under open air for 2 hours. The reaction mixture was diluted with 20 mL DCM and absorbed onto silica in vacuo. Flash column chromatography on silica (100% DCM) afforded 196 mg (73%) of a deep-red powder. R$_f$: 0.34 (100% DCM). $^1$H NMR (400 MHz, CDCl$_3$) δ 15.54 (s, 1H), 8.73-8.60 (m, 2H), 7.97 (d, J=9.6 Hz, 1H), 7.91-7.82 (m, 3H). $^{13}$C NMR (101 MHz, CDCl$_3$) δ 151.0, 136.5, 136.4, 136.09, 134.0, 132.5, 131.9, 126.4, 120.2, 119.5, 109.3, 109.0. HRMS (ESI+): Exact mass calculated for C$_{12}$H$_7$N$_2$O$_3$BrNa [M+Na]$^+$: 328.9532, found 328.9533 (−0.1 ppm).

Example 41: Preparation of the building block 2-bromo-1-methoxyphenazine 5,10-dioxide

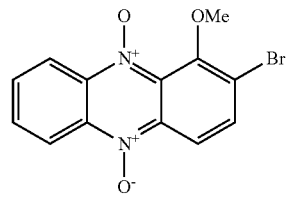 [SMILES: COc1c(Br)ccc2c1[n+](O)c1ccccc1[n+]2[O-]]

Synthesized in accordance to general procedure 6 starting from 2-bromo-1-hydroxyphenazine 5,10-dioxide (55 mg, 0.18 mmol) using dimethyl sulfate as a methylating reagent. Flash column chromatography on silica (0-10% EtOAc/DCM) afforded 26 mg (45%) of an orange solid. R$_f$: 0.21. $^1$H NMR (600 MHz) δ 8.71-8.63 (m, 2H), 8.43 (d, J=9.6 Hz, 1H), 7.87 (d, J=9.6 Hz, 1H), 7.85-7.79 (m, 2H), 4.11 (s, 3H). $^{13}$C NMR (151 MHz, CDCl$_3$) δ 150.1, 137.9, 137.4, 135.7, 135.2, 134.0, 131.8, 131.7, 121.2, 120.6, 120.3, 117.1, 63.1.

Example 43: Preparation of 2-bromo-1-((4-methylpiperazine-1-carbonyl)oxy)phenazine 5,10-dioxide

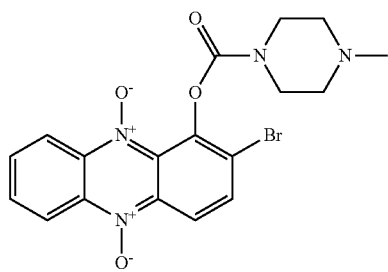 [SMILES: CN1CCN(C(=O)Oc2c(Br)ccc3c2[n+]([O-])c2ccccc2[n+]3[O-])CC1]

Synthesized according to general procedure in Example 8 starting from 53 mg (0.17 mmol) of 2-bromo-1-hydroxyphenazine 5,10-dioxide. Flash column chromatography on silica (5% MeOH/DCM) afforded 74 mg (>99%) of an orange solid. R$_f$: 0.20 (5% MeOH/DCM). $^1$H NMR (400 MHz, CDCl$_3$) δ 8.67-8.57 (m, 2H), 8.51 (d, J=9.7 Hz, 1H), 7.89 (d, J=9.7 Hz, 1H), 7.86-7.73 (m, 2H), 4.09-3.59 (m, 4H), 2.93-2.49 (m, 4H), 2.43 (s, 3H). $^{13}$C NMR (101 MHz, CDCl$_3$) δ 152.0, 141.4, 137.7, 136.9, 135.8, 134.4, 132.3, 131.9, 131.6, 121.1, 120.6, 120.2, 118.7, 54.8, 54.7, 46.3, 45.1, 44.5. HRMS (ESI+): Exact mass calculated for C$_1$H$_1$N$_4$O$_4$BrNa [M+Na]$^+$: 433.0506, found 433.0506 (0.1 ppm).

Example 44: Preparation of the building block 1-hydroxy-2-iodophenazine 5,10-dioxide

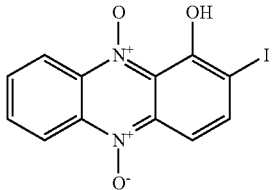 [SMILES: [O-][n+]1c2ccccc2[n+](O)c2c(O)c(I)ccc21]

A round bottomed flash was charged with 1-hydroxyphenazine 5,10-dioxide (200 mg, 0.87 mmol) dissolved in DCM (9 mL). NIS (217 mg, 0.96 mmol) was added and the mixture stirred at rt under open air for 2 hours. The reaction mixture was diluted with 20 mL DCM and absorbed onto silica in vacuo. Flash column chromatography on silica (100% DCM) afforded 305 mg (98%) of a deep-purple powder. $R_f$: 0.61 (100% DCM). $^1$H NMR (400 MHz, CDCl$_3$) δ 15.75 (s, 1H), 8.72-8.55 (m, 2H), 8.03 (d, J=9.4 Hz, 1H), 7.84 (d, J=9.4 Hz, 1H). $^{13}$C NMR (101 MHz, CDCl$_3$) δ 153.54, 141.49, 137.19, 136.13, 133.65, 132.43, 131.92, 125.47, 120.11, 119.59, 109.92, 83.15. HRMS (ESI+): Exact mass calculated for $C_{12}H_7N_2O_3INa$ [M+Na]$^+$: 376.9394, found 376.9394 (−0.1 ppm).

Example 45: Preparation of the building block 2-iodo-1-methoxyphenazine 5,10-dioxide

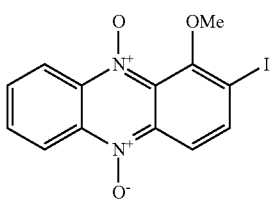 [SMILES: COc1c(I)ccc2c1[n+](O)c1ccccc1[n+]2[O-]]

Synthesized in accordance to general procedure in Example 6 starting from 1-hydroxy-2-iodophenazine 5,10-dioxide (29 mg, 0.08 mmol) using dimethyl sulfate as a methylating reagent. Flash column chromatography on silica (100% DCM) afforded 13 mg (43%) of an orange solid. $R_f$: 0.13. $^1$H NMR (600 MHz, CDCl$_3$) δ 8.72-8.69 (m, 2H), 8.69-8.64 (m, 2H), 8.30 (d, J=9.4 Hz, 1H), 8.08 (d, J=9.5 Hz, 1H), 7.86-7.79 (m, 2H), 4.08 (s, 3H). $^{13}$C NMR (151 MHz, CDCl$_3$) δ 152.7, 140.4, 138.2, 137.7, 135.8, 133.3, 131.9, 131.7, 120.8, 120.3, 117.6, 96.7, 63.2.

Example 46: Preparation of 2-iodo-1-((pyrrolidine-1-carbonyl)oxy)phenazine 5,10-dioxide

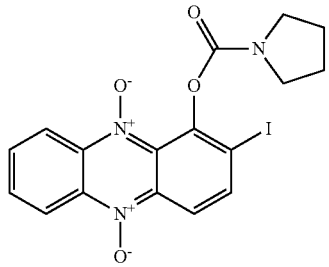 [SMILES: O=C(Oc1c(I)ccc2c1[n+]([O-])c1ccccc1[n+]2[O-])N1CCCC1]

Synthesized according to general procedure in Example 8 starting from 53 mg (0.15 mmol) of compound 119. Flash column chromatography on silica (1% MeOH/DCM) afforded an orange solid which was dissolved in minimum amount of a mixture of CHCl$_3$ and heptane. The resulting mixture was then concentrated in vacuo removing CHCl$_3$. The orange precipitate was then filtered and dried affording 35 mg (52%) of orange powder. $R_f$: 0.38 (5% MeOH/DCM). $^1$H NMR (400 MHz, CDCl$_3$) δ 8.69-8.56 (m, 2H), 8.38 (d, J=9.5 Hz, 1H), 8.08 (d, J=9.5 Hz, 1H), 7.90-7.72 (m, 2H), 3.97-3.74 (m, 2H), 3.71-3.49 (m, 2H), 2.22-1.92 (m, 4H). $^{13}$C NMR (101 MHz, CDCl$_3$) δ 151.4, 144.4, 139.6, 137.7, 137.6, 135.9, 132.0, 131.9, 131.5, 120.8, 120.2, 118.8, 97.0, 47.0, 46.9, 26.0, 25.3. HRMS (ESI+): Exact mass calculated for $C_{17}H_{14}N_3O_4INa$ [M+Na]$^+$: 473.9921, found 473.9920 (0.2 ppm).

Example 47: Preparation of 2-iodo-1-((4-methylpiperazine-1-carbonyl)oxy)phenazine 5,10-dioxide

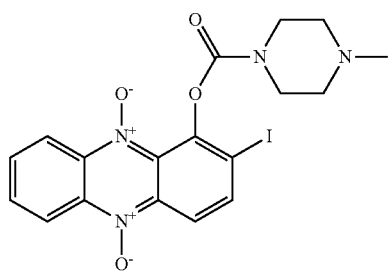 [SMILES: CN1CCN(C(=O)Oc2c(I)ccc3c2[n+]([O-])c2ccccc2[n+]3[O-])CC1]

Synthesized according to the general procedure in example 8 starting from 27 mg (0.08 mmol) of 1-hydroxy-2-iodophenazine 5,10-dioxide. Flash column chromatography on silica afforded 20 mg (54%) of an orange solid. $R_f$: 0.16 (5% MeOH/DCM). $^1$H NMR (300 MHz, CDCl$_3$) δ 8.71-8.58 (m, 2H), 8.39 (d, J=9.4 Hz, 1H), 8.08 (d, J=9.6 Hz, 1H), 7.89-7.74 (m, 2H), 4.06-3.59 (m, 4H), 2.94-2.50 (m, 4H), 2.45 (s, 3H). $^{13}$C NMR (101 MHz, CDCl$_3$) δ 151.9, 144.3, 139.6, 137.7, 137.5, 135.9, 131.9, 131.8, 131.6, 120.8, 120.3, 119.0, 96.9, 54.9, 54.7, 46.3, 45.2, 44.5. (ESI+): Exact mass calculated for $C_{18}H_{18}N_4O_4I$ [M+H]$^+$: 481.0367, found 481.0366 (0.3 ppm)

Example 48: Preparation of the building block 1-hydroxy-7,8-dimethylphenazine 5,10-dioxide

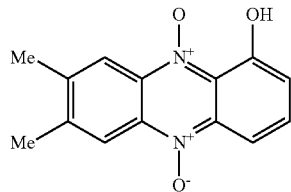 [SMILES: Cc1cc2c(cc1C)[n+](O)c1c(O)cccc1[n+]2[O-]]

The compound is prepared in 1 gram scale using the procedure in Example 4b.

Example 49: Preparation of the building block 1-methoxy-7,8-dimethylphenazine 5,10-dioxide

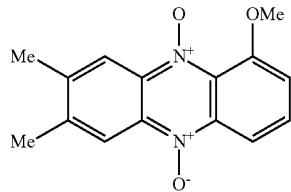 [SMILES: COc1cccc2c1[n+](O)c1cc(C)c(C)cc1[n+]2[O-]]

Synthesized in accordance with the general procedure 6 starting from 1-hydroxy-7,8-dimethylphenazine 5,10-dioxide (36 mg, 0.14 mmol) using MeI as a methylating reagent. The reaction time was 3 h. Flash column chromatography on silica (1% MeOH/DCM) afforded 26 mg (69%) of an orange solid. $R_f$: 0.07 (1% MeOH/DCM). $^1$H NMR (600 MHz, CDCl$_3$) δ 8.43 (s, 1H), 8.41 (s, 1H), 8.32 (dd, J=9.0, 1.1 Hz, 1H), 7.62 (dd, J=9.0, 7.9 Hz, 1H), 7.05 (d, J=7.8 Hz, 1H), 4.08 (s, 3H), 2.63-2.46 (m, 6H). $^{13}$C NMR (151 MHz, CDCl$_3$) δ 154.1, 143.6, 142.7, 138.0, 136.1, 134.4, 130.8, 129.6, 119.4, 118.9, 112.0, 109.7, 57.4, 20.7, 20.6. HRMS (ESI$^+$): Exact mass calculated for C$_{15}$H$_{14}$N$_2$O$_3$Na [M+Na]$^+$: 293.0897, found 293.0896 (0.1 ppm).

Example 50: Preparation of 1-(2-(diethylamino)-2-oxoethoxy)-7,8-dimethylphenazine 5,10-dioxide

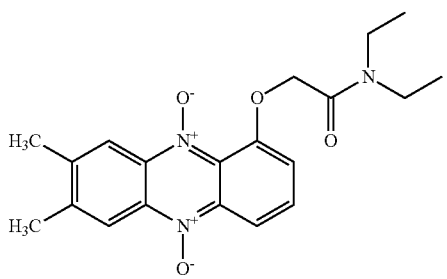 [SMILES: CCN(CC)C(=O)COc1cccc2c1[n+]([O-])c1cc(C)c(C)cc1[n+]2[O-]]

Prepared in accordance with the general procedure in Example 6 from 1-hydroxy-7,8-dimethylphenazine 5,10-dioxide (69 mg scale). Flash column chromatography on silica (0-5% MeOH/DCM) and subsequent recrystallization from hot EtOH afforded 51 mg (51%). $R_f$ 0.30 (5% MeOH/DCM). $^1$H NMR (400 MHz, CDCl$_3$) δ 8.44-8.41 (m, 2H), 8.39 (dd, J=9.1, 1.2 Hz, 1H), 7.61 (dd, J=9.0, 7.8 Hz, 1H), 7.32 (dd, J=7.9, 1.2 Hz, 1H), 4.97 (s, 2H), 3.56 (q, J=7.1 Hz, 2H), 3.42 (q, J=7.1 Hz, 2H), 2.57-2.45 (m, 6H), 1.22 (t, J=7.1 Hz, 3H), 1.13 (t, J=7.1 Hz, 3H). $^{13}$C NMR (101 MHz, CDCl$_3$) δ 166.44, 152.29, 143.56, 142.79, 138.00, 136.19, 134.38, 130.75, 130.14, 119.38, 118.99, 114.63, 113.72, 70.75, 41.69, 40.51, 20.71, 20.62, 14.51, 12.99. HRMS (ESI+): Exact mass calculated for C$_{20}$H$_{23}$N$_3$O$_4$Na [M+Na]$^+$: 392.1581, found 392.1581 (−0.2 ppm).

Example 51: Preparation of 1-((dimethylcarbamoyl)oxy)-7,8-dimethylphenazine 5,10-dioxide

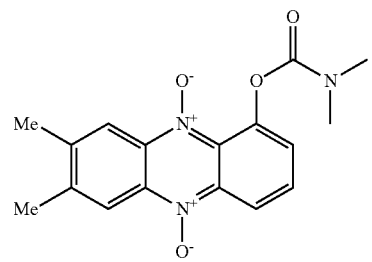 [SMILES: Cc1cc2c(cc1C)[n+]([O-])c1c(OC(=O)N(C)C)cccc1[n+]2[O-]]

The compound is synthesized according to the general procedure in Example 8 from Example 48 using dimethylcarbamoyl chloride as the alkylating agent. The product is purified by flash column chromatography on silica using appropriate mixture of solvents as eluent or is recrystallized from appropriate solvent or mixture of solvents.

Example 52: Preparation of 7,8-dimethyl-1-((pyrrolidine-1-carbonyl)oxy)phenazine 5,10-dioxide

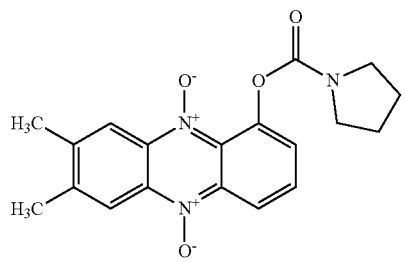 [SMILES: Cc1cc2c(cc1C)[n+]([O-])c1c(OC(=O)N3CCCC3)cccc1[n+]2[O-]]

Prepared in accordance with the general procedure in Example 8 from 1-hydroxy-7,8-dimethylphenazine 5,10-dioxide (69 mg scale). Flash column chromatography on silica (0-5% MeOH/DCM) and subsequent recrystallization from hot EtOH afforded 35 mg (37%) of orange flakes. $R_f$: 0.52 (5% MeOH/DCM). $^1$H NMR (400 MHz, CDCl$_3$) δ 8.63 (dd, J=9.1, 1.4 Hz, 1H), 8.43 (s, 1H), 8.39 (s, 1H), 7.68 (dd, J=9.1, 7.5 Hz, 1H), 7.36 (dd, J=7.5, 1.4 Hz, 1H), 3.78 (t, J=6.7 Hz, 2H), 3.57 (t, J=6.7 Hz, 2H), 2.53 (s, 3H), 2.50 (s, 3H), 2.13-1.94 (m, 4H). $^{13}$C NMR (101 MHz, CDCl$_3$) δ 153.1, 144.1, 143.4, 142.9, 137.6, 136.2, 134.5, 131.4, 130.0, 124.4, 119.4, 119.0, 118.1, 46.8, 26.1, 25.3, 20.6, 20.6. HRMS (ESI+): Exact mass calculated for C$_{19}$H$_{19}$N$_3$O$_4$Na [M+Na]$^+$: 376.1268, found 376.1267 (0.1 ppm).

Example 53: Preparation of the building block 7,8-dichloro-1-hydroxyphenazine 5,10-dioxide

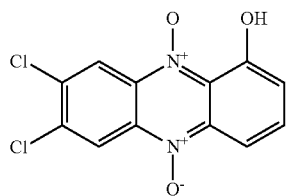 [SMILES: [O-][n+]1c2cc(Cl)c(Cl)cc2[n+](O)c2c(O)cccc21]

The compound is prepared in 1 gram scale using the procedure in Example 4d.

Example 54: Preparation of the building block 7,8-dichloro-1-methoxyphenazine 5,10-dioxide

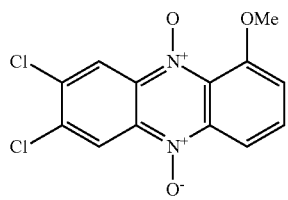 [SMILES: COc1cccc2c1[n+](O)c1cc(Cl)c(Cl)cc1[n+]2[O-]]

The compound is synthesized according to the general procedure in Example 5 from Example 53 using methyl iodide as the alkylating agent. The product is purified by flash column chromatography on silica using appropriate mixture of solvents as eluent or is recrystallized from appropriate solvent or mixture of solvents.

Example 55: Preparation of 7,8-dichloro-1-(((dimethylcarbamoyl)oxy)phenazine 5,10-dioxide

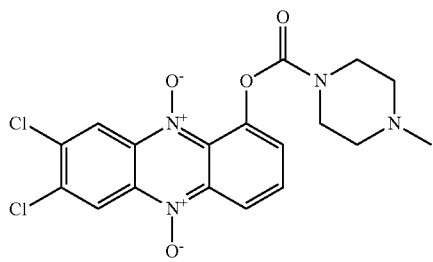 [SMILES: CN1CCN(C(=O)Oc2cccc3c2[n+]([O-])c2cc(Cl)c(Cl)cc2[n+]3[O-])CC1]

The compound is prepared in 1 gram scale using the procedure in Example 8f.

Example 56: Preparation of 7,8-dibromo-1-hydroxyphenazine 5,10-dioxide

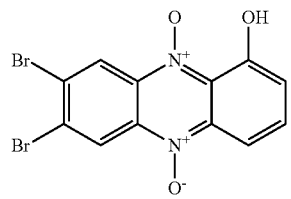

The compound is prepared in 1 gram scale using the procedure in Example 4e.

Example 57: Preparation the building block of 7,8-dibromo-1-methoxyphenazine 5,10-dioxide

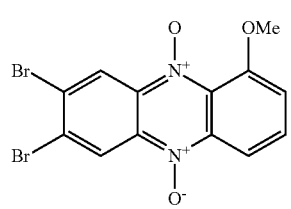 [SMILES: COc1cccc2c1[n+](O)c1cc(Br)c(Br)cc1[n+]2[O-]]

The compound is synthesized according to the general procedure in Example 5 from Example 56 using methyl iodide as the alkylating agent. The product is purified by flash column chromatography on silica using appropriate mixture of solvents as eluent or is recrystallized from appropriate solvent or mixture of solvents.

Example 58: Preparation of 7,8-dibromo-1-(((dimethylcarbamoyl)oxy)phenazine 5,10-dioxide

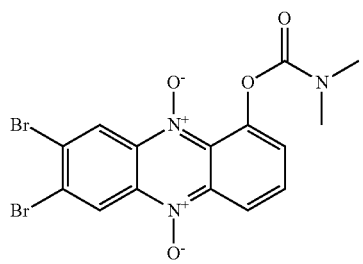 [SMILES: CN(C)C(=O)Oc1cccc2c1[n+]([O-])c1cc(Br)c(Br)cc1[n+]2[O-]]

The compound is synthesized according to the general procedure in Example 8 from Example 56 using dimethylcarbamoyl chloride as the alkylating agent. The product is purified by flash column chromatography on silica using appropriate mixture of solvents as eluent or is recrystallized from appropriate solvent or mixture of solvents.

Example 59: Preparation of 7,8-dibromo-1-((4-methylpiperazine-1-carbonyl)oxy)phenazine 5,10-dioxide

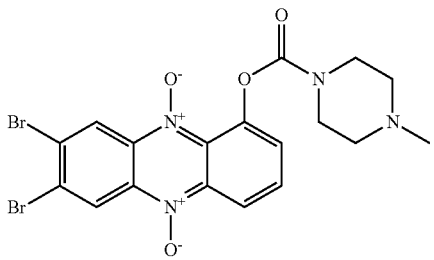

The compound is prepared in 1 gram scale using the procedure in Example 8g.

Example 60: Preparation of the building block of 2-hydroxyphenazine 5,10-dioxide

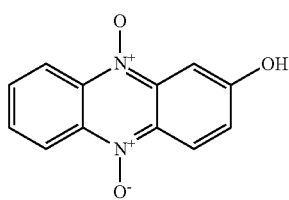 [SMILES: [O-][n+]1c2ccccc2[n+](O)c2cc(O)ccc21]

The title compound was prepared according to a reported procedure by Ley, K. et al. (*Angew. Chem. Int. Ed. Engl.*, 1969, 8, 596-597). A suspension of benzofuroxan (12.36 g, 91 mmol) and hydroquinone (11.0 g, 100 mmol) in water (300 mL) was treated with a catalytic amount of sodium hydroxide (200 mg, 5 mmol) for 24 h. Acidification with glacial acetic acid (5 mL, dropwise) and subsequent isolation of the precipitated product on a Buchner funnel gave the product as a red solid paste with satisfactory purity. $^1$H NMR (400 MHz, DMSO-$d_6$) δ 11.31 (s, 1H), 8.58-8.50 (m, 2H), 8.48 (d, J=9.6 Hz, 1H), 7.95-7.81 (m, 2H), 7.76 (d, J=2.6 Hz, 1H), 7.49 (dd, J=9.6, 2.6 Hz, 1H). MS (ESI, positive mode) m/z 251.0 [M+Na]$^+$, HR-MS (ESI, pos. mode) m/z 251.0427 calculated for $C_{12}H_8N_2O_3Na$, found m/z 251.0428.

Example 61: Preparation of the building block 2-methoxyphenazine 5,10-dioxide

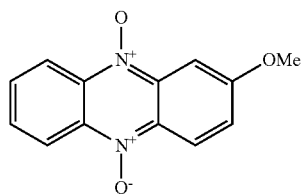 [SMILES: COc1ccc2c(c1)[n+](O)c1ccccc1[n+]2[O-]]

The title compound was prepared by treatment of 2-hydroxyphenazine 5,10-dioxide (600 mg, 2.62 mmol) with potassium carbonate (545 mg, 3.94 mmol), 18-crown-6-ether (1.04 g, 3.94 mmol) and dimethylsulfate (0.62 mL, 6.6 mmol) in DMF (20 mL) solution under argon atmosphere. The resulting mixture was quenched using HCl (0.1 M aqueous sol, 200 mL). The aqueous layer was extracted with DCM (4×40 mL). The pooled organic phases were washed with brine, dried over MgSO$_4$, filtered and concentrated in vacuo. The resulting crude compound was purified by flash column chromatography on silica (2-5% MeOH in DCM) and subsequent recrystallization from hot EtOH afforded 300 mg (47%) of a red powder. $^1$H NMR (400 MHz, CDCl$_3$) δ 8.72 (ddd, J=8.3, 6.4, 1.4 Hz, 2H), 8.62 (d, J=9.7 Hz, 1H), 7.94 (d, J=2.6 Hz, 1H), 7.87-7.74 (m, 2H), 7.44 (dd, J=9.7, 2.6 Hz, 1H), 4.06 (s, 3H). $^{13}$C NMR (101 MHz, CDCl$_3$) δ 162.7, 137.6, 136.3, 135.0, 132.4, 131.5, 130.4, 125.8, 121.9, 120.3, 120.0, 97.0, 56.7. MS (ESI, positive mode) m/z 265.1 [M+Na]$^+$, HR-MS (ESI, pos. mode) m/z 265.0584 calculated for $C_{13}H_{10}N_2O_3Na$, found m/z 265.0584.

Example 62: Preparation of 2-(2-ethoxy-2-oxoethoxy)phenazine 5,10-dioxide

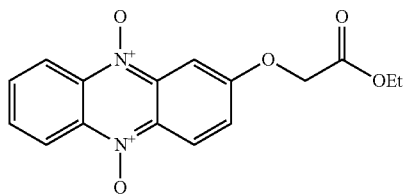 [SMILES: CCOC(=O)COc1ccc2c(c1)[n+](O)c1ccccc1[n+]2O]

The title compound was prepared by treatment of 2-hydroxyphenazine 5,10-dioxide (500 mg, 2.19 mmol) with potassium carbonate (454.7 mg, 3.29 mmol), 18-crown-6-ether (869.6 mg, 3.29 mmol) and ethyl bromoacetate (0.5 mL, 4.4 mmol) in 10 mL dimethylformamide. After quench with water, the product was extracted four times with 40 mL dichloromethane. The crude product was purified on a silica column, eluted with 1:1 ethyl acetate/n-hexane. Subsequent removal of the solvent under reduced pressure gave the product as an orange solid, 130 mg (19%). $^1$H NMR (400 MHz, CDCl$_3$) δ 8.71 (m, 2H), 8.67 (d, J=9.7 Hz, 1H), 7.90 (d, J=2.7 Hz, 1H), 7.87-7.76 (m, 2H), 7.57 (dd, J=9.8, 2.7 Hz, 1H), 4.87 (s, 2H), 4.32 (q, J=7.1 Hz, 2H), 1.34 (t, J=7.1 Hz, 3H). $^{13}$C NMR (101 MHz, CDCl$_3$) δ 167.4, 160.6, 137.0, 136.3, 135.2, 132.7, 131.7, 130.6, 125.6, 122.3, 120.3, 120.1, 98.1, 65.8, 62.1, 14.3. MS (ESI, positive mode) m/z 337.1 [M+Na]$^+$, HR-MS (ESI, pos. mode) m/z 337.0795 calculated for $C_{16}H_{14}N_2O_5Na$, found m/z 337.0795.

Example 63: Preparation of 2-((4-methylpiperazine-1-carbonyl)oxy)phenazine 5,10-dioxide

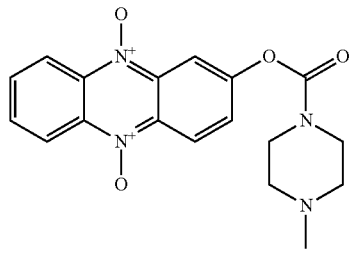 [SMILES: CN1CCN(C(=O)Oc2ccc3c(c2)[n+](O)c2ccccc2[n+]3O)CC1]

To a flask, cooled on an icebath, charged with 2-hydroxyphenazine 5,10-dioxide (800 mg, 3.50 mmol) and DABCO (2.46 g, 21 mmol) as a suspension in 100 mL tetrahydrofuran under an argon atmosphere, 4-methyl-1-piperazinecarbonyl chloride hydrochloride salt (2.09 g, 10.5 mmol) was added. The cooling bath was removed, and the reaction mixture was stirred for 16 h, after which 200 mL water was added to quench the reaction. Extraction four times with 40 mL dichloromethane and drying over $MgSO_4$ (s), afforded a crude product which was purified on a silica column eluting with 5% methanol in dichloromethane. The product was obtained after removal of solvent under reduced pressure as an orange solid, 446 mg (36%). $^1H$ NMR (600 MHz, $CDCl_3$) δ 8.77-8.65 (m, 3H), 8.43 (d, J=2.4 Hz, 1H), 7.88-7.78 (m, 2H), 7.67 (dd, J=9.6, 2.4 Hz, 1H), 3.76 (t, J=4.9 Hz, 2H), 3.64 (t, J=5.0 Hz, 2H), 2.56-2.45 (m, 4H), 2.37 (s, 3H). $^{13}C$ NMR (151 MHz, $CDCl_3$) δ 153.8, 152.3, 136.4, 136.3, 135.8, 133.9, 131.6, 131.3, 127.7, 121.7, 120.3, 120.2, 111.1, 54.8, 54.6, 46.3, 44.8, 44.2. MS (ESI, positive mode) m/z 355.1 $[M+H]^+$, HR-MS (ESI, pos. mode) m/z 355.1401 calculated for $C_1H_{19}N_4O_4$, found m/z 355.1401.

Example 64: Preparation of the building block 7-hydroxy-2,3-dimethylphenazine 5,10-dioxide

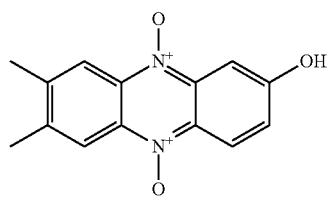 [SMILES: Cc1cc2c(cc1C)[n+](O)c1cc(O)ccc1[n+]2O]

5,6-Dimethylbenzo[c][1,2,5]oxadiazole 1-oxide (820.2 mg, 4.997 mmol), prepared by the method described by Shoker et al. (*Org. Lett.* 2012, 14, 3704-3707), and hydroquinone (605.4 mg, 5.498 mmol) was suspended in 30 mL water, and stirred for 24 h after addition of a catalytic amount of sodium hydroxide (17.2 mg, 0.43 mmol). The formed precipitate was isolated by way of suction filtration and recrystallized from a boiling mixture of 150 mL absolute ethanol and 30 mL methanol. After being allowed to stand in room temperature for some hours, a brick red powder was collected on a Buchner funnel and subsequently dried under vacuum to afford 105.6 mg (8%) of the title compound. $^1H$ NMR (400 MHz, DMSO-$d_6$) δ 11.18 (br s, 1H), 8.43 (d, J=9.6 Hz, 1H), 8.27 (s, 1H), 8.26 (s, 1H), 7.73 (d, J=2.5 Hz, 1H), 7.44 (dd, J=9.6, 2.6 Hz, 1H), 2.49 (s, 3H), 2.48 (s, 3H). $^{13}C$ NMR (100 MHz, DMSO-$d_6$) δ 160.1, 142.6, 141.2, 136.3, 134.2, 132.6, 130.6, 124.4, 121.6, 118.2, 117.9, 99.7, 20.0, 19.9. MS (ESI, positive mode) m/z 279.1 $[M+Na]^+$, HR-MS (ESI, pos. mode) m/z 279.0740 calculated for $C_{14}H_{12}N_2O_3Na$, found m/z 279.0741.

Example 65: Preparation of 2,3-dimethyl-7-((4-methylpiperazine-1-carbonyl)oxy)phenazine 5,10-dioxide

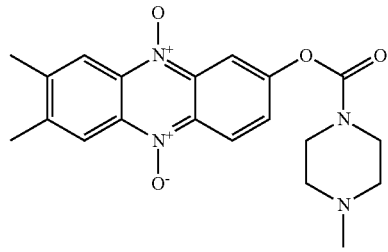 [SMILES: Cc1cc2c(cc1C)[n+](O)c1cc(OC(=O)N3CCN(C)CC3)ccc1[n+]2[O-]]

To a flask, cooled on an icebath, charged with 5,6-dimethylbenzo[c][1,2,5]oxadiazole 1-oxide (245 mg, 1.5 mmol) and hydroquinone (181 mg, 1.6 mmol) in $H_2O$ (30 mL) was added sodium hydroxide (cat, ~5 mg). The resulting mixture was stirred for 3 hours before neutralized with glacial acetic acid (~10 drops). The precipitated crude compound was filtered, washed with water and dried. The obtained crude material was then transferred to a dry round bottom flask and dispersed in THF (10 mL) under argon atmosphere. 4-Methyl-1-piperazinecarbonyl chloride hydrochloride salt (597 mg, 3 mmol) and DABCO (703 mg, 6 mmol) were added. After removal of the cooling bath, the reaction was allowed to stir until consumption of the starting material, after which water (200 mL) was added to quench the reaction. The aqueous phase was extracted using DCM (3×30 mL) and the pooled organic phases were dried over $MgSO_4$, filtered and concentrated in vacuo. The obtained crude material was further purified with flash column chromatography on silica (2-5% MeOH/DCM) which afforded the desired product as an orange solid (35 mg, 6% over 2 steps). $^1H$ NMR (400 MHz, $CDCl_3$) δ 8.70 (d, J=9.5 Hz, 1H), 8.51-8.38 (m, 3H), 7.63 (dd, J=9.6, 2.6 Hz, 1H), 3.83-3.70 (m, 2H), 3.70-3.55 (m, 2H), 2.64-2.44 (m, 10H), 2.37 (s, 3H). $^{13}C$ NMR (151 MHz, $CDCl_3$) δ 153.4, 152.4, 143.6, 143.1, 136.0, 135.0, 134.5, 133.4, 127.2, 121.7, 119.0, 118.9, 111.1, 54.8, 54.6, 46.3, 44.8, 44.2, 20.8, 20.8. MS (ESI, positive mode) m/z 383.2 $[M+H]^+$, HR-MS (ESI, pos. mode) m/z 383.1714 calculated for $C_{20}H_{23}N_4O_4$, found m/z 383.1713.

Example 66: Preparation of the building block 2,3-dihydroxy-1-methoxyphenazine 5,10-dioxide

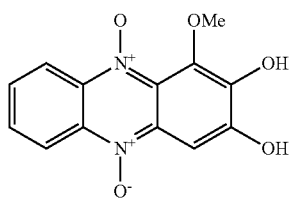 [SMILES: COc1c(O)c(O)cc2c1[n+](O)c1ccccc1[n+]2[O-]]

The title compound is synthesized using 2-methoxy-1,3,4-hydroxy-benzene according to the general procedure in Example 2.

Example 67: Preparation of the building block 2-aminophenazine 5,10-dioxide

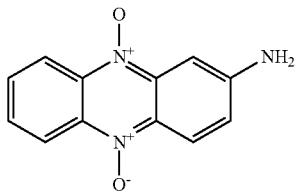 [SMILES: Nc1ccc2c(c1)[n+](O)c1ccccc1[n+]2[O-]]

The title compound may be prepared as described in the literature (El-Haj, Dominy, Johnston, Haddadin and Isidores, *J. Org. Chem.* 1972, 37, 589-593), or by treatment of a 100 mL water suspension of benzofuroxan (2.04 g, 15 mmol) and 4-aminophenol (1.82 g, 17 mmol) with a catalytic amount of sodium hydroxide (38 mg, 1 mmol). After stirring overnight and acidification with acetic acid (0.5 mL), a black precipitate was isolated, redissolved in absolute ethanol, evaporated on silica, and loaded onto a silica plug for purification by way of dry column vacuum chromatography, going stepwise from 1:1 n-heptane/ethyl acetate via ethyl acetate and further up to 10% ethanol in ethyl acetate. This afforded isolation of 1.21 g product in modest purity. An aliquot was purified to analytical purity by recrystallization from hot methanol. $^1$H NMR (400 MHz, DMSO-$d_6$) δ 8.51-8.45 (m, 2H), 8.34 (d, J=9.5 Hz, 1H), 7.84 (m, 1H), 7.74 (m, 1H), 7.39 (d, J=2.3 Hz, 1H), 7.35 (dd, J=9.5, 2.4 Hz, 1H), 6.83 (s, 2H). $^{13}$C NMR (100 MHz, DMSO-$d_6$) δ 151.9, 137.3, 135.4, 132.6, 131.1, 129.8, 128.7, 124.8, 120.9, 119.6, 118.9, 93.6. MS (ESI, positive mode) m/z 250.1 [M+Na]$^+$, HR-MS (ESI, pos. mode) m/z 250.0587 calculated for $C_{12}H_9N_3O_2Na$, found m/z 250.0588.

Example 68: Preparation of the Building Block 7-amino-2,3-dimethylphenazine 5,10-dioxide

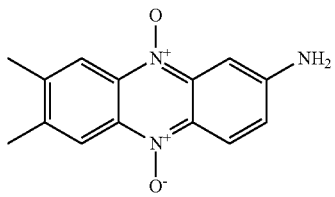 [SMILES: Cc1cc2c(cc1C)[n+](O)c1cc(N)ccc1[n+]2[O-]]

6,7-Dimethylbenzofurazan oxide (246.7 mg, 1.503 mmol) and 4-aminophenol (183.1 mg, 1.678 mmol) was suspended in 10 mL water, and stirred for 19 h after the addition of a catalytic amount of sodium hydroxide (5.4 mg, 0.14 mmol). After acidification with 10 drops of 1M acetic acid, a black precipitate was isolated by way of suction filtration. The precipitate was redissolved in 100 mL absolute ethanol and treated with 77% m-chloroperbenzoic acid (268.3 mg, 1.20 mmol) at 60° C. for 90 minutes. After removal of solvent under reduced pressure, the crude material was redissolved in 100 mL ethyl acetate, washed with 50 mL 10% $Na_2SO_3$ (aq.) and 50 mL 1:1 water/sat. $NaHCO_3$ (aq.). Aqueous phases were back-extracted with ethyl acetate, and combined organic phases were dried over $MgSO_4$ (s) and filtered. Removal of solvent gave 194 mg impure product, which was purified on a silica column with a gradient of 7.5%-10% ethanol in ethyl acetate as eluent. The product was obtained as a black powder, 19.9 mg (5% overall). $^1$H NMR (400 MHz, DMSO-$d_6$) δ 8.30 (d, J=9.5 Hz, 1H), 8.25 (s, 1H), 8.23 (s, 1H), 7.38 (d, J=2.3 Hz, 1H), 7.31 (dd, J=9.5, 2.4 Hz, 1H), 6.72 (s, 2H), 2.48 (s, 3H), 2.46 (s, 3H).

Example 69: Preparation of 2,3-dimethyl-5-((morpholine-4-carbonyl)oxy)quinoxaline 1,4-dioxide

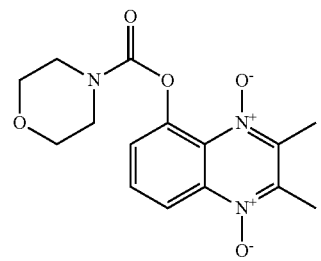 [SMILES: Cc1c(C)[n+]([O-])c2c(OC(=O)N3CCOCC3)cccc2[n+]1[O-]]

Prepared in accordance to general procedure in Example 8 from 5-hydroxy-2,3-dimethylquinoxaline 1,4-dioxide (152 mg scale). Flash column chromatography on silica (0-3% MeOH/DCM) afforded 79 mg (34%) of a light-yellow oil. $R_f$: 0.30 (5% MeOH/DCM). $^1$H NMR (400 MHz, CDCl$_3$) δ 8.56 (dd, J=8.8, 1.4 Hz, 1H), 7.71 (dd, J=8.8, 7.8 Hz, 1H), 7.40 (dd, J=7.8, 1.4 Hz, 1H), 3.91-3.77 (m, 6H), 3.63-3.56 (m, 2H), 2.69 (s, 3H), 2.62 (s, 3H). $^{13}$C NMR (101 MHz, CDCl$_3$) δ 153.6, 143.8, 142.9, 141.5, 138.7, 131.3, 130.6, 125.4, 118.1, 77.5, 77.4, 77.2, 76.8, 66.6, 45.6, 44.7, 14.9, 14.9. HRMS (ESI+): Exact mass calculated for $C_{15}H_{17}N_3O_5Na$ [M+Na]$^+$: 342.1060, found 342.1062 (−0.3 ppm).

Example 70: Preparation of the building block 1-hydroxybenzo[b]phenazine 5,12-dioxide

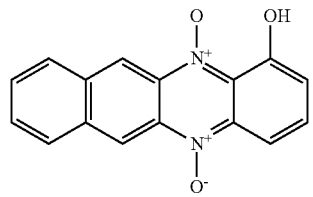 [SMILES: [O-][n+]1c2cc3ccccc3cc2[n+](O)c2c(O)cccc21]

The compound is prepared in 1 gram scale using the procedure in Example 4d.

Example 71: Preparation of 1-((4-methylpiperazine-1-carbonyl)oxy)benzo[b]phenazine 5,12-dioxide

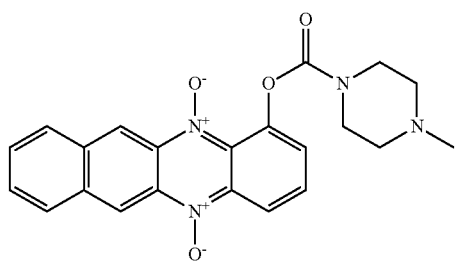 [SMILES: CN1CCN(C(=O)Oc2cccc3c2[n+]([O-])c2cc4ccccc4cc2[n+]3[O-])CC1]

This compound was synthesized according to the general procedure described in Example 8. Flash column chromatography on silica (2-5% MeOH/DCM) afforded 28 mg (97%) of the dark purple solid. $R_f$: 0.23 (5% MeOH/DCM). $^1$H NMR (400 MHz, Chloroform-d) δ 9.25 (s, 1H), 9.19 (s, 1H), 8.63 (dd, J=9.2, 1.3 Hz, 1H), 8.18-8.06 (m, 2H), 7.71-7.60 (m, 3H), 7.34 (dd, J=7.5, 1.3 Hz, 1H), 3.97 (s, 2H), 3.76 (s, 2H), 2.99-2.59 (m, 5H), 2.51 (s, 3H). $^{13}$C NMR (101 MHz, CDCl$_3$) δ 153.6, 143.9, 137.4, 134.7, 134.5, 134.3, 133.3, 131.2, 130.0, 129.1, 129.0, 129.0, 128.9, 124.0, 119.9, 119.5, 118.3, 54.8, 54.7, 46.3, 45.0, 44.3.

Example 72: Anti-AML Activity for Analogs of Iodinin

Dry powder of analogs were dissolved in DMSO. IPC-18 rat AML cells (Lacaze, N. et al. Leuk. Res. 1983, 7, 145.) were cultured in DMEM medium (Sigma-Aldrich, St. Louis, Mo., USA) supplemented with 10% horse serum (Invitrogen, Carlsbad, Calif., USA), and antibiotics (50 U/mL of penicillin and 0.05 mg/mL streptomycin). Molm13 (Matsuo, Y. et al. Leukemia 1997, 11, 1469.) cells were cultured in RPMI supplemented with antibiotics (50 U/mL of penicillin and 0.05 mg/mL streptomycin) and 10% fetal bovine serum (FBS, Invitrogen, Carlsbad, Calif.) and kept in exponential growth before the experiments. Dilution series of iodinin analogs were added to medium and cell suspension added to reach a final cell concentration of 150 000 cells/ml in 0.1 mL in a 96 well tissue culture plate. The maximum concentration of DMSO in the cell suspension was 1%, which resulted in 5% cell death. The cells were incubated with the iodinin analogs for 22 h before WST-1 was added according to the manufacturers protocol, and the cells incubated further in 2 h. Mitochondrial conversion of WST-1 to its colored metabolite was measured by a plate reader at 450 nm, with 620 nm as the reference wavelength. The cells were next fixed by adding 4% buffered formaldehyde (PBS, pH 7.4, supplemented with 0.01 mg/mL Hoechst 33342 for nuclear visualization) to the cell suspension at 1:1 (v/v) ratio (final concentration of formaldehyde:20%). The cells' nuclear and surface morphology were examined microscopically and results compared with the WST-1 viability assay. The results given in Table I are based on WST-1 data.

TABLE 1

IC50 data for iodinin analogs on two different AML cell lines.

| Example no. | Int. name | Name | Molm 13 IC50 2% O$_2$ | Molm 13 IC50 20% O$_2$ | IPC-81 IC50 2% O$_2$ | IPC-81 IC50 20% O$_2$ |
|---|---|---|---|---|---|---|
| Example 1a | IM3 | 1,6-Dimethoxy- phenazine | n.a. | n.a. | n.a | n.a |
| Example 1b | IM1 | 1,6-Dihydroxy-phenazine | | | | |
| Example 1c | IM5 | Iodinin 1,6-Dihydroxy-phenazine-1,5-dioxide | 0.27 | 0.30 | 0.51 | 1.3 |
| Example 5a | IM7 | Myxin 1-Hydroxy-6-methyl-10-(λ$^1$-oxidanyl)-10λ$^4$-phenazine 5-oxide | 1.1 | 1.4 | 3.2 | 2.4 |
| Example 5b | IM15 | 1-(2-(tert-butoxy)-2-oxoethoxy)-6-hydroxyphenazine 5,10-dioxide | 1.65 | 1.77 | | |
| Example 7 | IM18 | 1-(carboxymethoxy)-6-hydroxyphenazine 5,10-dioxide | | | | |
| Example 5c | IM20 | 1-(2-(tert-butoxy)-2-oxoethoxy)-6-methoxyphenazine 5,10-dioxide | 0.65 | 0.85 | | |
| Example 8a | IM32 | 1-hydroxy-6-((4-methylpiperazine-1-carbonyl)oxy)phenazine 5,10-dioxide | | | | |
| Example 8h | IM30 | 1-((dimethylcarbamoyl)oxy)-6-hydroxyphenazine 5,10-dioxide | | | | |
| Example 8i | IM25 | 1-((diethylcarbamoyl)oxy)-6-hydroxyphenazine 5,10-dioxide | 0.74 | 0.76 | | |
| Example 8j | IM33 | 1-hydroxy-6-((pyrrolidine-1-carbonyl)oxy)phenazine 5,10-dioxide | | | | |
| Example 4a | IM35 | 1-hydroxyphenazine 5.10-dioxide | | 4.5 | | |
| Example 6a | IM37 | 1-(2-ethoxy-2-oxoethoxy)phenazine 5,10-dioxide | | 0.11 | | |
| Example 8k | IM36 | 1-((dimethylcarbamoyl)oxy) phenazine 5,10-dioxide | | 0.32 | | |
| Example 8c | IM38 | 1-((4-methylpiperazine-1-carbonyl)oxy)phenazine 5,10-dioxide | | 0.35 | | |
| Example 10 | IM23 | 1-((ethoxycarbonyl)oxy)-6-hydroxyphenazine 5,10-dioxide | | n.a. | | |
| Example 16a | IM34 | | | 0.95 | | |
| Example 16b | IM27 | | | ~40 | | |
| Example 16c | IM21 | | 3.98 | 4.11 | | |
| Example 16d | IM22 | | 5.59 | 4.05 | | |
| Example 16e | IM24 | | 3.50 | 2.23 | | |
| Example 5d | IM26 | | 5.61 | 5.62 | | |
| Example 5e | IM10 | | 1.45 | 1.5 | 1.7 | 1.8 | n.a. = not active at the highest concentration tested (10 microMolar). The data are after 24 h of incubation.

Example 73: Activity of Compounds in AMLcells (MOLM-13), Normal Rat Kidney Epithelial Cells (NRK) and Rat Cardiomyoblast (H9c2) Cells Genera/Procedure—Cell Maintenance and Experimental Conditions All cell culturing media and serum were from Sigma-Aldrich (St. Louis, Mo., USA). Product Nos. are given in parentheses. The human acute myeloid leukemia cell line MOLM-13 was cultured in RPMI medium (R5886) enriched with 1000 fetal bovine serum (F7524) and 0.2 mM L-glutamine (G7513). The normal rat kidney epithelial (NRK) and the rat cardiomyoblast (H9c2) cells were cultured in DMEM medium (D6429) enriched with 10% fetal bovine serum (F7524). All cell lines were additionally supplemented with 100 IU/mL penicillin and 100 mg/mL streptomycin (P0781). The cells were cultured in a humidified atmosphere either under 2% or 20% $O_2$ at 37° C.

All analogues were dissolved in DMSO (D5879, Sigma-Aldrich) at concentrations between 2.5 and 20 mM before testing. For cytotoxic testing, the MOLM-13 cells were seeded as 20,000 cells/well, while NRK and H9c2 cells were seeded as 5,000 cells/well in 96-well Microplates (#167008, Thermo Scientific™ Nunc™ MicroWell™) with 100 μL medium/well. The cells were exposed to various concentrations of iodinin or its analogues for 24 hrs before the cell proliferation reagent WST-1 was used to assess the viability, in accordance with the manufacturer's instructions (11644807001, Roche Diagnostics, Sigma-Aldrich). The cells were next fixed in 2% buffered formaldehyde (pH 7.4) with the DNA-specific dye Hoechst 33342 (Polysciences Inc.) and assessed for cell death by UV-microscopy based on nuclear morphology. The highest concentration of analogue corresponded to 1% of DMSO, which alone gave less than 7% cell death as judged by nuclear morphology.

$EC_{50}$ values were determined by analyses of WST-1 signal results as well as microscopic evaluation of cell death by four-parameter regression analyses using the SigmaPlot software (Systat Software inc. San Jose, Calif.):

$$Y = \min + \frac{(\max - \min)}{1 + \left(\frac{X}{EC50}\right)^h}$$

where Y is the response (WST-1 signal or percent apoptosis), min and max are minimum and maximum response, X is concentration of analogue, $EC_{50}$ equals the point of inflection, i.e. the point that gives half of maximum response, and h is the Hill's slope of the curve. The two methods gave consistent response curves for each analogue. In the case of Tirapazamine, where its colour interfered with the WST-1 signal, only microscopic evaluation of Hoechst stained cells was used in order to calculate its $EC_{50}$ values. The collective results are given in Table 2.

TABLE 2

$IC_{50}$ data for iodinin analogs on two different AML cell lines. n.d. = not done.
The data are after 24 hours of incubation.
Core Table structures:

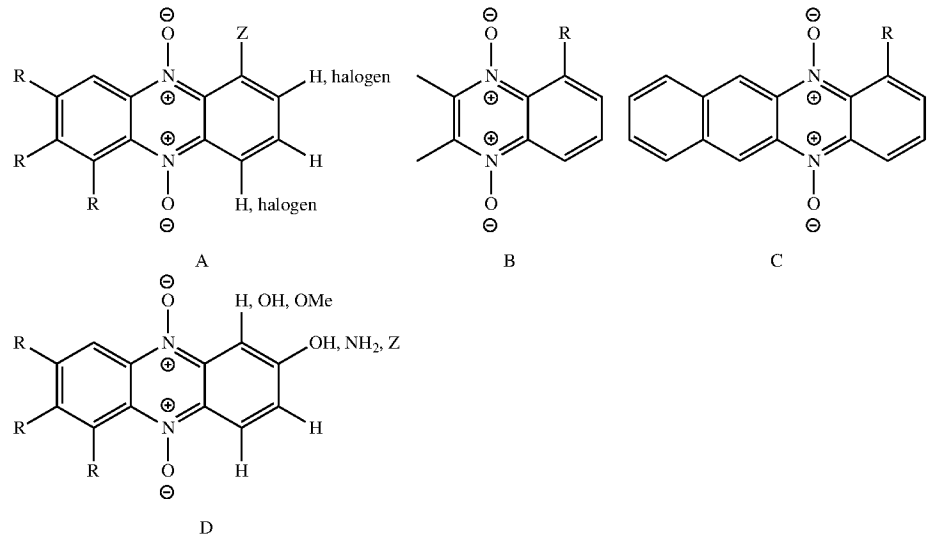

| Patent Example no. | Core | $EC_{50}$ (μM) MOLM-13 | | $EC_{50}$ (μM) NRK | | $EC_{50}$ (μM) H9c2 | $EC_{50}$ (μM) |
| --- | --- | --- | --- | --- | --- | --- | --- |
| | | 19% $O_2$ | 2% $O_2$ | 19% $O_2$ | 2% $O_2$ | 19% $O_2$ | hepG2 |
| 1a | A | 72 ± 14 | 84 ± 6 | n.d. | n.d. | n.d. | n.d. |
| 1b | A | 100-120 | 110-140 | n.d. | n.d. | n.d. | n.d. |
| 1c | A | 2.0 ± 0.07 | 0.79 ± 0.10 | >50 (n = 3) | >50 (n = 3) | >50 (n = 3) | >250 |
| 5a | A | 1.4 ± 0.30 | 0.77 ± 0.13 | 77 ± 11 (n = 2) | 76 ± 14 (n = 2) | 46 ± 4.1 (n = 3) | 70 |
| 5b | A | 2.9 ± 0.34 | 2.4 ± 0.16 | 53 ± 1.5 (n = 2) | 53 ± 0.0 (n = 2) | 42 ± 5.8 (n = 3) | n.d. |

TABLE 2-continued

IC$_{50}$ data for iodinin analogs on two different AML cell lines. n.d. = not done.
The data are after 24 hours of incubation.
Core Table structures:

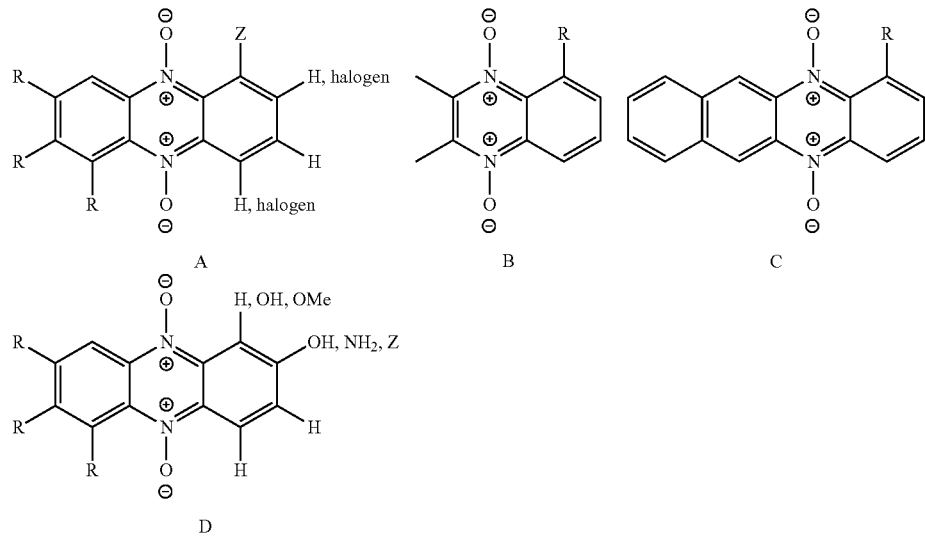

| Patent Example no. | Core | EC$_{50}$ (µM) MOLM-13 19% O$_2$ | EC$_{50}$ (µM) MOLM-13 2% O$_2$ | EC$_{50}$ (µM) NRK 19% O$_2$ | EC$_{50}$ (µM) NRK 2% O$_2$ | EC$_{50}$ (µM) H9c2 19% O$_2$ | EC$_{50}$ (µM) hepG2 |
|---|---|---|---|---|---|---|---|
| 5c | A | 0.57 ± 0.06 | 0.49 ± 0.12 | 11 ± 1.6 (n = 3) | 18 ± 1.5 (n = 3) | 15 ± 0.9 (n = 3) | n.d. |
| 6a | A | 1.5 ± 0.14 (n = 6) | 1.7 ± 0.29 (n = 6) | 26 ± 0.8 (n = 3) | 25 ± 0.2 (n = 3) | 20 ± 2.9 (n = 2) | 75 |
| 6b | A | 8.3 ± 0.78 (n = 6) | 6.3 ± 0.25 (n = 4) | 140 ± 2 (n = 2) | >100 (n = 2) | >100 (n = 2) | n.d. |
| 6c | A | 0.41 ± 0.05 (n = 4) | 0.38 ± 0.04 (n = 4) | 3.1 ± 0.02 (n = 2) | 4.7 ± 0.09 (n = 2) | 1.3 ± 0.2 (n = 3) | 12 |
| 6d | A | 2.4 ± 0.03 (n = 4) | 1.6 ± 0.09 (n = 4) | 10 ± 0.7 (n = 2) | 9.7 ± 2.40 (n = 2) | 3.3 ± 0.50 (n = 2) | 65 |
| 7 | A | 54 ± 7 | 61 ± 4 | n.d. | n.d. | n.d. | n.d. |
| 8a | A | 1.5 ± 0.16 (n = 4) | 1.4 ± 0.06 (n = 4) | 53 ± 2.0 (n = 2) | 59 ± 1.1 (n = 2) | 100 ± 13 (n = 3) | 30 |
| 8b | A | 1.0 ± 0.06 (n = 4) | 0.98 ± 0.08 (n = 4) | 26 ± 2.1 (n = 3) | 39 ± 4.2 (n = 3) | 26 ± 0.9 (n = 3) | 90 |
| 8c | A | 1.5 ± 0.18 (n = 6) | 1.9 ± 0.05 (n = 4) | 25 ± 0.2 (n = 3) | 37 ± 1.9 (n = 3) | 36 ± 11 (n = 2) | n.a. |
| 8d | A | 0.63 ± 0.05 (n = 6) | 0.54 ± 0.06 (n = 4) | 11 ± 1.5 (n = 3) | 13 ± 0.7 (n = 3) | 9.4 ± 0.55 (n = 3) | 105 |
| 8e | A | 0.34 ± 0.04 (n = 4) | 0.32 ± 0.06 (n = 4) | 10 ± 0.9 (n = 3) | 15 ± 1.8 (n = 3) | 3.2 ± 0.10 (n = 3) | 45 |
| 8g | A | 0.89 ± 0.03 (n = 4) | 0.70 ± 0.04 (n = 4) | 49 ± 1.8 (n = 2) | 62 ± 1.3 (n = 2) | 64 ± 9.2 (n = 2) | n.a. |
| 8j | A | 0.86 ± 0.05 (n = 6) | 0.79 ± 0.09 (n = 4) | 9.6 ± 0.38 (n = 3) | 15 ± 1.0 (n = 3) | 12 ± 0.7 (n = 2) | n.a. |
| 8k | A | 1.3 ± 0.15 (n = 6) | 2.1 ± 0.16 (n = 4) | 19 ± 1.3 (n = 3) | 25 ± 0.6 (n = 3) | 16 ± 2.6 (n = 2) | n.a. |
| 8l | A | 2.0 ± 0.11 (n = 4) | 1.8 ± 0.17 (n = 6) | 32 ± 2.5 (n = 2) | 35 ± 1.5 (n = 2) | 35 ± 3.3 (n = 3) | 110 |
| 8m | A | 1.9 ± 0.07 (n = 4) | 1.7 ± 0.09 (n = 4) | 22 ± 1.7 (n = 2) | 29 ± 0.7 (n = 2) | 35 ± 1.8 (n = 3) | n.a. |
| 10 | A | 50 ± 0.4 (n = 4) | 66 ± 2.2 (n = 4) | n.a. | n.a. | >100 (n = 2) | n.a. |
| 12 | B | >200 (n = 4) | >200 (n = 4) | n.a. | n.a. | n.a. | n.a. |
| 13 | B | >200 (n = 4) | >200 (n = 4) | n.a. | n.a. | n.a. | n.a. |
| 16b | A | 36 ± 0.1 (n = 5) | 22 ± 2.8 (n = 4) | n.d. | n.d. | >200 (n = 2) | n.a. |
| 16c | A | 2.0 ± 0.47 | 0.79 ± 0.06 | >20 (n = 3) | >20 (n = 3) | >20 (n = 3) | n.a. |
| 16d | A | 11 ± 0.7 (n = 4) | 8.9 ± 1.71 (n = 4) | n.a. | n.a. | >50 (n = 2) | n.a. |
| 16e | A | 6.1 ± 0.05 (n = 4) | 4.0 ± 0.33 (n = 4) | >25 (n = 2) | >25 (n = 2) | >25 (n = 2) | n.a. |

TABLE 2-continued

IC$_{50}$ data for iodinin analogs on two different AML cell lines. n.d. = not done.
The data are after 24 hours of incubation.
Core Table structures:

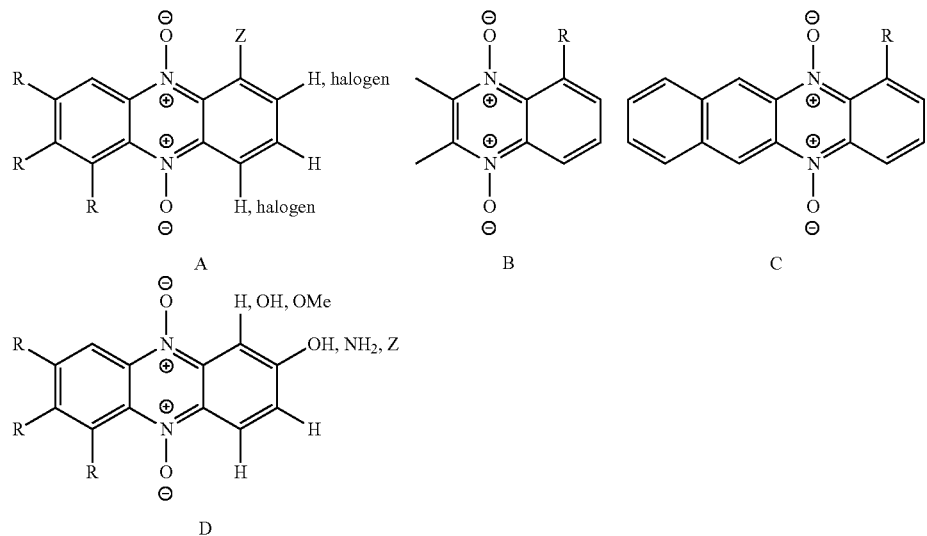

| Patent Example no. | Core | EC$_{50}$ (µM) MOLM-13 | | EC$_{50}$ (µM) NRK | | EC$_{50}$ (µM) H9c2 | EC$_{50}$ (µM) hepG2 |
|---|---|---|---|---|---|---|---|
| | | 19% O$_2$ | 2% O$_2$ | 19% O$_2$ | 2% O$_2$ | 19% O$_2$ | |
| 17 | A | 11 ± 1.8 (n = 6) | 12 ± 0.04 (n = 4) | 79 ± 4.2 (n = 3) | >100 (n = 3) | >100 (n = 2) | n.a. |
| 19 | A | 2.2 ± 0.09 (n = 6) | 1.9 ± 0.11 (n = 4) | 26 ± 0.7 (n = 3) | 25 ± 1.9 (n = 3) | 20 ± 2.1 (n = 2) | n.a. |
| 20 | A | | | | | | n.a. |
| 21 | A | 1.2 ± 0.08 (n = 4) | 1.4 ± 0.15 (n = 6) | 13 ± 0.01 (n = 2) | 16 ± 1.0 (n = 2) | 23 ± 0.1 (n = 2) | n.a. |
| 24 | A | 1.5 ± 0.18 (n = 6) | 1.2 ± 0.15 (n = 4) | 18 ± 0.6 (n = 3) | 21 ± 2.4 (n = 3) | 13 ± 0.5 (n = 2) | n.a. |
| 33 | A | 4.0 ± 0.48 | 3.1 ± 0.83 | | | n.a. | n.a. |
| 36 | A | 4.2 ± 0.20 | 3.3 ± 0.22 | 27 ± 1.2 (n = 2) | 27 ± 1.8 (n = 2) | n.a. | n.a. |
| 37 | A | 18 ± 3 | 39 ± 9 | >200 (n = 2) | >200 (n = 2) | n.d. | n.a. |
| 48 | A | 2.8 ± 0.25 (n = 6) | 2.3 ± 0.10 (n = 4) | >50 (n = 2) | >50 (n = 2) | >50 (n = 2) | n.a. |
| 50 | A | 1.8 ± 0.24 (n = 6) | 3.4 ± 0.78 (n = 4) | 21 ± 0.3 (n = 2) | 52 ± 1.2 (n = 2) | 41 ± 5.7 (n = 2) | n.a. |
| 51 | A | | | | | | n.a. |
| 52 | A | 1.5 ± 0.02 (n = 4) | 0.78 ± 0.11 (n = 4) | 6.6 ± 0.04 (n = 2) | 8.9 ± 0.0 (n = 2) | 8.7 ± 1.2 (n = 2) | n.a. |
| 59 | A | 0.41 ± 0.04 (n = 4) | 0.23 ± 0.03 (n = 4) | 6.2 ± 0.02 (n = 2) | 7.6 ± 0.60 (n = 2) | 2.2 ± 0.53 (n = 3) | 40 |
| 60 | D | 128 ± 3.0 (n = 2) | 45 ± 3.5 (n = 3) | n.a. | n.a. | >200 (n = 2) | n.a. |
| 61 | D | | | n.a. | n.a. | | n.a. |
| 62 | D | 32 ± 5.0 (n = 2) | 15 ± 0.7 (n = 3) | n.a. | n.a. | 45 ± 4.8 (n = 2) | n.a. |
| 63 | D | 14 ± 0.4 (n = 2) | 3.5 ± 0.19 (n = 2) | n.a. | n.a. | 53 ± 0.3 (n = 2) | n.a. |
| 64 | D | 117 ± 1.0 (n = 2) | 50 ± 3.8 (n = 3) | n.a. | n.a. | >200 (n = 2) | n.a. |
| 65 | D | 17 ± 0.0 (n = 2) | 2.5 ± 0.24 (n = 3) | n.a. | n.a. | 20 ± 2.4 (n = 2) | n.a. |
| 66 | D | | | n.a. | n.a. | | n.a. |
| 67 | D | 31 ± 1.4 (n = 2) | 7.6 ± 0.89 (n = 3) | n.a. | n.a. | 80 ± 8.9 (n = 2) | n.a. |
| 69 | B | >200 (n = 4) | >200 (n = 4) | n.a. | n.a. | — | n.a. |
| 71 | C | 2.8 ± 0.18 (n = 4) | 1.8 ± 0.10 (n = 4) | 2.0 ± 0.06 (n = 2) | 7.5 ± 0.38 (n = 2) | 2.3 ± 0.05 (n = 2) | n.a. | n.a.: not analysed.

Example 74: Membrane Permeability Assay of Compounds

The Corning Gentest™ pre-Coated parallel artificial membrane permeability assay PAMPA Plate System was from Cording Discovery Labware (Bedford, USA). The compounds were tested in room temperature at 50 μM using PBS as buffer. A total of 300 μl of the compound solution was added to each well of the donor plate, and 200 μl of PBS was added to the receiver filter plate. After incubation for five hours, 50 μl of the donor or acceptor well were injected into a reversed phase HPLC column (Kromasil 100-5 C18 150-4.6 mm, Akzo Nobel, Sweden) connected to a Merck-Hitachi LaChrome HPLC-system (VWR, WestChester, USA) with a L-7455 diode array detector. Mobile phase A was 0.05% aqueous TFA, and mobile phase B was acetonitrile. The flow rate was 1.6 ml/min and compounds eluted between 1 and 4.5 minutes was eluted during a 6.5 min gradient from 90:10% mobile phase A:B to 0:100% mobile phase A:B. The ratio of the compound concentrations in the donor and acceptor compartment was calculated after integration of the peaks at 285 nm. $P_{eff}$ was calculated as described in [Bennion B J, Be N A, McNerney M W, Lao V, Carlson E M, Valdez C A, et al. Predicting a Drug's Membrane Permeability: A Computational Model Validated With in Vitro Permeability Assay Data. The journal of physical chemistry B. 2017; 121(20):5228-37.]. Membrane permeability were classified by the range defined by Bennion et al., allowing for us to divide the compounds into four groups, compounds with high permeability (LogPeff>−5.33), intermediate permeability (LogPeff>−5.66 and <−5.33), low permeability (LogPeff>−6.14 and <−5.66) impermeable (LogPeff<−6.14). Table 3 shows the permeability of analogs.

TABLE 3

Permeability of analogs

| Example | LogP$_{eff}$[1] | Deviation[2] | Permeability[3] |
|---|---|---|---|
| 1c (Iodinin) | −5.46* | 0.43 | Intermediate |
| 1b | −5.42 | −0.08 | Intermediate/high |
| 5a | −5.29 | 0.00 | High |
| 5b | −5.33 | 0.02 | High |
| 7 | −7.53 | −0.60 | Impermeable |
| 5c | −4.70 | −0.09 | High |
| 16d | −5.86* | 0.97 | Low |
| 10 | −7.38* | 0.15 | Impermeable |
| 16b | −8.66 | 0.03 | Impermeable |
| 6c | −5.42 | 0.02 | Intermediate/high |
| 8e | −5.38 | 0.01 | Intermediate/high |
| 8b | −5.77 | −0.02 | Low |
| 70 | −8.04 | −0.08 | Impermeable |
| 71 | −5.43 | −0.02 | Intermediate/high |
| 52 | −5.32 | 0.01 | High |
| 50 | −5.42 | −0.01 | Intermediate/high |
| Tirapazamine | −5.79 | −0.09 | Low |

[1]Asterisks denote that n = 3. For all other samples, n = 2.
[2]Deviation is calculated either as SDT (n = 3) or high value minus average (n = 2)
[3]As defined in: Bennion BJ, Be NA, McNerney MW, Lao V, Carlson EM, Valdez CA, et al. Predicting a Drug's Membrane Permeability: A Computational Model Validated With in Vitro Permeability Assay Data. The Journal of Physical Chemistry B. 2017; 121(20): 5228-37

Example 75: General Protocol for Microbroth Dilution Method for Evaluating Antibacterial Activity of Compounds or Synergistic Effect of Compound-Antibiotic Combination Preparation of Bacteria
Day 1:
Plate bacterial strain(s) on appropriate media:
Gram-negative bacteria with ESBLs or carbapenemases: green agar plates with 100 mg/L ampicillin
Gram-negative bacteria without β-lactamases: green agar plates
Gram-positive bacteria (Staphylococci and Enterococci): blood agar plates
Incubate o.n. at 37° C.
Day 2:
Prepare the Bacterial Inoculum:
Prepare a 0.5 McFarland suspension of bacteria in 0.85% NaCl. (Should be used within 15 min of preparation).
Dilute the 0.5 McFarland suspension 1:100 into MH broth.
Check the inoculum by diluting the prepared bacterial suspension 1:100 (10 μl bacterial suspension+990 μl 0.85% NaCl). Plate 10 μl of the dilution on MH agar plates (×2). Incubate o.n. at 37° C., count the colonies and calculate the final CFU/ml inoculum in the plate by multiplying the average number of colonies with 10000 and divide by 2. The final inoculum should be between 3-7×10$^5$ CFU/ml.
Add 50 μl of the prepared bacterial suspension to each well in the microtiter plate except negative growth control.
Preparation of Compounds/Antibiotics
Calculate the desired concentration-range and volume of the compounds/antibiotics in the assay. For antibiotics this will depend on the MIC to meropenem of the bacterial strains to be tested. Dilute the stock solution in MH broth. Make subsequent 2-fold dilutions in MH broth of the desired concentrations if a concentration range is to be tested (remember the extra dilution factor in the assay plate). Always include extra volume for pipetting. Take into consideration stock solutions that are made in buffers that have an effect on bacterial growth (e.g. DMSO).
Assay:
Determining the MIC of compounds/antibiotics alone:
Add 25 μl of each concentration of compound/antibiotic to row 2-11 (highest concentration in row 2)
Add 25 μl MH broth to row 2-11
Add 50 μl MH broth to row 12 (positive control)
Add 100p MH broth to row 1
Add 50 μl bacterial suspension to row 2-12.
Determining the MIC of antibiotics+compounds:
Add 25 μl of each concentration of antibiotic to row 2-11 (highest concentration in row 2)
Add 25 μl of compound to row 2-11
Add 50 μl MH broth to row 12 (positive control)
Add 100p MH broth to row 1
Add 50 μl bacterial suspension to row 2-12.
Incubate the plate for 20 hrs at 37° C. and determine the MIC in the presence and absence of inhibitor.

This experimental design was used for the results in Tables 4 and 5 below. In Table 4, inhibitor concentration dependency on the MIC of meropenem was studied.

TABLE 4

MIC values of Example 6a alone and in combination with the carbapenem meropenem (MEM)

| | MIC with MEM and Example 6a alone in the respective strains | | | | | | |
|---|---|---|---|---|---|---|---|
| Conc. of compound | S1 | S2 | S3 | S4 | S5 | S6 | S7 |
| MIC Ex. 6a alone | n.t. | n.t. | 39.3 | 19.6 | 2.5 | 9.7 | 5 |
| MIC MEM alone | >64 | 8 | 32 | 64 | 1 | >64 | >64 |

| MEM + Example 6a: | MIC with MEM + Example 6a in the respective strains | | | | | | |
|---|---|---|---|---|---|---|---|
| Conc of 6a | 15.7 | ≤0.03 | ≤0.03 | ≤0.03 | ≤0.03 | ≤0.03 | ≤0.03 | ≤0.03 |
| | 7.9 | ≤0.03 | 8 | 32 | ≤0.03 | ≤0.03 | ≤0.03 | ≤0.03 |
| | 3.9 | >64 | 8 | 32 | 8 | ≤0.03 | >64 | ≤0.03 |
| | 1.3 | >64 | 8 | 32 | 64 | 1 | >64 | >64 |

MEM: meropenem. N.t .: not tested. All MIC values given in mg/L. Strains used in the Table: Strains lacking metallo-β-lactamase: strain 1 (S1): *P. aeruginosa* (16H5), strain 2 (S2): *K. pneumoniae* (17A2). Strains harboring metallo-β-lactamase: strain 3 (S3): *P. aeruginosa*/VIM-2, strain 4 (S4): *K. pneumoniae*/NDM-1. Strains harboring serine--β-lactamase: strain 5 (S5): *E. coli*/OXA-48, strain 6 (S6): *K. pneumoniae*/KPC-2, strain 7 (S7): *A.baumannii*/OXA-23

TABLE 5

MIC values of different examples alone against vancomycin-resistant *E. faecium* and methicillin-resistant *S. aureus*

| | Gram-positive strains | |
|---|---|---|
| Compound | A1-22 E. faecium vanA | A4-37 S. aureus MRSA |
| Inactive cpd. | >125 | >125 |
| 5b | 8 | <0.5 |
| 8i | 8 | <4 |
| 6a | 4 | <0.5 |
| 8c | 8 | <4 |
| 8m | 63 | <4 |
| 8l | 63 | <4 |
| 18 | 32 | <2 |
| 6d | 8 | 16 |
| 5a | <8 | <0.5 |

The invention claimed is:

1. A combination product comprising:
meropenem; and
a compound of the following formula:

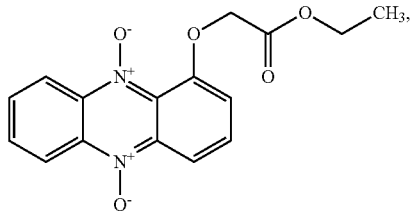 [SMILES: CCOC(=O)COc1cccc2c1[n+]([O-])c1ccccc1[n+]2[O-]]

or a pharmaceutically acceptable salt thereof.

2. A pharmaceutical composition comprising the combination product according to claim 1 together with at least one pharmaceutically acceptable carrier or excipient.

3. A method for treating a bacterial infection or fungal infection in a patient, wherein the method comprises administering to the patient in need thereof a therapeutically effective amount of the combination product according to claim 1.

4. The method according to claim 3, wherein the bacterial infection or fungal infection is caused by a bacteria or fungus selected from the group consisting of Acetobacter aurantius, Acinetobacter bitumen, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bacteroides melaninogenicus, Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacterium fusiforme, Coxiella burnetii, Diplococcus pneumoniae, Ehrlichia chaffeensis, Enterobacter cloacae, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Klebsiella pneumoniae, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma gallinarum, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae,

*Rochalimaea quintana, Rothia dentocariosa, Salmonella enteritidis, Salmonella schottmuelleri, Salmonella typhi, Salmonella typhimurium, Serratia marcescens, Shigella dysenteriae, Spirillium volutans, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema denticola, Treponema pallidum, Vibrio cholerae, Vibrio comma, Vibrio parahaemolyticus, Vibrio vulnificus, Viridans streptococci, Wolbachia, Yersinia enterocolitica, Yersinia pestis*, and *Yersinia pseudotuberculosis*.

5. A method for treating a bacterial infection or fungal infection in a patient, wherein the method comprises administering to the patient in need thereof a therapeutically effective amount of the pharmaceutical composition according to claim 2.

6. The method according to claim 5, wherein the bacterial infection or fungal infection is caused by a bacteria or fungus selected from the group consisting of *Acetobacter aurantius, Acinetobacter bitumen, Actinomyces israelii, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bacteroides melaninogenicus, Bartonella henselae, Bartonella quintana, Bordetella bronchiseptica, Bordetella pertussis, Borrelia burgdorferi, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacterium fusiforme, Coxiella burnetii, Diplococcus pneumoniae, Ehrlichia chaffeensis, Enterobacter cloacae, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Klebsiella pneumoniae, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma gallinarum, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella schottmuelleri, Salmonella typhi, Salmonella typhimurium, Serratia marcescens, Shigella dysenteriae, Spirillium volutans, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema denticola, Treponema pallidum, Vibrio cholerae, Vibrio comma, Vibrio parahaemolyticus, Vibrio vulnificus, Viridans streptococci, Wolbachia, Yersinia enterocolitica, Yersinia pestis*, and *Yersinia pseudotuberculosis*.

\* \* \* \* \*